United States Patent
Farina et al.

(10) Patent No.: US 9,174,971 B2
(45) Date of Patent: Nov. 3, 2015

(54) PROCESS FOR THE PREPARATION OF COMPOUNDS USEFUL AS INHIBITORS OF SGLT2

(75) Inventors: Vittorio Farina, Beerse (BE); Sebastien François Emmanuel Lemaire, Brussels (BE); Ioannis N. Houpis, Antwerp (BE)

(73) Assignee: Janssen Pharmaceutica NV, Beerse (BE)

( * ) Notice: Subject to any disclaimer, the term of this patent is extended or adjusted under 35 U.S.C. 154(b) by 399 days.

(21) Appl. No.: 12/904,233

(22) Filed: Oct. 14, 2010

(65) Prior Publication Data

US 2011/0087017 A1   Apr. 14, 2011

Related U.S. Application Data

(60) Provisional application No. 61/251,378, filed on Oct. 14, 2009.

(51) Int. Cl.
| | | |
|---|---|---|
| *C07D 309/10* | (2006.01) | |
| *C07D 409/14* | (2006.01) | |
| *C07D 409/10* | (2006.01) | |
| *C07F 3/06* | (2006.01) | |

(52) U.S. Cl.
CPC ............ *C07D 409/14* (2013.01); *C07D 309/10* (2013.01); *C07D 409/10* (2013.01); *C07F 3/06* (2013.01)

(58) Field of Classification Search
None
See application file for complete search history.

(56) References Cited

U.S. PATENT DOCUMENTS

| | | | |
|---|---|---|---|
| 2,799,241 | A | 7/1949 | Wurster |
| 4,160,861 | A | 7/1979 | Cole et al. |
| 4,584,369 | A | 4/1986 | Klein et al. |
| 5,149,838 | A | 9/1992 | Humphrey et al. |
| 5,292,461 | A | 3/1994 | Juch et al. |
| 5,401,435 | A | 3/1995 | Burzio et al. |
| 5,424,406 | A | 6/1995 | Tsujihara et al. |
| 5,610,294 | A | 3/1997 | Lam et al. |
| 5,731,292 | A | 3/1998 | Tsujihara et al. |
| 5,767,094 | A | 6/1998 | Tsujihara et al. |
| 5,780,483 | A | 7/1998 | Widdowson et al. |
| 5,830,873 | A | 11/1998 | Tsujihara et al. |
| 5,861,385 | A | 1/1999 | Angerbauer et al. |
| 5,945,533 | A | 8/1999 | Kometani et al. |
| 6,048,842 | A | 4/2000 | Tsujihara et al. |
| 6,069,238 | A | 5/2000 | Hitchcock et al. |
| 6,153,632 | A | 11/2000 | Rieveley |
| 6,277,833 | B1 | 8/2001 | Angerbauer et al. |
| 6,297,363 | B1 | 10/2001 | Kubo et al. |
| 6,414,126 | B1 | 7/2002 | Ellsworth et al. |
| 6,420,513 | B2 | 7/2002 | Minami |
| 6,448,415 | B1 | 9/2002 | Lee et al. |
| 6,475,521 | B1 | 11/2002 | Timmins et al. |
| 6,479,661 | B1 | 11/2002 | Buchholz et al. |
| 6,515,117 | B2 | 2/2003 | Ellsworth et al. |
| 6,562,791 | B1 | 5/2003 | Maurya et al. |
| 6,617,313 | B1 | 9/2003 | Maurya et al. |
| 6,627,611 | B2 | 9/2003 | Tomiyama et al. |
| 6,800,761 | B1 | 10/2004 | Franc et al. |
| 7,008,959 | B2 | 3/2006 | Franc et al. |
| 7,045,665 | B2 | 5/2006 | Fujikura et al. |
| 7,074,826 | B2 | 7/2006 | Wechter et al. |
| 7,084,123 | B2 | 8/2006 | Fujikura et al. |
| 7,202,350 | B2 | 4/2007 | Imamura et al. |
| 7,271,153 | B2 | 9/2007 | Nishimura et al. |
| 7,288,528 | B2 | 10/2007 | Frick et al. |
| 7,294,618 | B2 | 11/2007 | Fushimi et al. |
| 7,375,213 | B2 | 5/2008 | Deshpande et al. |
| 7,417,032 | B2 | 8/2008 | Eckhardt et al. |
| 7,511,022 | B2 | 3/2009 | Beavers et al. |
| 7,566,699 | B2 | 7/2009 | Fushimi et al. |
| 7,576,064 | B2 | 8/2009 | Kikuchi et al. |
| 7,666,845 | B2 | 2/2010 | Cook et al. |
| 7,932,379 | B2 | 4/2011 | Deshpande et al. |
| 7,943,582 | B2 | 5/2011 | Nomura et al. |
| 7,943,788 | B2 | 5/2011 | Nomura et al. |
| 2001/0041674 | A1 | 11/2001 | Tomiyama et al. |
| 2002/0032164 | A1 | 3/2002 | Dale et al. |
| 2002/0052326 | A1 | 5/2002 | Washburn |
| 2002/0111315 | A1 | 8/2002 | Washburn et al. |
| 2003/0024914 | A1 | 2/2003 | Aleshin |
| 2003/0064935 | A1 | 4/2003 | Gougoutas |
| 2003/0087843 | A1 | 5/2003 | Washburn |
| 2003/0114390 | A1 | 6/2003 | Washburn et al. |
| 2003/0191121 | A1 | 10/2003 | Miller et al. |
| 2004/0053855 | A1 | 3/2004 | Fujikura et al. |
| 2004/0063646 | A1 | 4/2004 | Fujikura et al. |
| 2004/0110936 | A1 | 6/2004 | Ohsumi et al. |
| 2004/0116357 | A1 | 6/2004 | Fushimi et al. |
| 2004/0132669 | A1 | 7/2004 | Nishimura et al. |

(Continued)

FOREIGN PATENT DOCUMENTS

| | | |
|---|---|---|
| CA | 2494177 A1 | 2/2004 |
| EP | 0355750 A1 | 2/1990 |

(Continued)

OTHER PUBLICATIONS

Greene, "Protective groups in Organic Synthesis" published 1999 by Wiley, p. 170.*
Watanabe et al., "Cyclopentyl Methyl Ether as a New and Alternative Process Solvent" Organic Process Research and Development (2007) vol. 11 pp. 251-258.*
Lieberman et al., "Pharmaceutical Dosage Forms" Second Edition, vol. 2 published 1990 by Marcel Dekker Inc, pp. 462-472.*
Braga et al., "Making Crystals from Crystals: a green route to crystal engineering and polymorphism" ChemComm (2005) pp. 3635-3645.*
Jain et al., "Polymorphism in Pharmacy" Indian Drugs (1986) vol. 23 No. 6 pp. 315-329.*
Vippagunta et al., "Crystalline Solids" Advanced Drug Delivery Reviews (2001) vol. 48 pp. 3-26.*

(Continued)

*Primary Examiner* — Eric Olson

(57) ABSTRACT

The present invention is directed to a novel process for the preparation of compounds having inhibitory activity against sodium-dependent glucose transporter (SGLT) being present in the intestine or kidney.

35 Claims, No Drawings

(56) References Cited

U.S. PATENT DOCUMENTS

| | | | |
|---|---|---|---|
| 2004/0138143 | A1 | 7/2004 | Glombik et al. |
| 2004/0259819 | A1 | 12/2004 | Frick et al. |
| 2005/0014704 | A1 | 1/2005 | Frick et al. |
| 2005/0032711 | A1 | 2/2005 | Patel et al. |
| 2005/0032712 | A1 | 2/2005 | Urbanski |
| 2005/0037980 | A1 | 2/2005 | Rybczynski et al. |
| 2005/0037981 | A1 | 2/2005 | Beavers et al. |
| 2005/0049203 | A1 | 3/2005 | Nishimura et al. |
| 2005/0124555 | A1 | 6/2005 | Tomiyama et al. |
| 2005/0124556 | A1 | 6/2005 | Burton |
| 2005/0209166 | A1 | 9/2005 | Eckhardt et al. |
| 2005/0233988 | A1 | 10/2005 | Nomura et al. |
| 2005/0256317 | A1 | 11/2005 | Sato et al. |
| 2006/0009400 | A1 | 1/2006 | Eckhardt et al. |
| 2006/0035841 | A1 | 2/2006 | Eckhardt et al. |
| 2006/0122126 | A1 | 6/2006 | Imamura et al. |
| 2006/0189548 | A1 | 8/2006 | Himmelsbach et al. |
| 2006/0217323 | A1 | 9/2006 | Patel et al. |
| 2006/0229260 | A1 | 10/2006 | Rybczynski et al. |
| 2006/0234954 | A1 | 10/2006 | Urbanski |
| 2006/0247179 | A1 | 11/2006 | Fushimi et al. |
| 2006/0258749 | A1 | 11/2006 | Eckhardt et al. |
| 2006/0293251 | A1 | 12/2006 | Urbanski et al. |
| 2007/0027092 | A1 | 2/2007 | Himmelsbach et al. |
| 2007/0049537 | A1 | 3/2007 | Eckhardt et al. |
| 2007/0060531 | A1 | 3/2007 | Kikuchi et al. |
| 2007/0060545 | A1 | 3/2007 | Nomura et al. |
| 2008/0027122 | A1 | 1/2008 | Nomura et al. |
| 2008/0119422 | A1 | 5/2008 | Nomura et al. |
| 2008/0132563 | A1 | 6/2008 | Kakinuma et al. |
| 2008/0146515 | A1 | 6/2008 | Nomura et al. |
| 2008/0234366 | A1 | 9/2008 | Bindra et al. |
| 2009/0124702 | A1 | 5/2009 | Siva Satya Krishna Babu et al. |
| 2009/0233874 | A1 | 9/2009 | Abdel-Magid et al. |
| 2010/0099883 | A1 | 4/2010 | Fillers et al. |
| 2011/0009347 | A1 | 1/2011 | Liang et al. |
| 2011/0212905 | A1 | 9/2011 | Nomura et al. |
| 2012/0058941 | A1 | 3/2012 | Nomura et al. |
| 2012/0115799 | A1 | 5/2012 | Wang et al. |

FOREIGN PATENT DOCUMENTS

| | | | |
|---|---|---|---|
| EP | 0348184 | B1 | 3/1993 |
| EP | 0579204 | A2 | 1/1994 |
| EP | 0579204 | A3 | 1/1994 |
| EP | 0625513 | B1 | 9/1999 |
| EP | 1172362 | A1 | 1/2002 |
| EP | 1338603 | A1 | 8/2003 |
| EP | 1528066 | A1 | 5/2005 |
| EP | 1845095 | | 10/2007 |
| EP | 1956023 | * | 8/2008 |
| GB | 2359554 | | 8/2001 |
| JP | 59039889 | A | 3/1984 |
| JP | 63-233975 | A | 9/1988 |
| JP | H03-503280 | | 7/1991 |
| JP | 4-253974 | A | 9/1992 |
| JP | 06246354 | A | 9/1994 |
| JP | 07242526 | A | 9/1995 |
| JP | 9-263549 | A | 10/1997 |
| JP | 10-324632 | A | 12/1998 |
| JP | 2000-34230 | A | 2/2000 |
| JP | 2000-34239 | A | 2/2000 |
| JP | 2001-288178 | A | 10/2001 |
| JP | 2002167430 | A | 6/2002 |
| JP | 2003-12686 | A1 | 1/2003 |
| JP | 2003238417 | A | 8/2003 |
| JP | 2003313168 | A | 11/2003 |
| JP | 2007-230999 | A | 9/2007 |
| WO | WO 93/09100 | A1 | 5/1993 |
| WO | WO 93/21178 | A1 | 10/1993 |
| WO | WO 94/14807 | A1 | 7/1994 |
| WO | WO 96/13258 | A1 | 5/1996 |
| WO | WO 97/17949 | A1 | 5/1997 |
| WO | WO 97/25033 | A1 | 7/1997 |
| WO | WO 98/42347 | A1 | 10/1998 |
| WO | 99/65861 | A1 | 12/1999 |
| WO | WO 99/67236 | A | 12/1999 |
| WO | WO 00/27823 | A1 | 5/2000 |
| WO | WO 00/28989 | A1 | 5/2000 |
| WO | WO 00/74681 | A1 | 12/2000 |
| WO | WO 01/27128 | | 4/2001 |
| WO | WO 01/64669 | A1 | 9/2001 |
| WO | WO 01/68660 | A1 | 9/2001 |
| WO | WO 01/74834 | A1 | 10/2001 |
| WO | WO 01/74835 | A1 | 10/2001 |
| WO | WO 01/85167 | A1 | 11/2001 |
| WO | WO 02/26706 | A2 | 4/2002 |
| WO | WO 02/053573 | A1 | 7/2002 |
| WO | WO 02/068439 | A1 | 9/2002 |
| WO | WO 02/068440 | A1 | 9/2002 |
| WO | WO 02/070020 | A2 | 9/2002 |
| WO | WO 02/070020 | A3 | 9/2002 |
| WO | WO 02/083066 | A2 | 10/2002 |
| WO | WO 02/088157 | A1 | 11/2002 |
| WO | WO 02/094262 | A1 | 11/2002 |
| WO | WO 02/096357 | A2 | 12/2002 |
| WO | WO 03/000712 | A1 | 1/2003 |
| WO | WO 03/011880 | A1 | 2/2003 |
| WO | WO 03/020737 | A1 | 3/2003 |
| WO | 03/040121 | A1 | 5/2003 |
| WO | WO 03/043621 | A1 | 5/2003 |
| WO | WO 03/087104 | A1 | 10/2003 |
| WO | WO 03/099836 | A1 | 12/2003 |
| WO | WO 2004/007517 | A1 | 1/2004 |
| WO | WO 2004/013118 | A1 | 2/2004 |
| WO | WO 2004/014931 | A1 | 2/2004 |
| WO | WO 2004/019958 | A1 | 3/2004 |
| WO | WO 2004/052902 | A1 | 6/2004 |
| WO | WO 2004/052903 | A1 | 6/2004 |
| WO | WO 2004/063209 | A2 | 7/2004 |
| WO | WO 2004/063209 | A3 | 7/2004 |
| WO | WO 2004/064806 | A | 8/2004 |
| WO | WO 2004/076470 | A2 | 9/2004 |
| WO | WO 2004/080990 | A1 | 9/2004 |
| WO | WO 2004/087727 | A1 | 10/2004 |
| WO | WO 2004/099230 | A1 | 11/2004 |
| WO | WO 2004/113359 | A1 | 12/2004 |
| WO | WO 2005/009539 | A2 | 2/2005 |
| WO | WO 2005/009954 | A2 | 2/2005 |
| WO | WO 2005/012326 | A1 | 2/2005 |
| WO | WO 2005/058845 | A2 | 6/2005 |
| WO | WO 2006/010557 | | 2/2006 |
| WO | WO 2006/080577 | A1 | 8/2006 |
| WO | WO 2006/108842 | A1 | 10/2006 |
| WO | WO 2007/025943 | A2 | 3/2007 |
| WO | WO 2007/031548 | A2 | 3/2007 |
| WO | WO 2007/087441 | A2 | 8/2007 |
| WO | 89/05639 | A1 | 9/2007 |
| WO | WO 2008/013322 | A1 | 1/2008 |
| WO | WO 2008/020011 | A1 | 2/2008 |
| WO | WO 2008/034859 | A1 | 3/2008 |
| WO | WO 2008/055870 | A1 | 5/2008 |
| WO | WO 2008/055940 | A2 | 5/2008 |
| WO | WO 2008/069327 | A1 | 6/2008 |
| WO | WO 2008/070609 | A1 | 6/2008 |
| WO | WO 2009/023537 | | 2/2009 |
| WO | WO 2009/035969 | A1 | 3/2009 |
| WO | WO 2009/091082 | A1 | 7/2009 |
| WO | WO 2009/121945 | A2 | 10/2009 |

OTHER PUBLICATIONS

Unger et al., "Hyperglycemia as an inducer as well as a consequence of impaired islet cell function and insulin resistance: implication for the management of diabetes", *Diabetologia*, 1985, pp. 119-121, vol. 28.

Rossetti et al., "Glucose Toxicity", *Diabetes Care*, 1990, pp. 610-630, vol. 13(6).

Rossetti et al., "Correction of Hyperglycemia with Phlorizin Normalizes Tissue sensitivity to Insulin in Diabetic Rats", *J. Clin. Invest.*, 1987, pp. 1510-1515, vol. 79.

(56) References Cited

OTHER PUBLICATIONS

Rossetti et al., "Effect of Chronic Hyperglycemia on in Vivo Insulin Secretion in Partially Pancreatectomized Rats", *J. Clin Invest.*, 1987, pp. 1037-1044, vol. 80.

Kahn et al., "Normalization of blood glucose in diabetic rats with phlorizin treatment reverses insulin-resistant glucose transport in adipose cells without restoring glucose transporter gene expression", *J. Clin. Invest.*, 1991, pp. 561-570, vol. 87.

Tsujihara. et al., "Na+-Glucose Cotransporter (SGLT) Inhibitors as Antidiabetic Agents. 4. Synthesis and Pharmacological Properties of 4'-Dehydroxyphlorizin Derivatives Substituted on the B Ring", *J. Med. Chem.*, 1999, pp. 5311-5324, vol. 42(2).

Arakawa, et al., Improved diabetic syndrome in C57BL/Ks-db/db mice by oral administration of the Na+-glucose cotransporter inhibitor T-1095, *Br. J. Pharmacol.*, 2001, pp. 578-586, vol. 132(2).

Ueta et al., "Long-term treatment with the Na+-glucose cotransporter inhibitor T-1095 causes sustained improvement in hyperglycemia and prevents diabetic neuropathy in Goto-kakizaki Rats", *Life Sciences*, 2005, pp. 2655-2668, vol. 76.

Mongin et al., "Deprotonation of furans using lithium magnesates", *Tetrahedron Lett.*, 2005, pp. 7989-7992, vol. 46.

Kitagawa et al., "Halogen—Magnesium Exchange via Trialkylmagnesates for the Preparation of Aryl- and Alkenylmagnesium Reagents", *Angew. Chem. Int. Ed.*, 2000, pp. 2481-2493, vol. 39(14).

Knochel et al., *Organic Reactions*, vol. 58, Chapter 2: Preparation and Application of Functionalized Organozinc Compounds by., pp. 417-490, Edited by L. E. Overman, et al., John Wiley &Sons, Inc., Publishers.

International Search Report relating to International Patent Application No. PCT/US2010/052598. Date of Mailing of International Search Report: Jan. 12, 2011.

Written Opinion of the International Searching Authority relating to International Patent Application No. PCT/US2010/052598. Date of Mailing of Written Opinion: Jan. 12, 2011.

Ahmad et al., "Synthesis and Structure Determination of Some Oxadiazole-2-Thione and Triazole-3-Thione Galactosides.", *Nucleosides, Nucleotides & Nucleic Acids*, 2001, pp. 1671-1682, vol. 20(9).

Greene et al., "Protective Groups in Organic Synthesis.", 3rd Edition, 1999, pp. 119-121, XP002670712.

Hongu et al., "Na+-Glucose Cotransporter Inhibitors as Antidiabetic Agents. II. [1] Synthesis and Structure—Activity Relationships of 4'-Dehydroxyphlorizin Derivatives.", *Chem. Pharm. Bull.*, 1998, pp. 22-23, vol. 46(1).

Klapars et al., "Copper-Catalyzed Halogen Exchange in Aryl Halides: An Aromatic Finkelstein Reaction", *J. Am. Chem. Soc.*, 2002, pp. 14844-14845, vol. 124(50).

Maatooq et al., "C-p-Hydroxybenzoylglycoflavones From *Citrullus colocynthis*.", *Phytochemistry*, Jan. 1997, pp. 187-190, vol. 44(1).

Polshettiwar et al., "Pd-N-heterocycle carbene (NHR) organic silica: synthesis and application in carbon-carbon coupling reactions.", *Tetrahedron*, May 12, 2008, pp. 4637-4643, vol. 64(20), Elsevier Science Publishers, Amsterdam, NL, XP022607642.

Srogl et al., "Sulfonium salts. Participants par excellence in metal-catalyzed carbon-carbon bond-forming reactions.", Journal of the American Chemical Society, Jan. 1, 1997, pp. 12376-12377, vol. 119, American Chemical Society, US, XP002955770.

Zamani et al., "Synthesis and Structure Determination of Some New N-Glycosides of 4,5-Disubstituted-1,2,4-triazole-3-thiones.", *Journal of the Chinese Chemical Society*, 2002, pp. 1041-1044, vol. 49.

Translation—Zhdanov, Y. et al., "Application of organozinc compounds in the synthesis of carbon-carbon derivatives of sugars.", Database CA (online), Chemical Abstracts Service, Columbus, Ohio, USA, XP002612365.

Adachi et al., "T-1095, a Renal Na+-Glucose Transporter Inhibitor, Improves Hyperglycemia in Streptozotocin-Induced Diabetic Rats.", *Metabolism*, Aug. 2000, pp. 990-995, vol. 49(8).

Albertoni Borghese et al., "Inhibitors of sodium/glucose cotransport.", Drugs of the Future, Apr. 2009, pp. 297-305, vol. 34(4), Prous Science, XP007915342.

Amishiro et al., "Synthesis and Antitumor Activity of Duocarmycin Derivatives: A-Ring Pyrrole Compounds Bearing 5-Membered Heteroarylacryloyl Groups," Chem. Pharm. Bull., Oct. 1999, pp. 1393-1403, vol. 47(10).

Appleton et al., "A Mild and Selective C-3 Reductive Alkylation of Indoles", Tetrahedron Letters, 1993, pp. 1529-1532, vol. 34(9).

Apsel et al., "General Entries to *C*-aryl glycosides. Formal synthesis of galtamycinone.", Tetrahedron Letters, 2003, pp. 1075-1077, vol. 44.

Banker, Modern Pharmaceutics, Third Edition, Marcel Dekker, Inc., published 1996, p. 596.

Beck-Nielsen et al., "In Vivo Glucose Metabolism, Insulin Secretion and, Insulin Action in Europids with non-insulin-dependent Diabetes mellitus (NIDDM) and Their First-degree Relatives.", Diabetic Medicine, Sep. 1996, pp. S78-S84, vol. 13(9 Supp. 6).

Benhaddou et al.,"Tetra-n-propylammonium tetra-oxoruthenate(VII): a reagent of choice for the oxidation of diversely protected glycopyranoses and glycofuranoses to lactones", Carbohydrate Research, 1994, pp. 243-250, vol. 260.

Bertolini et al., "A New Simple One-Pot Regioselective Preparation of Mixed Diesters of Carbonic Acid.", Journal of Organic Chemistry, 1998, pp. 6031-6034, vol. 63(17).

Blair et al., "Effect of Ring Fluorination on the Pharmacology of Hallucinogenic Tryptamines", J. Med. Chem., 2000, pp. 4701-4710, vol. 43.

Boehm et al., "Novel Inhibitors of DNA Gyrase: 3D Structure Based Biased Needle Screening, Hit Validation by Biophysical Methods, and 3D Guided Optimization. A Promising Alternative to Random Screening," J. Med. Chem., 2000, pp. 2664-2674, vol. 43(14).

Bookser, B.C., "2-Benzyloxymethyl-5-(tributylstannyptetrazole. A reagent for the preparation of 5-aryl-and 5-heteroaryl-1H-tetrazoles via the Stille reaction," Tetrahedron Letters, 2000, pp. 2805-2809, vol. 41.

Bouillon et al., "Synthesis of novel halopyridinylboronic acids and esters. Part 2: 2,4, or 5-Halopyridin-3-yl-boronic acids and esters," Tetrahedron, 2002, pp. 3323-3328, vol. 58.

Bouillon et al., "Synthesis of novel halopyridinylboronic acids and esters. Part 3: 2, or 3-Halopyridin-4-yl-boronic acids and esters," Tetrahedron, 2002, pp. 4369-4373, vol. 58.

Bouillon et al., "Synthesis of novel halopyridinylboronic acids and esters. Part 4: Halopyridin-2-yl-boronic acids and esters are stable, crystalline partners for classical Suzuki cross-coupling," Tetrahedron, 2003, pp. 10043-10049, vol. 59.

Brooks et al., "Boron Trichloride/Tetra-n-Butylammonium Iodide: A Mild, Selective Combination Reagent for the Cleavage of Primary Alkyl Aryl Ethers", J. Org. Chem., 1999, pp. 9719-9721, vol. 64.

CAS Reg. No. 487001-40-1, IPOrganisers, Entered STN Feb. 7, 2003, pp. 1-2.

Caumo et al., "Insulin Sensitivity from Meal Tolerance Tests in Normal Subjects: A Minimal Model Index.", J. of Clinical Endocrinology & Metabolism, 2000, pp. 4396-4402, vol. 85(11).

Cicchillo et al., "A convenient synthesis of glycosyl chlorides from sugar hemiacetals using triphosgene as the chlorine source, " Carbohydrate Research, 2000, pp. 431-434, vol. 328.

Clayden et al., "Dearomatizing Cyclization of Arylsulfonylalkoxymethyl Lithiums: A Route to the Podophyllotoxin Skeleton," Organic Letters, 2003, pp. 831-834, vol. 5(6).

Comins et al., "Synthesis of 3-Substituted Indoles Via N-Acylindolium Ions", Tetrahedron Letters, 1986, pp. 1869-1872, vol. 27(17).

Cottet et al., "Recommendable Routes to Trifluoromethyl-Substituted Pyridine—and Quinolinecarboxylic Acids," Eur. J. Org. Chem., 2003, pp. 1559-1568.

Czernecki et al., "C-Glycosides. 7. Stereospecific C-Glycosylation of Aromatic and Heterocyclic Rings", J. Org. Chem., 1989, pp. 610-612, vol. 54.

De Las Heras et al., "Alkylating Nucleosides 1. Synthesis and Cytostatic Activity of N-Glycosyl(halomethyl)-1,2,3-triazoles. A New Type of Alkylating Agent," Journal of Medicinal Chemistry, 1979,pp. 496-501, vol. 22(5).

(56) References Cited

OTHER PUBLICATIONS

Deeg et al., "Pioglitazone and Rosiglitazone Have Different Effects on Serum Lipoprotein Particle Concentrations and Sizes in Patients With Type 2 Diabetes and Dyslipidemia.", Diabetes Care, Oct. 2007, pp. 2458-2464, vol. 30(10).
Deetjen et al., "Renal Handling of D-Glucose and Other Sugars", Textbook of Nephrology, 3rd Edition, 1995, pp. 90-94. vol. 1.
Devivar et al., "Benzimidazole Ribonucleosides: Design, Synthesis, and Antiviral Activity of Certain 2-(Alkylthio)- and 2-(Benzylthio)-5,6-dichloro-1-(.beta.-D-ribofuranosyl)benzimidazolesl.", J.Med. Chem., 1994, pp. 2942-2949, vol. 37.
Dewynter et al., "Synthesis of Pseudomucleosides containing Chiral Sulfahydantoins as Aglycone (II)", Tetrahedron, 1996, pp. 993-1004, vol. 52(3).
Dillard et al., "Indole Inhibitors of Human Nonpancreatic Secretory Phospholipase A2. 1. Indole-3-acetamides", J. Med. Chem., 1996, pp. 5119-5136, vol. 39.
Dinneen, S.F., "The Postprandial State: Mechanisms of Glucose Intolerance.", Diabetic Medicine, Aug. 1997, pp. S19-S24, vol. 14, Issue S3.
Dondoni et al., "Stereoselective synthesis of C-glycosylphosphonates from their ketols. Reconsideration of an abandoned route", Tetrahedron: Asymmetry, 2000, pp. 305-317, vol. 11.
Dondoni et al., "Thiazole-Based Synthesis of Formyl C-Glycosides", J. Org. Chem., 1994, pp. 6404-6412, vol. 59.
Dudash et al., "Glycosylated dihydrochalcones as potent and selective sodium glucose co-transporter 2 (SGLT2) inhibitors," Bioorganic & Medicinal Chemistry Letters, 2004, pp. 5121-2125, vol. 14.
Dunn et al., "Analgetic and antiinflammatory 7-Aroylbenzofuran-5-ylacetic acids and 7-Aroylbenzothiophene-5-ylacetic Acids.", Journal of Med. Chem., 1986, pp. 2326-2329, vol. 29(1).
Eid et al., "Reaction of Some 1,2,4-Triazines with Acetobromoglucose", Arch. Pharm (Weinheim), 1990, pp. 243-245, vol. 323.
Ellsworth et al., " Aglycone exploration of C-arylglucoside inhibitors of renal sodium-dependent glucose transporter SGLT2," Bioorganic & Medicinal Chemistry Letters, 2008, pp. 4770-4773, vol. 18.
Ellsworth et al., "C-Arylglucoside synthesis: triisopropylsilane as a selective reagent for the reduction of an anomeric C-phenyl ketal," Tetrahedron: Asymmetry, 2003, pp. 3243-3247, vol. 14.
Emancipator, K., "Laboratory diagnosis and monitoring of diabetes mellitus.", Am J Clin Pathol., Nov. 1999, pp. 65-674, vol. 112(5).
Frahn et al., "Functionalized AB-Type Monomers for Suzuki Polycondensation," Synthesis, Nov. 1997, pp. 1301-1304.
Fresneda et al., "Synthesis of the indole alkaloids meridianins from the tunicate Aplidium meridianum" Tetrahedron, 2001, pp. 2355-2363, vol. 57.
Fuller et al., "Thienothiophenes. Part 2. Synthesis, metallation and bromine-lithium exchange reactions of thieno[3,2-b-thiophene and its polybromo derivatives," J. Chem. Soc., Perkin Trans. 1., 1997, pp. 3465-3470.
Ganesh et al., "Synthesis and biological evaluation of fluorescently labeled epothilone analogs for tubulin binding studies," Tetrahedron, 2003, pp. 9979-9984, vol. 59.
Gershell, L., "Type 2 diabetes market", Nature Reviews Drug Discovery, May 2005, pp. 367-368, vol. 4.
Gohier et al., "ortho-Metalation of Unprotected 3-Bromo and 3-Chlorobenzoic Acids with Hindered Lithium Dialkylamides," J. Org. Chem., 2003, pp. 2030-2033, vol. 68.
Goldberg R.B., "Prevention of Type 2 Diabetes.", Medical Clinics of North America, Jul. 1998, pp. 805-821, vol. 82(4).
Goodman & Gilman's the Pharmacological Basis of Therapeutics, 10th Edition, McGraw-Hill Medical Publishing Division, 2001, pp. 54-57.
Gronowitz et al., "Some Substitution Reactions of 1-(2-Thienyl)pyrazole and 1-(3'-Thienyl)pyrazole," Chemica Scripta., 1979, pp. 157-161, vol. 13.

Groop et al., "Characterization of the Prediabetic State.", American Journal of Hypertension, Sep. 1997, pp. 172S-180S, vol. 10(9Part2).
Gros et al., "Efficient and Regioselective Access to Bis-heterocycles via Palladium-Catalysed Coupling of Organostannanes and Organozincates Derived from C-6 Lithiated 2-Methoxypyridine," Synthesis, 1999, pp. 754-756, No. 5.
Haffner S.M., "Impaired Glucose Tolerance, Insulin Resistance and Cardiovascular Disease.", Diabetic Medicine, Aug. 1997, pp. S12-S18, vol. 14.
Haffner S.M., "The Prediabetic Problem: Development of Non-Insulin-Dependent Diabetes Mellitus and Related Abnormalities.", Journal of Diabetes and Its Complications, Mar.-Apr. 1997, pp. 69-76, vol. 11(2).
Han et al., "Dapagliflozin, a Selective SGLT2 Inhibitor, Improves Glucose Homeostasis in Normal and Diabetic Rats", Diabetes, Jun. 2008, pp. 1723-1729, vol. 57, New York.
Handlon, A. L., "Sodium glucose co-transporter 2 (SGLT2) inhibitors as potential antidiabetic agents," Expert Opin. Ther. Patents, 2005, pp. 1531-1540, vol. 15(11).
Hixon et al., "Sizing Materials by Crushing and Grinding.", Chemical Engineer, Nov. 1990, pp. 94-103.
Hofslokken et al., "Convenient Method for the ortho-Formylation of Phenols.", Acta Chemica Scandinavica, 1999, pp. 258-262, vol. 53.
Horton et al., "Synthetic Routes to Higher-Carbon Sugars. Reaction of Lactones with 2-Lithio-1,3-Dithiane", Carbohydrate Research, 1981, pp. 27-41, vol. 94.
Hu et al., "A New Approach Towards the Yellowing Inhibition of Mechanical Pulps. Part I: Selective Removal of alpha-Hydroxyl and alpha-Carbonyl Groups in Lignin Model Compounds", Holzforschung, 1999, pp. 43-48, vol. 53(1).
Huang-Minlon, "Reduction of Steroid Ketones and other Carbonyl Compounds by Modified Wolff-Kishner Method", J. Am. Chem. Soc., Oct. 1949, pp. 3301-3303, vol. 71.
Ibrahim et al., "Facile Approach for the Selective Glycodisation of Cyclic Asymmetric Amides and Thioamides", Carbohydrate Letters, 1996, pp. 425-432, vol. 1.
Ibrahim et al., "Selective Synthesis and Structure of 2-N- and 3-S-Glucosyl-1,2,4-Triazoles of Potential Biological Interest", Carbohydrate Letters, 1999, pp. 331-338, vol. 3(5).
Idris et al., "Sodium-glucose co-transporter-2 inhibitors: an emerging new class of oral antidiabetic drug.", Diabetes, Obesity and Metabolism, 2009, pp. 79-88, vol. 11(2), GB, XP007915350.
Isaji, M., "Sodium-glucose cotransporter inhibitor for diabetes," Current Opinion in Investigational Drugs, 2007, pp. 285-292, vol. 8(4).
Kaelin et al., "General Strategies for the Synthesis of the Major Classes of C-aryl Glycosides.", J. Am. Chem. Soc., 2001, pp. 6937-6938, vol. 123.
Kanai et al., "The Human Kidney Low Affinity Na+/Glucose Cotransporter SGLT2: Delineation of the Major Renal Reabsorptive Mechanism for D-Glucose", J. Clin. Invest., Jan. 1994, pp. 397-404, vol. 93.
Kasahara et al., "A missense mutation in the Na+/glucose cotransporter gene SGLT1 in a patient with congenital glucose-galactose malabsorption: normal trafficking but inactivation of the mutant protein," Biochimica et Biophysics Acta, 2001, pp. 141-147, vol. 1536.
Katz et al., "Quantitative Insulin Sensitivity Check Index: A Simple, Accurate Method for Assessing Insulin Sensitivity in Humans.", J. of Clin. Endocrinology & Metabolism, 2000, pp. 2040-2410, vol. 85(7).
Ketcha et al., "Synthesis of Alyl-Substituted N-Protected Indoles via Acylation and Reductive Deoxygenation1" J. Org. Chem., 1989, pp. 4350-4356, vol. 54.
Khan et al, "Reactions of Phenyl-Substituted Heterocyclic Compounds—II. Nitrations and Brominations of 1-Phenylpyrazole Derivatives," Canadian Journal of Chemistry, 1963, pp. 1540-1547, vol. 41.
Lee et al., "Synthesis and in Vitro Activity of Novel Isoxazolyl Tetrahydropyridinyl Oxazolidinone Antibacterial Agents," Bioorganic & Medicinal Chemistry Letters, 2003, pp. 4117-4120, vol. 13.
Lee et al., "Recent Advances in Aryl C-Glycoside Synthesis.", Current Topics in Medicinal Chemistry, 2005, pp. 1333-1350, vol. 5.

(56) References Cited

OTHER PUBLICATIONS

Lin et al., "Syntheses of Guanidinoglycosides with the Inventive use of Mitsunobu Conditions and 1, 8-Diazabicyclo[5.4.0]undec-7-ene.", Synthesis, 2003, pp. 255-261, No. 2.
Link et al., "A method for preparing C-glycosides related to phlorizin" Tetrahedron Letters, 2000, pp. 9213-9217, vol. 41.
Lipscombe et al., "Trends in diabetes prevalence, incidence, and mortality in Ontario, Canada 1995-2005: a population-based study", Lancet, 2007, vol. 369, pp. 750-756.
Mackenzie et al., "Biophysical Characteristics of the Pig Kidney Na+/Glucose Cotransporter SGLT2 Reveal a Common Mechanism for SGLT1 and SGLT2", J. Biol. Chem., 1996, vol. 271, pp. 32678-32683, No. 5.
Manis et al., "Metabolism of 4,4'-Methylenebis(2-chloroaniline) by Canine Liver and Kidney Slices.", Drug Metabolism and Disposition, 1986, pp. 166-174, vol. 14(2).
Marsenic, O. MD, "Glucose Control by the Kidney: An Emerging Target in Diabetes.", Am. J. of Kidney Diseases, May 2009, pp. 875-883, vol. 53(5).
Martin, S. F., "Unified Strategy for the Synthesis of C-aryl glycosides*.", Pure Appl. Chem., 2003, pp. 63-70, vol. 75(1).
Matsuda et al., "Insulin Sensitivity Indices Obtained From Oral Glucose Tolerance Testing: Comparison with the euglycemic insulin clamp," Diabetes Care, Sep. 1999, pp. 1462-1470, vol. 22(9).
Matthews et al., "Homeostasis model assessment: insulin resistance and—cell function from fasting plasma glucose and insulin concentrations in man," Diabetolgia, 1985, pp. 412-419, vol. 28.
Meanwell et al., "Regiospecific Functionalization of 1,3-Dihydro-2H-benzimidazol-2-one and Structurally Related Cyclic Urea Derivates.", J. Org. Chemistry, 1995, pp. 1565-1582, vol. 60(6).
Meng et al., "Discovery of Dapagliflozin: a Potent, Selective Renal Sodium-Dependent Glucose Cotransporter 2 (SGLT2) Inhibitor for the Treatment of Type 2 Diabetes", J. Med. Chem., 2008, pp. 1145-1149, vol. 51(5).
Messaoudi et al, "Synthesis and biological evaluation of oxindoles and benzimidazolinones derivatives," European Journal of Medicinal Chemistry, 2004,pp. 453-458, vol. 39.
Mewshaw et al., "New Generation Dopaminergic Agents. 7. Heterocyclic Bioisosteres that Exploit the 3-Oh-Phenoxyethylamine D2 Template", Bioorganic & Medicinal Chemistry Letters, 1999, pp. 2593-2598, vol. 9.
Miyaura et al., "Palladium-Catalyzed Cross-Coupling Reactions of Organoboron Compounds.", Chem. Rev., 1995, pp. 2457-2583, vol. 95(7).
Nishimura et al, "Tissue-specific mRNA Expression Profiles of Human ATP-binding Cassette and Solute Carrier Transporter Superfamilies," Drug Metab. Pharmacokinet., 2005, pp. 452-477, vol. 20(6).
Nomura et al., "Discovery of canagliflozin, a novel C-glucoside with thiophene ring, as sodium dependent glucose cotransporter 2 inhibitor for the treatment of type 2 diabetes mellitus.", Journal of Med. Chem., Sep. 9, 2012, pp. 6355-6360, vol. 53(17), American Chemical Society, US, XP007915324.
Nomura, S., "Renal Sodium-Dependent Glucose Cotransporter 2 (SGLT2) Inhibitors for New Anti-Diabetic Agent," Current Topics in Medicinal Chemistry, 2010, pp. 411-418, vol. 10(4).
Ohsumi et al. "Pyrazole-O-Glucosides as Novel Na+-Glucose Cotransporter (SGLT) Inhibitors" Bioorganic & Medicinal Chemistry Letters, 2003, pp. 2269-2272, vol. 13.
Oku et al., "T-1095, an Inhibitor of Renal Na+-Glucose Cotransporters, May Provide a Novel Approach to Treating Diabetes", Diabetes, Sep. 1999, pp. 1794-1800, vol. 48.
Orjales et al. "New 2-Piperazinylbenzimidazole Derivatives as 5-HT-3 Antagonists. Synthesis and Pharmacological Evaluation," J. Med. Chem., 1997, pp. 586-593, vol. 40.
Parker et al., "Reductive Aromatization of Quinols: Synthesis of the C-Arylglycoside Nucleus of the Paulacandins and Chaetiacandin," Organic Letters, 2000, pp. 497-499, vol. 2(4).
Parrott, E.L., "Milling of pharmaceutical solids.", Journal of Pharmaceutical Sciences, Jun. 1974, pp. 813-829, vol. 63(6).
Patani et al., "Bioisosterism: A Rational Approach in Drug Design", Chem. Rev., American Chemical Society, 1996, pp. 3147-3176, vol. 96.
Peng et al., "Post-transcriptional Regulaton of Na+/Glucose Cotransporter (SGTL1) Gene Expression in LLC-PK1 Cells.", Journal of Biological Chemistry, 1995, pp. 20536-20542, vol. 270(35).
Perry's Chemical Engineers Handbook, Sixth Edition, 1984, pp. 21-13 to 21-19.
Pharmaceutical Sciences, Remington, 17th Ed., pp. 1585-1594 (1985).
Ramlo-Halsted B.A. & Edelman S.V., "The Natural History of Type 2 Diabetes Mellitus: Implications for Clinical Practice.", Primary Care, Dec. 1999, pp. 771-789, vol. 26(4).
Raynaud et al., "Revised Concept for the Estimation of Insulin Sensitivity From a Single Sample.", Diabetes Care, Jun. 1999, pp. 1003-1004, vol. 22(6).
Rosenstock et al., "Canagliflozin, an Inhibitor of Sodium Glucose Co-Transporter 2 (SGLT2), Improves Glycemic Control and Lowers Body Weight in Subjects with Type 2 Diabetes (T2D) on Metformin.", Diabetes, Jun. 1, 2010, pp. A21, vol. 59(supp. 1), American Diabetes Association, US, XP009139979.
Schmidt et al., "Synthese von Pyrazol-, Pyrazolo[3,4-d]pyrimidin- und 1H-1,2,4-Triazolgluconucleosiden aus Glucosehydrazonen," Liebigs Ann. Chem., 1981, pp. 2309-2317.
Schultheiss et al., "Pharmaceutical Cocrystals and Their Physicochemical Properties.", Crystal Growth and Design, Jun. 3, 2009, pp. 2950-2967, vol. 9(6), XP55011939.
Shan et al., "The role of cocrystals in pharmaceutical science.", Drug Discovery Today, May 1, 2008, pp. 440-446, vol. 13(9-10), Elsevier, Rahway, NJ,US, XP022649919.
Silverman, R. B., "The Organic Chemistry of Drug Design and Drug Action," Academic Press, 1992, pp. 19-23.
Somei et al., "The First and Simple Total Synthesis of Cappariloside Al," Heterocycles, 2000, pp. 1573-1578, vol. 53(7).
Stoner et al., "Benzylation via Tandem Grignard Reaction— Lodotrimethylsilane (TMSI) Mediated.Reduction," Tetrahedron, 1995, pp. 11043-11062, vol. 51(41).
Stumvoll et al., "Use of the Oral Glucose Tolerance Test to Assess Insulin Release and Insulin Sensitivity.", Diabetes Care, Mar. 2000, pp. 295-301, vol. 23(3).
Tanaka et al. "Solid-Phase Synthesis of—Mono-Substituted Ketones and an Application to the Synthesis of a Library of Phlorizin Derivatives", Synlett, 2002, pp. 1427-1430, No. 9.
Thornber, C.T., "Isosterism and Molecular Modification in Drug Design.", Chem. Society Review, 1979, pp. 563-580, vol. 8.
Tilak et al, "Carcinogenesis by Thiophene Isosters of Polycyclic Hydrocarbons," Tetrahedron, 1960, pp. 76-95, vol. 9.
Tsujihara et al., Bio Clinica, 1998, pp. 324-328, vol. 13(4), English language Abstract.
Turk et al., "Glucose/galactose malabsorption caused by a defect in the Na+/glucose cotransporter," Nature, Mar. 1991, pp. 354-356, vol. 350.
Vishweshwar et al., "Pharmaceutical co-crystals.", Journal of Pharmaceutical Sciences, Mar. 1, 2006, pp. 499-516, vol. 95(3), American Pharmaceutical Association, Washington, US.
Wallace et al., "Use and Abuse of Homa Modeling.", Diabetes Care, Jun. 2004, pp. 1487-1495, vol. 27(6).
Wang et al, "Selective monolithiation of 2,5-dibromopyridine with butyllithium," Tetrahedron Letters, 2000, pp. 4335-4338, vol. 41.
Wareham et al., "Is There Really an epidemic of diabetes?", Diabetologia, 2005, pp. 1454-1455, vol. 48.
Washburn, W. N., "Evolution of sodium glucose co-transporter 2 inhibitors as anti-diabetic agents," Expert Opin. Ther. Patents, 2009, pp. 1485-1499, vol. 19(11).
Wild et al., "Global Prevalence of Diabetes: Estimates for the year 2000 and projections for 2030," Diabetes Care, May 2004, pp. 1047-1053, vol. 27(5).
Wolff, M. E., vol. 1: Principles and Practice, Burger's Medicinal Chemistry and Drug Discovery, 5th Edition, 1995, pp. 975-977.
Wright, E.M., "Renal Na+-glucose cotransporters," Am J Physiol Renal Physiol, 2001, pp. F10-F18, vol. 280.

(56) References Cited

OTHER PUBLICATIONS

Wurster D.E., "Air-suspension Technique of Coating Drug Particles* A Preliminary Report.", Journal of the American Pharmaceutical Association, Aug. 1959, pp. 451-454, vol. 48(8).

Wurster, D.E., "Preparation of compressed tablet granulations by the air-suspension technique II.", Journal of the American Pharmaceutical Association, 1960, pp. 82-84, vol. 49(2).

Yang et al., "Convergent C-Glycolipid Synthesis via the Ramberg-Backlund Reaction: Active Antiproliferative Glycolipids", Org. Lett. 1999, pp. 2149-2151, vol. 1913).

Yoshimura et al., "Discovery of Novel and PotenCRetinoic Acid Receptor alpha—Agonists: Synthesis and Evaluation of Benzofuranyl-pyrrole and Benzothiophenyl-pyrrole Derivatives," J. Med. Chem., 2000, pp. 2929-2937, vol. 43.

Zhou, F. Y., "The Synthesis and Characterization of 1-Benzyl-3-N-(Beta-D-glucosie-1-yl)-4-fluorouracil", Hecheng Huaxue, 2001, pp. 272-274, vol. 9(3).

Greene et al., "Protective Groups in Organic Synthesis.", 3rd Edition, 1999, pp. 116-121.

Gong, H., et al., "Diastereoselective Ni-Catalyzed Negishi Cross-Coupling Approach to Saturated, Fully Oxygenated C-Alkyl and C-Aryl Glycosides.", Journal of the American Chemical Society, Sep. 10, 2008, pp. 12177-12183, vol. 130(36), XP002612364.

Zhdanov, Y. et al., "Application of organozinc compounds in the synthesis of carbon-carbon derivatives of sugars.", Database CA (online), Chemical Abstracts Service, Columbus, Ohio, USA, XP002612365.

Byrn et al., "Pharmaceutical Solids: A Strategic Approach to Regulatory Considerations.", Pharml. Res., 1995, pp. 945-954, vol. 12(7).

Bavin, M., "Process Development: Polymorphism in Process Development.", Chemistry & Industry, 1989, pp. 527-529, vol. 16.

Jianqun, et al., "Recent advances in palladium catalysts for aryl chlorides coupling reaction", Industrial Catalysis, Jul. 31, 2005, pp. 29-44, vol. 13(7).

Asahara et al., Handbook of Solvents., K.K. Kodansha., Sep. 1, 1985, Sixth Printing, pp. 47-51, Tokyo, JP.

Kozikowski et al., "Organometallics in Organic Synthesis. Applications of a New Diorganozinc Reaction to the Synthesis of C-Glycosyl Compounds With Evidence for an Oxonium-Ion Mechanism*.", Carbohydrate Research, 1987, pp. 109-124, vol. 171.

Zhiyin, et al., "Cross-coupling reaction of Grignard reagent with thiophenyl halides by using nickel phosphine as catalyst and the synthesis of α-terthienyl", Huaxue Shiji, Dec. 31, 1995, pp. 289-290, vol. 17(5).

Brandsma et al., "Nickel- and Palladium-Catalyzed Cross-Coupling Reactions With Organometallic Intermediates", Application of Transition Metal Catalysts in Organic Synthesis, 1999, Chapter 11, pp. 227-230, 243-246, 250-252, 258, 261, 273, Springer-Verlag Berlin Heidelberg, Germany.

Kravovskiy et al., "A LiCl-Mediated Br/Mg—exchange reaction for preparing functionalized aryl and heteroarylymagnesium connections starting from organic bromides.", Angew. Chem., 2004, pp. 3396-3399, vol. 116, Translation Provided.

Kravovskiy et al., "Highly efficient reagents for the bromine-magnesium exchange.", Angew. Chem., 2006, pp. 165-169, vol. 118, Translation Provided.

Knochel, P., et al., Organic Reactions, vol. 58, Chapter 2: Preparation and Application of Functionalized Organozinc Compounds., 2001, pp. 417-490, Edited by L. E. Overman, et al., John Wiley &Sons, Inc., Publishers.

* cited by examiner

PROCESS FOR THE PREPARATION OF COMPOUNDS USEFUL AS INHIBITORS OF SGLT2

CROSS REFERENCE TO RELATED APPLICATIONS

This application claims the benefit of U.S. Provisional Application 61/251,378, filed on Oct. 14, 2009, which is incorporated by reference herein in its entirety.

FIELD OF THE INVENTION

The present invention is directed to a novel process for the preparation of compounds having inhibitory activity against sodium-dependent glucose transporter (SGLT) being present in the intestine or kidney.

BACKGROUND OF THE INVENTION

Diet therapy and exercise therapy are essential in the treatment of diabetes mellitus. When these therapies do not sufficiently control the conditions of patients, insulin or an oral antidiabetic agent is additionally used for the treatment of diabetes. At the present, there have been used as an antidiabetic agent biguanide compounds, sulfonylurea compounds, insulin resistance improving agents and α-glucosidase inhibitors. However, these antidiabetic agents have various side effects. For example, biguanide compounds cause lactic acidosis, sulfonylurea compounds cause significant hypoglycemia, insulin resistance improving agents cause edema and heart failure, and α-glucosidase inhibitors cause abdominal bloating and diarrhea. Under such circumstances, it has been desired to develop novel drugs for treatment of diabetes mellitus having no such side effects.

Recently, it has been reported that hyperglycemia participates in the onset and progressive impairment of diabetes mellitus, i.e., glucose toxicity theory. Namely, chronic hyperglycemia leads to decrease of insulin secretion and further to decrease of insulin sensitivity, and as a result, the blood glucose concentration is increased so that diabetes mellitus is self-exacerbated (Unger, R. H., et al., "Hyperglycemia as an Inducer as well as a Consequence of Impaired Islet Cell Function and Insulin Resistance: Implications for the Management of Diabetes", *Diabetologia*, vol. 28, issue 3, pp. 119-121 (1985); Rossetti, L. et al., "Glucose Toxicity", *Diabetes Care*, vol. 13, issue 6, pp. 610-630 (1990)). Therefore, by treating hyperglycemia, the aforementioned self-exacerbating cycle is interrupted so that the prophylaxis or treatment of diabetes mellitus is made possible.

As one of the methods for treating hyperglycemia, it is considered to excrete an excess amount of glucose directly into urine so that the blood glucose concentration is normalized. For example, by inhibiting sodium-dependent glucose transporter being present at the proximal convoluted tubule of kidney, the re-absorption of glucose at the kidney is inhibited, by which the excretion of glucose into urine is promoted so that the blood glucose level is decreased. In fact, it is confirmed that by continuous subcutaneous administration of phlorizin having SGLT inhibitory activity to diabetic animal models, hyperglycemia is normalized and the blood glucose level thereof can be kept normal for a long time so that the insulin secretion and insulin resistance are improved (Rossetti, L., et al., "Correction of Hyperglycemia with Phlorizin Normalizes Tissue sensitivity to Insulin in Diabetic Rats", *Journal of Clinical Investigation*, (1987), vol. 79, issue 5, pp. 1510-1515; Rossetti, L., et al., "Effect of Chronic Hyperglycemia on in vivo Insulin Secretion in Partially Pancreatectomized Rats", *Journal of Clinical Investigation*, (1987), vol. 80, issue 4, pp. 1037-1044; Kahn, B. B., et al., "Normalization of blood glucose in diabetic rats with phlorizin treatment reverses insulin-resistant glucose transport in adipose cells without restoring glucose transporter gene expression", *J. Clin. Invest.*, 1991, vol. 87, pp 561-570).

In addition, by treating diabetic animal models with SGLT inhibitory agents for a long time, insulin secretion response and insulin sensitivity of the animals are improved without incurring any adverse affects on the kidney or imbalance in blood levels of electrolytes, and as a result, the onset and progress of diabetic nephropathy and diabetic neuropathy are prevented (Kenji T., et al., "$Na^+$-Glucose Co-transporter (SGLT) Inhibitors as Antidiabetic Agents. 4. Synthesis and Pharmacological Properties of 4'-Dehydroxyphlorizin Derivatives Substituted on the B Ring", *J. Med. Chem.*, (1999), Vol. 42, pp. 5311-5324); Kenji A., et al., "Improved diabetic syndrome in C57BL/KsJ-db/db mice by oral administration of the $Na^+$-glucose cotransporter inhibitor T-1095", *British Journal of Pharmacology*, (2001), vol. 132, issue 2, pp. 578-586; Ueta, K., et al., "Long Term Treatment with the $Na^+$ Glucose Co-transporter Inhibitor T-1095 causes Sustained Improvement in Hyperglycemia and Prevents Diabetic Neuropathy in Goto-Kakizaki Rats", *Life Sci.*, (2005), vol. 76, issue 23, pp. 2655-2668)

From the above, SGLT inhibitors may be expected to improve insulin secretion and insulin resistance by decreasing the blood glucose level in diabetic patients and further prevent the onset and progress of diabetes mellitus and diabetic complications.

SUMMARY OF THE INVENTION

The present invention is directed to a process for the preparation of compounds of formula (I)

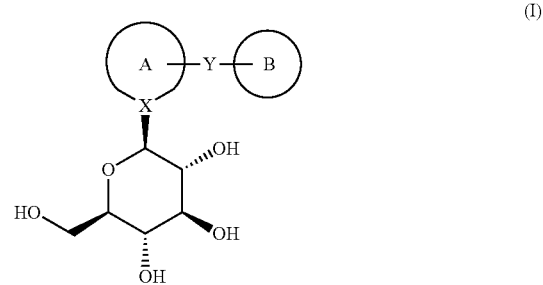

wherein Ring A and Ring B are one of the following:

(1) Ring A is an optionally substituted unsaturated monocyclic heterocyclic ring, and Ring B is an optionally substituted unsaturated monocyclic heterocyclic ring, an optionally substituted unsaturated fused heterobicyclic ring, or an optionally substituted benzene ring; or (2) Ring A is an optionally substituted benzene ring, and Ring B is an optionally substituted unsaturated monocyclic heterocyclic ring, or an optionally substituted unsaturated fused heterobicyclic ring wherein Y is linked to the heterocyclic ring of the fused heterobicyclic ring; or (3) Ring A is an optionally substituted unsaturated fused heterobicyclic ring, wherein the sugar moiety X-(sugar) and the moiety —Y-(Ring B) are both on the same heterocyclic ring of the fused heterobicyclic ring, and Ring B is an optionally substituted unsaturated monocyclic heterocyclic ring, an optionally substituted unsaturated fused heterobicyclic ring, or an optionally substituted benzene ring;

X is a carbon atom;

Y is —(CH$_2$)$_n$—; wherein n is 1 or 2;

provided that in Ring A, X is part of an unsaturated bond;

and pharmaceutically acceptable salts and solvates thereof;

comprising

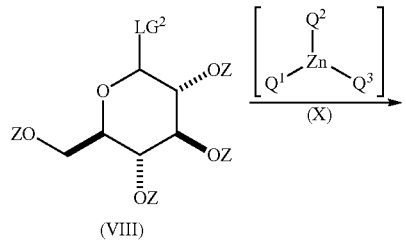

(VIII)

reacting a compound of formula (VIII), wherein each Z is an independently selected oxygen protecting group and LG$^2$ is a leaving group, with a compound of formula (X), wherein the compound of formula (X) is selected from the group consisting of (a) an organozinc derivative wherein Q$^1$ is

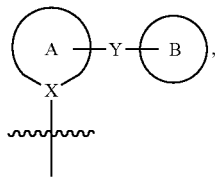

Q$^2$ is a halogen and Q$^3$ is absent;

(b) a di-substituted zinc derivative, wherein Q$^1$ and Q$^2$ are the same and are each

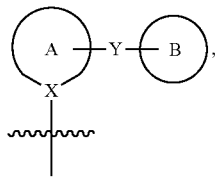

and Q$^3$ is absent;

(c) an organozincate derivative, wherein Q$^1$ is

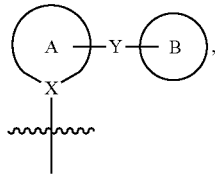

and Q$^2$ and Q$^3$ are each an independently selected non-transferrable group (wherein the zinc carries a negative charge and wherein the compound of formula (X) is present in conjunction with a counterion); and (d) an organozincate derivative, wherein Q$^1$, Q$^2$ and Q$^3$ are the same and are each

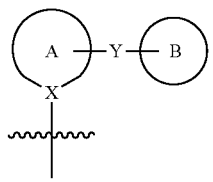

(wherein the zinc carries a negative charge and wherein the compound of formula (X) is present in conjunction with a counterion);

in an organic solvent or mixture of organic solvents; to yield the corresponding compound of formula (IX); and

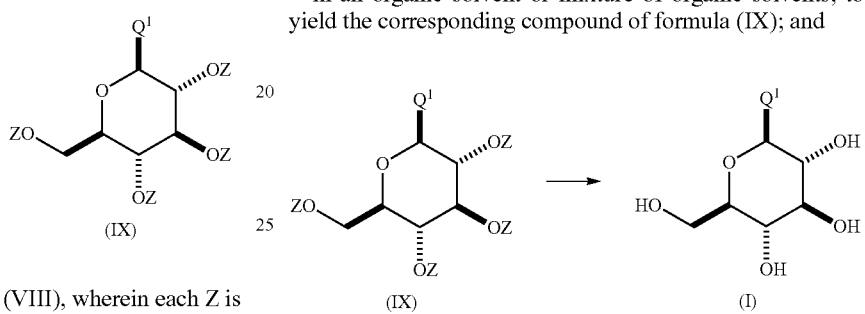

de-protecting the compound of formula (IX) to yield the corresponding compound of formula (I).

The present invention is further directed to a process for the preparation of compounds of formula (I)

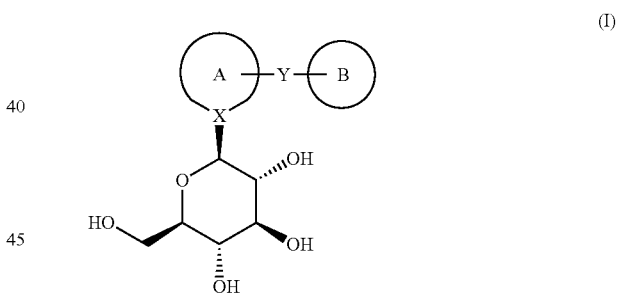

(I)

wherein Ring A and Ring B are one of the following:

(1) Ring A is an optionally substituted unsaturated monocyclic heterocyclic ring, and Ring B is an optionally substituted unsaturated monocyclic heterocyclic ring, an optionally substituted unsaturated fused heterobicyclic ring, or an optionally substituted benzene ring; or (2) Ring A is an optionally substituted benzene ring, and Ring B is an optionally substituted unsaturated monocyclic heterocyclic ring, or an optionally substituted unsaturated fused heterobicyclic ring wherein Y is linked to the heterocyclic ring of the fused heterobicyclic ring; or (3) Ring A is an optionally substituted unsaturated fused heterobicyclic ring, wherein the sugar moiety X-(sugar) and the moiety —Y-(Ring B) are both on the same heterocyclic ring of the fused heterobicyclic ring, and Ring B is an optionally substituted unsaturated monocyclic heterocyclic ring, an optionally substituted unsaturated fused heterobicyclic ring, or an optionally substituted benzene ring;

X is a carbon atom;
Y is —(CH$_2$)$_n$—; wherein n is 1 or 2;
provided that in Ring A, X is part of an unsaturated bond;
and pharmaceutically acceptable salts and solvates thereof;
comprising de-protecting the compound of formula (IX); to yield the corresponding compound of formula (I).

In an embodiment, the present invention is directed to a process for the preparation of a compound of formula (I-S)

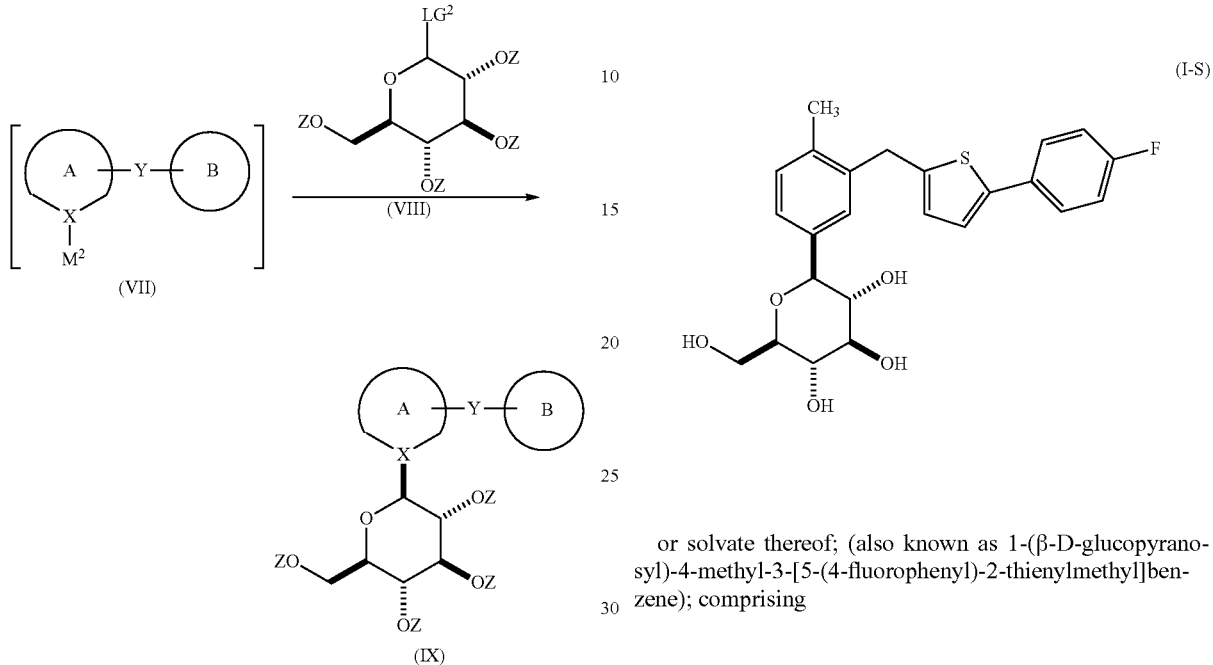

reacting a compound of formula (VII), wherein M$^2$ is a zinc species, with a compound of formula (VIII), wherein each Z is an independently selected oxygen protecting group and wherein LG$^2$ is a leaving group; in a mixture of an ether solvent and a hydrocarbon solvent; to yield the corresponding compound of formula (IX);

or solvate thereof; (also known as 1-(β-D-glucopyranosyl)-4-methyl-3-[5-(4-fluorophenyl)-2-thienylmethyl]benzene); comprising

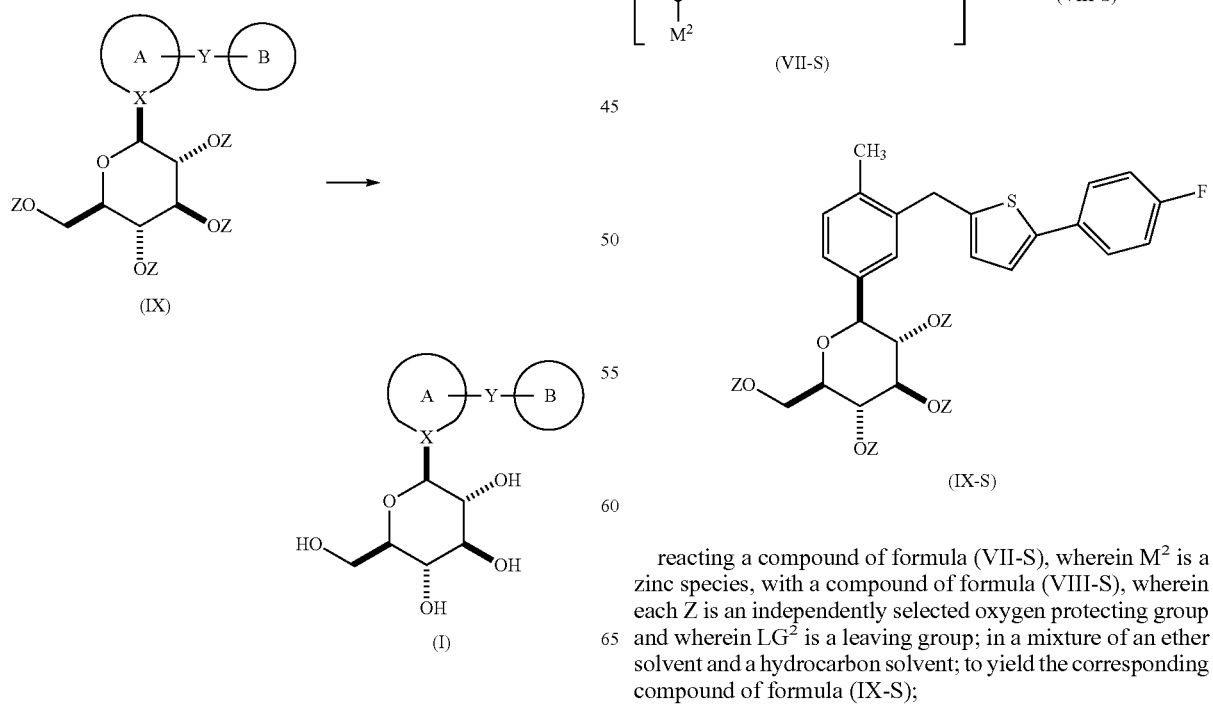

reacting a compound of formula (VII-S), wherein M$^2$ is a zinc species, with a compound of formula (VIII-S), wherein each Z is an independently selected oxygen protecting group and wherein LG$^2$ is a leaving group; in a mixture of an ether solvent and a hydrocarbon solvent; to yield the corresponding compound of formula (IX-S);

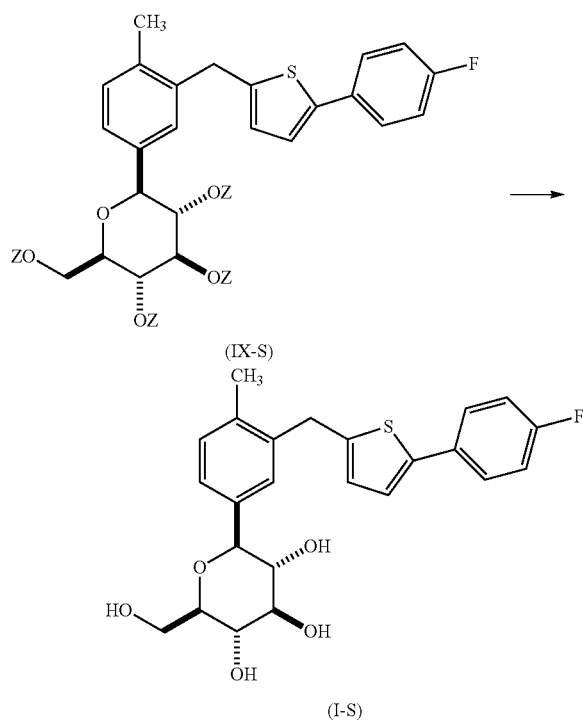

(IX-S)

(I-S)

de-protecting the compound of formula (IX-S); to yield the corresponding compound of formula (I-S).

In another embodiment, the present invention is directed to a process for the preparation of a compound of formula (I-K)

(I-K)

or pharmaceutically acceptable salt or solvate thereof; (also known as 1-(β-D-glucopyranosyl)-4-chloro-3-[5-(4-fluoro-3-pyridyl)-2-thienylmethyl]benzene); comprising

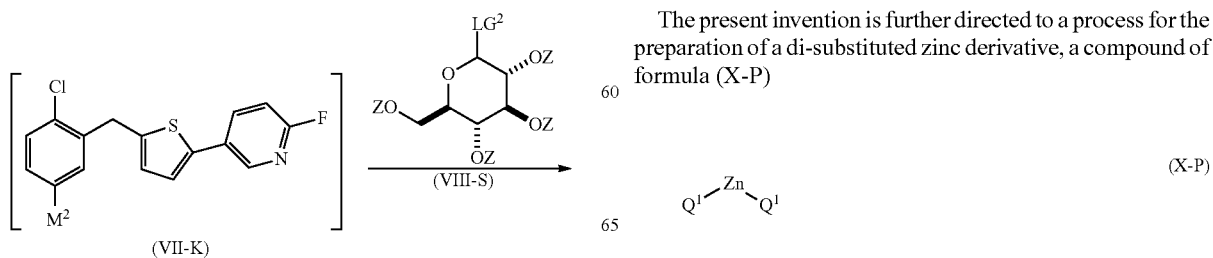

(VII-K)  (VIII-S)

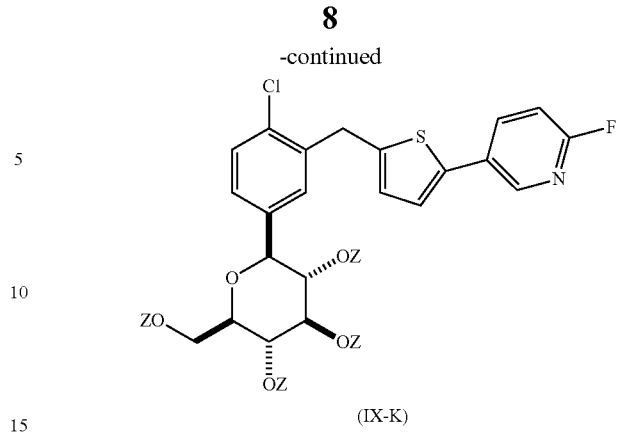

(IX-K)

reacting a compound of formula (VII-K), wherein $M^2$ is a zinc species, with a compound of formula (VIII-S), wherein each Z is an independently selected oxygen protecting group and wherein $LG^2$ is a leaving group; in a mixture of an ether solvent and a hydrocarbon solvent; to yield the corresponding compound of formula (IX-K);

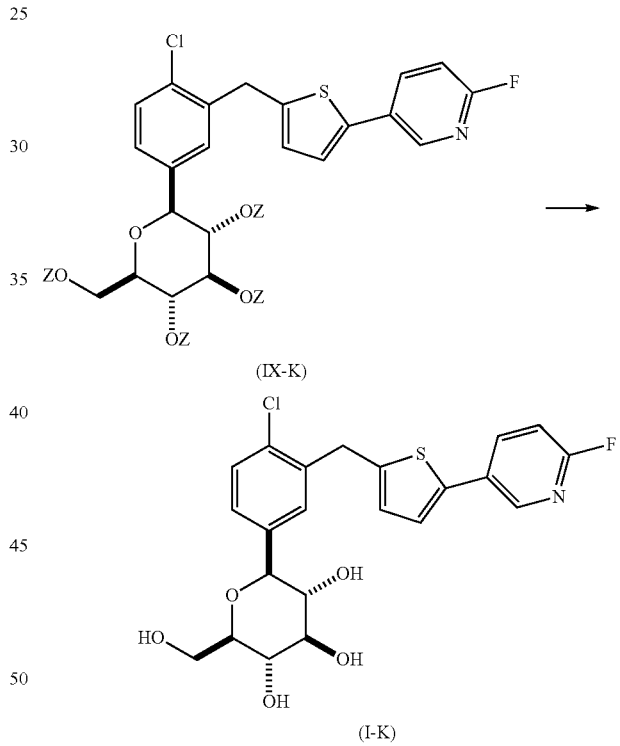

(IX-K)

(I-K)

de-protecting the compound of formula (IX-K); to yield the corresponding compound of formula (I-K).

The present invention is further directed to a process for the preparation of a di-substituted zinc derivative, a compound of formula (X-P)

$$Q^1\text{-Zn-}Q^1$$

(X-P)

wherein both $Q^1$ groups are the same and are

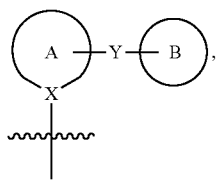

as herein defined; comprising

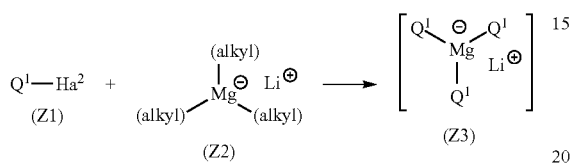

reacting a compound of the formula (Z1), wherein $Ha^2$ is a halogen, with a lithium trialkyl magnesate, a compound of formula (Z2); in a suitably selected anhydrous organic solvent or mixture of anhydrous organic solvents; to yield the corresponding compound of formula (Z3);

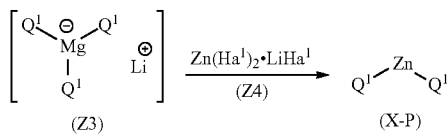

reacting the compound of formula (Z3) with a zinc halide.lithium halide complex, a compound of formula (Z4), wherein $Ha^1$ is a halogen; in a suitably selected anhydrous organic solvent or mixture of anhydrous organic solvents; to yield the corresponding compound of formula (X-P).

The present invention is further directed to a product prepared according to any of the processes described herein.

Illustrative of the invention is a pharmaceutical composition comprising a pharmaceutically acceptable carrier and the product prepared according to any of the processes described herein. An illustration of the invention is a pharmaceutical composition made by mixing the product prepared according to any of the processes described herein and a pharmaceutically acceptable carrier. Illustrating the invention is a process for making a pharmaceutical composition comprising mixing the product prepared according to any of the processes described herein and a pharmaceutically acceptable carrier.

Exemplifying the invention are methods of treating a disorder mediated by SGLT (including treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension,) comprising administering to the subject in need thereof a therapeutically effective amount of any of the compounds or pharmaceutical compositions described above.

Further exemplifying the invention are methods of treating type 1 and type 2 diabetes mellitus, comprising administering to a subject in need of treatment a therapeutically effective amount of a therapeutically effective amount of any of the compounds or pharmaceutical compositions described above, alone or in combination with at least one antidiabetic agent, agent for treating diabetic complications, anti-obesity agent, antihypertensive agent, antiplatelet agent, anti-atherosclerotic agent and/or hypolipidemic agent.

DETAILED DESCRIPTION OF THE INVENTION

The present invention is directed to a process for the preparation of compounds of formula (I)

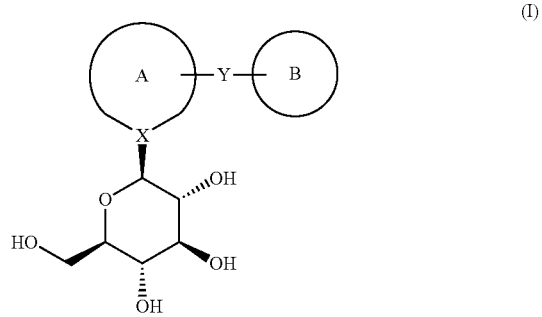

wherein X, Y, Ring A and Ring B are as herein defined; and pharmaceutically acceptable salts and solvates thereof; as described in more detail herein. The compounds of the formula (I) exhibits an inhibitory activity against sodium-dependent glucose transporter being present in the intestine and the kidney of mammalian species, and is useful in the treatment of diabetes mellitus or diabetic complications such as diabetic retinopathy, diabetic neuropathy, diabetic nephropathy, obesity, and delayed wound healing. In an embodiment, the present invention is directed to a process for the preparation of a compound of formula (I-S), as described in more detail herein. In another embodiment, the present invention is directed to a process for the preparation of a compound of formula (I-K), as described in more detail herein.

The term "halogen", shall include chlorine, bromine, fluorine and iodine. When referring to substituents on the compound of formula (I), the term "halogen atom" or "halo" shall mean chlorine, bromine and fluorine, and chlorine and fluorine are preferable.

The term "alkyl group" means a straight or branched saturated monovalent hydrocarbon chain having 1 to 12 carbon atoms. The straight chain or branched chain alkyl group having 1 to 6 carbon atoms is preferable, and the straight chain or branched chain alkyl group having 1 to 4 carbon atoms is more preferable. Examples thereof are methyl group, ethyl group, propyl group, isopropyl group, butyl group, t-butyl group, isobutyl group, pentyl group, hexyl group, isohexyl group, heptyl group, 4,4-dimethylpentyl group, octyl group, 2,2,4-trimethylpentyl group, nonyl group, decyl group, and various branched chain isomers thereof. Further, the alkyl group may optionally and independently be substituted by 1 to 4 substituents as listed below, if necessary.

The term "alkylene group" or "alkylene" means a straight or branched divalent saturated hydrocarbon chain having 1 to 12 carbon atoms. The straight chain or branched chain alkylene group having 1 to 6 carbon atoms is preferable, and the straight chain or branched chain alkylene group having 1 to 4 carbon atoms is more preferable. Examples thereof are methylene group, ethylene group, propylene group, trimethylene group, etc. If necessary, the alkylene group may optionally be substituted in the same manner as the above-mentioned "alkyl group". Where alkylene groups as defined above attach at two different carbon atoms of the benzene ring, they form an annelated five, six or seven membered carbocycle together with the carbon atoms to which they are attached, and may optionally be substituted by one or more substituents defined below.

The term "alkenyl group" means a straight or branched monovalent hydrocarbon chain having 2 to 12 carbon atoms and having at least one double bond. Preferable alkenyl group is a straight chain or branched chain alkenyl group having 2 to 6 carbon atoms, and the straight chain or branched chain alkenyl group having 2 to 4 carbon atoms is more preferable. Examples thereof are vinyl group, 2-propenyl group, 3-butenyl group, 2-butenyl group, 4-pentenyl group, 3-pentenyl group, 2-hexenyl group, 3-hexenyl group, 2-heptenyl group, 3-heptenyl group, 4-heptenyl group, 3-octenyl group, 3-nonenyl group, 4-decenyl group, 3-undecenyl group, 4-dodecenyl group, 4,8,12-tetradecatrienyl group, etc. The alkenyl group may optionally and independently be substituted by 1 to 4 substituents as mentioned below, if necessary.

The term "alkenylene group" means a straight or branched divalent hydrocarbon chain having 2 to 12 carbon atoms and having at least one double bond. The straight chain or branched chain alkenylene group having 2 to 6 carbon atoms is preferable, and the straight chain or branched chain alkenylene group having 2 to 4 carbon atoms is more preferable. Examples thereof are vinylene group, propenylene group, butadienylene group, etc. If necessary, the alkylene group may optionally be substituted by 1 to 4 substituents as mentioned below, if necessary. Where alkenylene groups as defined above attach at two different carbon atoms of the benzene ring, they form an annelated five, six or seven membered carbocycle (e.g., a fused benzene ring) together with the carbon atoms to which they are attached, and may optionally be substituted by one or more substituents defined below.

The term "alkynyl group" means a straight or branched monovalent hydrocarbon chain having at least one triple bond. The preferable alkynyl group is a straight chain or branched chain alkynyl group having 2 to 6 carbon atoms, and the straight chain or branched chain alkynyl group having 2 to 4 carbon atoms is more preferable. Examples thereof are 2-propynyl group, 3-butynyl group, 2-butynyl group, 4-pentynyl group, 3-pentynyl group, 2-hexynyl group, 3-hexynyl group, 2-heptynyl group, 3-heptynyl group, 4-heptynyl group, 3-octynyl group, 3-nonynyl group, 4-decynyl group, 3-undecynyl group, 4-dodecynyl group, etc. The alkynyl group may optionally and independently be substituted by 1 to 4 substituents as mentioned below, if necessary.

The term "cycloalkyl group" means a monocyclic or bicyclic monovalent saturated hydrocarbon ring having 3 to 12 carbon atoms, and the monocyclic saturated hydrocarbon group having 3 to 7 carbon atoms is more preferable. Examples thereof are a monocyclic alkyl group and a bicyclic alkyl group such as cyclopropyl group, cyclobutyl group, cyclopentyl group, cyclohexyl group, cycloheptyl group, cyclooctyl group, cyclodecyl group, etc. These groups may optionally and independently be substituted by 1 to 4 substituents as mentioned below, if necessary. The cycloalkyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the condensed unsaturated hydrocarbon ring may be optionally and independently be substituted by 1 to 4 substituents as mentioned below.

The term "cycloalkylidene group" means a monocyclic or bicyclic divalent saturated hydrocarbon ring having 3 to 12 carbon atoms, and the monocyclic saturated hydrocarbon group having 3 to 6 carbon atoms is preferable. Examples thereof are a monocyclic alkylidene group and a bicyclic alkylidene group such as cyclopropylidene group, cyclobutylidene group, cyclopentylidine group, cyclohexylidene group, etc. These groups may optionally and independently be substituted by 1 to 4 substituents as mentioned below, if necessary. Besides, the cycloalkylidene group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkenyl group" means a monocyclic or bicyclic monovalent unsaturated hydrocarbon ring having 4 to 12 carbon atoms and having at least one double bond. The preferable cycloalkenyl group is a monocyclic unsaturated hydrocarbon group having 4 to 7 carbon atoms. Examples thereof are monocyclic alkenyl groups such as cyclopentenyl group, cyclopentadienyl group, cyclohexenyl group, etc. These groups may optionally and independently be substituted by 1 to 4 substituents as mentioned below, if necessary. Besides, the cycloalkenyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkynyl group" means a monocyclic or bicyclic unsaturated hydrocarbon ring having 6 to 12 carbon atoms, and having at least one triple bond. The preferable cycloalkynyl group is a monocyclic unsaturated hydrocarbon group having 6 to 8 carbon atoms. Examples thereof are monocyclic alkynyl groups such as cyclooctynyl group, cyclodecynyl group. These groups may optionally be substituted by 1 to 4 substituents as mentioned below, if necessary. Besides, the cycloalkynyl group may optionally and independently be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "aryl group" means a monocyclic or bicyclic monovalent aromatic hydrocarbon group having 6 to 10 carbon atoms. Examples thereof are phenyl group, naphthyl group (including 1-naphthyl group and 2-naphthyl group). These groups may optionally and independently be substituted by 1 to 4 substituents as mentioned below, if necessary. Besides, the aryl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "unsaturated monocyclic heterocyclic ring" means an unsaturated hydrocarbon ring containing 1-4 heteroatoms independently selected from a nitrogen atom, an oxygen atom and a sulfur atom, and the preferable one is a 4- to 7-membered saturated or unsaturated hydrocarbon ring containing 1-4 heteroatoms independently selected from a nitrogen atom, an oxygen atom and a sulfur atom. Examples thereof are pyridine, pyrimidine, pyrazine, furan, thiophene, pyrrole, imidazole, pyrazole, oxazole, isoxazole, 4,5-dihydrooxazole, thiazole, isothiazole, thiadiazole, triazole, tetrazole, etc. Among them, pyridine, pyrimidine, pyrazine, furan, thiophene, pyrrole, imidazole, oxazole, and thiazole can be preferably used. The "unsaturated monocyclic heterocyclic ring" may optionally and independently be substituted by 1-4 substituents as mentioned below, if necessary.

The term "unsaturated fused heterobicyclic ring" means hydrocarbon ring comprised of a saturated or a unsaturated hydrocarbon ring condensed with the above mentioned unsaturated monocyclic heterocyclic ring where said saturated hydrocarbon ring and said unsaturated hydrocarbon ring may optionally contain an oxygen atom, a nitrogen atom, a sulfur atom, SO, or $SO_2$ within the ring, if necessary. The "unsaturated fused heterobicyclic ring" includes, for example, benzothiophene, indole, tetrahydrobenzothiophene, benzofuran, isoquinoline, thienothiophene, thienopyridine, quinoline, indoline, isoindoline, benzothiazole, benzoxazole, indazole, dihydroisoquinoline, etc. Further, the "heterocyclic ring" also includes possible N- or S-oxides thereof.

The term "heterocyclyl" means a monovalent group of the above-mentioned unsaturated monocyclic heterocyclic ring or unsaturated fused heterobicyclic ring and a monovalent group of the saturated version of the above-mentioned unsaturated monocyclic heterocyclic or unsaturated fused heterobicyclic ring. If necessary, the heterocyclyl may optionally and independently be substituted by 1 to 4 substituents as mentioned below.

The term "alkanoyl group" means a formyl group and ones formed by binding an "alkyl group" to a carbonyl group.

The term "alkoxy group" means ones formed by binding an "alkyl group" to an oxygen atom.

The substituent for the above each group includes, for example, a halogen atom (fluorine, chlorine, bromine), a nitro group, a cyano group, an oxo group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a hetero-cyclylcarbonyl group, an alkoxy-carbonyl group, an alkenyloxy-carbonyl group, an alkynyloxy-carbonyl group, a cycloalkyloxy-carbonyl group, a cycloalkenyloxy-carbonyl group, a cyclo-alkynyl-oxycarbonyl group, an aryloxycarbonyl group, a hetero-cyclyloxycarbonyl group, an alkanoyloxy group, an alkenyl-carbonyloxy group, an alkynyl-carbonyloxy group, a cycloalkyl-carbonyloxy group, a cycloalkenyl-carbonyloxy group, a cycloalkynyl-carbonyloxy group, an arylcarbonyloxy group, a hetero-cyclylcarbonyloxy group, an alkylthio group, an alkenyl-thio group, an alkynylthio group, a cycloalkylthio group, a cycloalkenyl-thio group, a cycloalkynylthio group, an arylthio group, a heterocyclylthio group, an amino group, a mono- or di-alkyl-amino group, a mono- or di-alkanoylamino group, a mono- or di-alkoxy-carbonyl-amino group, a mono- or di-arylcarbonyl-amino group, an alkylsulfinylamino group, an alkyl-sulfonyl-amino group, an arylsulfinylamino group, an arylsulfonylamino group, a carbamoyl group, a mono- or di-alkyl-carbamoyl group, a mono- or di-arylcarbamoyl group, an alkylsulfinyl group, an alkenyl-sulfinyl group, an alkynyl-sulfinyl group, a cycloalkyl-sulfinyl group, a cycloalkenyl-sulfinyl group, a cycloalkynyl-sulfinyl group, an arylsulfinyl group, a heterocyclyl-sulfinyl group, an alkyl-sulfonyl group, an alkenylsulfonyl group, an alkynylsulfonyl group, a cycloalkylsulfonyl group, a cycloalkenyl-sulfonyl group, a cycloalkynylsulfonyl group, an aryl-sulfonyl group, and a heterocyclylsulfonyl group. Each group as mentioned above may optionally be substituted by these substituents.

Further, the terms such as a haloalkyl group, a halo-lower alkyl group, a haloalkoxy group, a halo-lower alkoxy group, a halophenyl group, or a haloheterocyclyl group mean an alkyl group, a lower alkyl group, an alkoxy group, a lower alkoxy group, a phenyl group or a heterocyclyl group (hereinafter, referred to as an alkyl group, etc.) being substituted by one or more halogen atoms, respectively. Preferable ones are an alkyl group, etc. being substituted by 1 to 7 halogen atoms, and more preferable ones are an alkyl group, etc. being substituted by 1 to 5 halogen atoms. Similarly, the terms such as a hydroxyalkyl group, a hydroxy-lower alkyl group, a hydroxyalkoxy group, a hydroxy-lower alkoxy group and a hydroxyphenyl group mean an alkyl group, etc., being substituted by one or more hydroxy groups. Preferable ones are an alkyl group, etc., being substituted by 1 to 4 hydroxy groups, and more preferable ones are an alkyl group, etc., being substituted by 1 to 2 hydroxy groups. Further, the terms such as an alkoxyalkyl group, a lower alkoxyalkyl group, an alkoxy-lower alkyl group, a lower alkoxy-lower alkyl group, an alkoxyalkoxy group, a lower alkoxyalkoxy group, an alkoxy-lower alkoxy group, a lower alkoxy-lower alkoxy group, an alkoxyphenyl group, and a lower alkoxyphenyl group means an alkyl group, etc., being substituted by one or more alkoxy groups. Preferable ones are an alkyl group, etc., being substituted by 1 to 4 alkoxy groups, and more preferable ones are an alkyl group, etc., being substituted by 1 to 2 alkoxy groups.

The terms "arylalkyl" and "arylalkoxy" as used alone or as part of another group refer to alkyl and alkoxy groups as described above having an aryl substituent.

The term "lower" used in the definitions for the formulae in the present specification means a straight or branched carbon chain having 1 to 6 carbon atoms, unless defined otherwise. More preferably, it means a straight or branched carbon chain having 1 to 4 carbon atoms.

The term "prodrug" means an ester or carbonate, which is formed by reacting one or more hydroxy groups of the compound of the formula I with an acylating agent substituted by an alkyl, an alkoxy or an aryl by a conventional method to produce acetate, pivalate, methylcarbonate, benzoate, etc. Further, the prodrug includes also an ester or amide, which is similarly formed by reacting one or more hydroxy groups of the compound of the formula I with an α-amino acid or a β-amino acid, etc. using a condensing agent by a conventional method.

The pharmaceutically acceptable salt of the compound of the formula I includes, for example, a salt with an alkali metal such as lithium, sodium, potassium, etc.; a salt with an alkaline earth metal such as calcium, magnesium, etc.; a salt with zinc or aluminum; a salt with an organic base such as ammonium, choline, diethanolamine, lysine, ethylenediamine, t-butylamine, t-octylamine, tris(hydroxymethyl)aminomethane, N-methyl glucosamine, triethanolamine and dehydroabietylamine; a salt with an inorganic acid such as hydrochloric acid, hydrobromic acid, hydroiodic acid, sulfuric acid, nitric acid, phosphoric acid, etc.; or a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, etc.; or a salt with an acidic amino acid such as aspartic acid, glutamic acid, etc.

The compound of the present invention also includes a mixture of stereoisomers, or each pure or substantially pure isomer. For example, the present compound may optionally have one or more asymmetric centers at a carbon atom containing any one of substituents. Therefore, the compound of the formula I may exist in the form of enantiomer or diastereomer, or a mixture thereof. When the present compound (I) contains a double bond, the present compound may exist in the form of geometric isomerism (cis-compound, trans-compound), and when the present compound (I) contains an unsaturated bond such as carbonyl, then the present compound may exist in the form of a tautomer, and the present compound also includes these isomers or a mixture thereof. The starting compound in the form of a racemic mixture, enantiomer or diastereomer may be used in the processes for preparing the present compound. When the present compound is obtained in the form of a diastereomer or enantiomer, they can be separated by a conventional method such as chromatography or fractional crystallization.

In addition, the present compound (I) includes an intramolecular salt, hydrate, solvate or polymorph thereof.

Examples of the optionally substituted unsaturated monocyclic heterocyclic ring of the present invention include an unsaturated monocyclic heterocyclic ring which may optionally be substituted by 1-5 substituents selected from the group consisting of a halogen atom, a nitro group, a cyano group, an oxo group, a hydroxyl group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, and a heterocyclylsulfonyl group wherein each substituent may optionally be further substituted by these substituents.

Examples of the optionally substituted unsaturated fused heterobicyclic ring of the present invention include an unsaturated fused heterobicyclic ring which may optionally be substituted by 1-5 substituents selected from the group consisting of a halogen atom, a nitro group, a cyano group, an oxo group, a hydroxy group, a mercapto group, a carboxyl group, a sulfo group, an alkyl group, an alkenyl group, an alkynyl group, a cycloalkyl group, a cycloalkylidene-methyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenyl-carbonyl group, a cycloalkynyl-carbonyl group, an arylcarbonyl group, a heterocyclylcarbonyl group, an alkoxycarbonyl group, an alkenyloxycarbonyl group, an alkynyloxy-carbonyl group, a cycloalkyloxycarbonyl group, a cycloalkenyloxy-carbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cyclo-alkylcarbonyloxy group, a cycloalkenylcarbonyloxy group, a cyclo-alkynylcarbonyloxy group, an arylcarbonyloxy group, a heterocyclyl-carbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoyl-amino group, a mono- or di-alkoxycarbonylamino group, a mono- or di-arylcarbonylamino group, an alkylsulfinylamino group, an alkyl-sulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cyclo-alkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, and a heterocyclylsulfonyl group, wherein each substituent may optionally be further substituted by these substituents.

Examples of the optionally substituted benzene ring of the present invention include a benzene ring which may optionally be substituted by 1-5 substituents selected from the group consisting of a halogen atom, a nitro group, a cyano group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyl-oxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, a heterocyclylsulfonyl group, an alkylene group, an alkyleneoxy group, an alkylenedioxy group, and an alkenylene group wherein each substituent may optionally be further substituted by these substituents.

Moreover, examples of the optionally substituted benzene ring include a benzene ring substituted with an alkylene group to form an annelated carbocycle together with the carbon atoms to which they are attached, and also includes a benzene ring substituted with an alkenylene group to form an annelated carbocycle such as a fused benzene ring together with the carbon atoms to which they are attached.

Preferable examples of the optionally substituted unsaturated monocyclic heterocyclic ring include an unsaturated monocyclic heterocyclic ring which may optionally be substituted by 1-3 substituents selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, and an oxo group.

Preferable examples of the optionally substituted unsaturated fused heterobicyclic ring include an unsaturated fused heterobicyclic ring which may optionally be substituted by 1-3 substituents independently selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, and an oxo group.

Preferable examples of the optionally substituted benzene ring include a benzene ring which may optionally be substituted by 1-3 substituents selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, an alkylene group, an alkyleneoxy group, an alkylenedioxy group, and an alkenylene group.

In another preferable embodiment of the present invention, the optionally substituted unsaturated monocyclic heterocyclic ring is an unsaturated monocyclic heterocyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group; the optionally substituted unsaturated fused heterobicyclic ring is an unsaturated fused heterobicyclic ring which may optionally be substituted by 1-3 substituents selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkylthio group, an alkylsulfonyl group, an alkylsulfinyl group, an amino group, a mono- or di-alkylamino group, an alkanoylamino group, an alkoxycarbonylamino group, a sulfamoyl group, a mono- or di-alkyl-sulfamoyl group, a carboxyl group, an alkoxycarbonyl group, a carbamoyl group, a mono- or di-alkylcarbamoyl group, an alkanoyl group, an alkylsulfonylamino group, a phenyl group, a phenoxy group, a phenylsulfonylamino group, phenylsulfonyl group, a heterocyclyl group, and an oxo group; and the optionally substituted benzene ring is a benzene ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group;

wherein each of the above-mentioned substituents on the unsaturated monocyclic heterocyclic ring, the unsaturated fused heterobicyclic ring and the benzene ring may further be substituted by 1-3 substituents, independently selected from the group consisting of a halogen atom, a hydroxy group, a cyano group, an alkyl group, a haloalkyl group, an alkoxy group, a haloalkoxy group, an alkanoyl group, an alkylthio group, an alkylsulfonyl group, a mono- or di-alkylamino group, a carboxyl group, an alkoxycarbonyl group, a phenyl group, an alkyleneoxy group, an alkylenedioxy group, an oxo group, a carbamoyl group, and a mono- or di-alkylcarbamoyl group.

In a preferable embodiment, the optionally substituted unsaturated monocyclic heterocyclic ring is an unsaturated monocyclic heterocyclic ring which may optionally be substituted by 1-3 substituents, independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, and an oxo group;

the optionally substituted unsaturated fused heterobicyclic ring is an unsaturated fused heterobicyclic ring which may optionally be substituted by 1-3 substituents independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxy group, an alkoxycarbonyl group, a carbamoyl group, a mono- or di-alkylcarbamoyl group, a phenyl group, a heterocyclyl group, and an oxo group; and the optionally substituted benzene ring is a benzene ring which may optionally be substituted by 1-3 substituents, independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, an alkylene group, and an alkenylene group;

wherein each of the above-mentioned substituents on the unsaturated monocyclic heterocyclic ring, the unsaturated fused heterobicyclic ring and the benzene ring may further be substituted by 1-3 substituents, independently selected from the group consisting of a halogen atom, a cyano group, an alkyl group, a haloalkyl group, an alkoxy group, a haloalkoxy group, an alkanoyl group, a mono- or di-alkylamino group, a carboxyl group, a hydroxy group, a phenyl group, an alkylenedioxy group, an alkyleneoxy group, an alkoxycarbonyl group, a carbamoyl group and a mono- or di-alkylcarbamoyl group.

In another preferable embodiment, (1) Ring A is an unsaturated monocyclic heterocyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group, and Ring B is an unsaturated monocyclic heterocyclic ring, an unsaturated fused heterobicyclic ring, or a benzene ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group;

(2) Ring A is a benzene ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, an alkanoylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group, and Ring B is an unsaturated monocyclic heterocyclic ring or an unsaturated fused heterobicyclic ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group and an oxo group; or (3) Ring A is an unsaturated fused heterobicyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group, and Ring B is an unsaturated monocyclic heterocyclic ring, an unsaturated fused heterobicyclic ring, or a benzene ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group and an oxo group;

wherein each of the above-mentioned substituents on Ring A and Ring B may optionally be substituted by 1-3 substituents, independently selected from the group consisting of a halogen atom, a cyano group, an alkyl group, a haloalkyl group, an alkoxy group, a haloalkoxy group, an alkanoyl group, a mono- or di-alkylamino group, a carboxyl group, a hydroxy group, a phenyl group, an alkylenedioxy group, an alkyleneoxy group, an alkoxycarbonyl group, a carbamoyl group and a mono- or di-alkylcarbamoyl group.

In a more preferable embodiment of the present invention, Ring A and Ring B are (1) Ring A is an unsaturated monocyclic heterocyclic ring which may optionally be substituted by a halogen atom, a lower alkyl group, a halo-lower alkyl group, a lower alkoxy group, or an oxo group, and Ring B is (a) a benzene ring which may optionally be substituted by a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halolower alkyl group, a lower alkoxy group, or a mono- or di-lower alkylamino group; or a heterocyclyl group optionally substituted by a halogen atom, a cyano group, a lower alkyl group, a halo-lower alkyl group, a lower alkoxy group, or a mono- or di-lower alkylamino group; (b) an unsaturated monocyclic heterocyclic ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; or (c) an unsaturated fused heterobicyclic ring which may optionally be substituted by a group selected from a halogen atom, cyano group, a lower alkyl group, a halo-lower alkyl group, a lower alkoxy group, a halo-lower alkoxy group, a mono- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group;

(2) Ring A is a benzene ring which may optionally be substituted by a halogen atom, a lower alkyl group, a halolower alkyl group, a lower alkoxy group, a phenyl group, or a lower alkenylene group, and Ring B is (a) an unsaturated monocyclic heterocyclic ring which may optionally be substituted by a halogen atom; a cyano group; a lower alkyl group; a halo-lower alkyl group; a phenyl-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, a mono- or di-lower alkylamino group, or a carbamoyl group; or a heterocyclyl group optionally substituted by a halogen atom, a cyano group, a lower alkyl group, a halo-lower alkyl group, a lower alkoxy group, a mono- or di-lower alkylamino group or a carbamoyl group; (b) an unsaturated fused heterobicyclic ring which may optionally be substituted by a group selected from a halogen atom, cyano group, a lower alkyl group, a halo-lower alkyl group, a phenyl-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; or (3) Ring A is an unsaturated fused heterobicyclic ring which may optionally be substituted by a halogen atom, a lower alkyl group, a halo-lower alkyl group, a lower alkoxy group, or an oxo group, and Ring B is (a) a benzene ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; (b) an unsaturated monocyclic heterocyclic ring which may optionally be substituted by a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group; or a heterocyclyl group optionally substituted by a halogen atom, a cyano group, a lower alkyl group, a halo-lower alkyl group, a lower alkoxy group, or a mono- or di-lower alkylamino group; or (c) an unsaturated fused heterobicyclic ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group.

In another more preferable embodiment, Y is —$CH_2$— and is linked at the 3-position of Ring A, with respect to X being the 1-position, Ring A is a benzene ring which is substituted by 1-3 substituents selected from the group consisting of a lower alkyl group, a halo-lower alkyl group, a halogen atom, a lower alkoxy group, a phenyl group, and a lower alkenylene group, and Ring B is an unsaturated monocyclic heterocyclic ring or an unsaturated fused heterobicyclic ring, each of which may be substituted by 1-3 substituents selected from the group consisting of a lower alkyl group, a halo-lower alkyl group, a phenyl-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a halo-lower alkoxy phenyl group, a lower alkylenedioxyphenyl group, a lower alkyleneoxy phenyl group, a mono- or di-lower alkylaminophenyl group, a carbamoyl phenyl group, a mono- or di-lower alkylcarbamoylphenyl group, a heterocyclyl group, a haloheterocyclyl group, a cyanoheterocyclyl group, a lower alkylheterocyclyl group, a lower alkoxyheterocyclyl group, a mono- or di-lower alkylaminoheterocycyclyl group, a carbamoylheterocyclyl group, and a mono- or di-lower alkylcarbamoyl group.

In another more preferable embodiment, Y is —$CH_2$— and is linked at the 3-position of Ring A, with respect to X being the 1-position, Ring A is an unsaturated monocyclic heterocyclic ring which may be substituted by 1-3 substituents selected from the group consisting of a lower alkyl group, a halogen atom, a lower alkoxy group, and an oxo group, and Ring B is a benzene ring which may be substituted by 1-3 substituents selected from the group consisting of a lower alkyl group, a halo-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a heterocyclyl group, a haloheterocyclyl group, a cyanoheterocyclyl group, a lower alkylheterocyclyl group, and a lower alkoxyheterocyclyl group.

Further, in another preferable embodiment, Y is —$CH_2$— and is linked at the 3-position of Ring A, with respect to X being the 1-position, Ring A is an unsaturated monocyclic heterocyclic ring which may be substituted by 1-3 substituents selected from the group consisting of a lower alkyl group, a halogen atom, a lower alkoxy group, and an oxo group, and Ring B is an unsaturated monocyclic heterocyclic ring or an unsaturated fused heterobicyclic ring, each of which may be substituted by 1-3 substituents selected from the group consisting of a lower alkyl group, a halo-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a halo-lower alkoxyphenyl group, a heterocyclyl group, a haloheterocyclyl group, a cyanoheterocyclyl group, a lower alkylheterocyclyl group, and a lower alkoxyheterocyclyl group.

In a more preferable embodiment of the present invention, X is a carbon atom and Y is —$CH_2$—.

Further, in another preferable embodiment, Ring A and Ring B are:

(1) Ring A is a benzene ring which may optionally be substituted by 1-3 substituents, independently selected from the group consisting of a halogen atom, a lower alkyl group optionally substituted by a halogen atom or a lower alkoxy group, a lower alkoxy group optionally substituted by a halogen atom or a lower alkoxy group, a cycloalkyl group, a cycloalkoxy group, a phenyl group, and a lower alkenylene group, and Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group, a halo-lower alkoxy group, or a carbamoyl group; a heterocyclyl group optionally substituted by a halogen atom, a cyano group, a lower alkyl group, a halo-lower alkyl group, a lower alkoxy group, a halo-lower alkoxy group or a carbamoyl group; and an oxo group, (2) Ring A is an unsaturated monocyclic heterocyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, and Ring B is a benzene ring which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; a lower alkylene group, (3) Ring A is an unsaturated monocyclic heterocyclic ring which may optionally be substituted by 1-3 substituents, independently selected from the group consisting of a halogen atom, a lower alkyl group optionally substituted by a halogen atom or a lower alkoxy group, a lower alkoxy group optionally substituted by a halogen atom or a lower alkoxy group, a cycloalkyl group, a cycloalkoxy group, and an oxo group, Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and an oxo group;

(4) Ring A is an unsaturated fused heterobicyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, Ring B is a benzene ring which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and a lower alkylene group, or (5) Ring A is an unsaturated monocyclic heterocyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and an oxo group.

In another preferable embodiment of the present invention, Y is linked at the 3-position of Ring A, with respect to X being the 1-position, Ring A is a benzene ring which may optionally be substituted by a halogen atom, a lower alkyl group optionally substituted by a halogen atom, a lower alkoxy group, or a phenyl group, and Ring B is an unsaturated monocyclic heterocyclic ring or an unsaturated fused heterobicyclic ring which may optionally be substituted by 1-3 substituents, independently selected from the group consisting of a halogen atom; a lower alkyl group optionally substituted by a halogen atom or a phenyl group; a lower alkoxy group; a phenyl group optionally substituted by a halogen atom, a cyano group, a lower alkyl group, a halo-lower alkyl group, or a lower alkoxy group; a heterocyclyl group optionally substituted by a halogen atom, a cyano group, a lower alkyl group, a halo-lower alkyl group, or a lower alkoxy group; and an oxo group.

In another more preferable embodiment of the present invention, Y is linked at the 3-position of Ring A, with respect to X being the 1-position, Ring A is an unsaturated monocyclic heterocyclic ring which may optionally be substituted by a substituent selected from a halogen atom, a lower alkyl group, and an oxo group, and Ring B is a benzene ring which may optionally be substituted by a substituent selected from the group consisting of a halogen atom; a lower alkyl group optionally substituted by a halogen atom or a phenyl group; a lower alkoxy group; a phenyl group optionally substituted by a halogen atom, a cyano group, a lower alkyl group, a halo-lower alkyl group, or a lower alkoxy group; a heterocyclyl group optionally substituted by a halogen atom, a cyano group, a lower alkyl group, a halo-lower alkyl group, or a lower alkoxy group; and a lower alkylene group.

Preferable examples of unsaturated monocyclic heterocyclic ring include a 5- or 6-membered unsaturated heterocyclic ring containing 1 or 2 hetero atoms independently selected from a nitrogen atom, an oxygen atom, and a sulfur atom. More specifically, preferred are furan, thiophene, oxazole, isoxazole, triazole, tetrazole, pyrazole, pyridine, pyrimidine, pyrazine, dihydroisoxazole, dihydropyridine, and thiazole. Preferable unsaturated fused heterobicyclic ring includes a 9- or 10-membered unsaturated fused heterocyclic ring containing 1 to 4 hetero atoms independently selected from a nitrogen atom, an oxygen atom, and a sulfur atom. More specifically, preferred are indoline, isoindoline, benzothiazole, benzoxazole, indole, indazole, quinoline, isoquinoline, benzothiophene, benzofuran, thienothiophene, and dihydroisoquinoline.

In a more preferred embodiment of the present invention, Ring A is a benzene ring which may optionally be substituted by a substituent selected from the group consisting of a halogen atom, a lower alkyl group, a halo-lower alkyl group, a lower alkoxy group, and a phenyl group, and Ring B is a heterocyclic ring selected from the group consisting of thiophene, furan, benzofuran, benzothiophene, and benzothiazole, wherein the heterocyclic ring may optionally be substituted by a substituent selected from the following group: a halogen atom, a cyano group, a lower alkyl group, a halo-lower alkyl group, a phenyl-lower alkyl group, a lower alkoxy group, a halo-lower alkoxy group, a phenyl group, a halophenyl group, a lower alkylphenyl group, a lower alkoxyphenyl group, a thienyl group, a halothienyl group, a pyridyl group, a halopyridyl group, and a thiazolyl group.

In yet another preferred embodiment, Y is —CH$_2$—, Ring A is an unsaturated monocyclic heterocyclic ring or an unsaturated fused heterobicyclic ring selected from the group consisting of thiophene, dihydroisoquinoline, dihydroisoxazole, triazole, pyrazole, dihydropyridine, dihydroindole, indole, indazole, pyridine, pyrimidine, pyrazine, quinoline, and a isoindoline, wherein the heterocyclic ring may optionally substituted by a substituent selected from the following group: a halogen atom, a lower alkyl group, and an oxo group, and Ring B is a benzene ring which may optionally be substituted by a substituent selected from the following group: a halogen atom, a lower alkyl group, a halo-lower alkyl group, a lower alkoxy group, and a halo-lower alkoxy group.

In a further preferred embodiment of the present invention, Ring A is a benzene ring which is substituted by a halogen atom or a lower alkyl group, and Ring B is thienyl group which is substituted by phenyl group or a heterocyclyl group in which said phenyl group and heterocyclyl group is substituted by 1-3 substituents selected from a halogen atom, a cyano group, a lower alkyl group, a halo-lower alkyl group, a lower alkoxy group, and a halo-lower alkoxy group.

Further, in another aspect of the present invention, preferable examples of the compound of the formula I include a compound wherein Ring A is

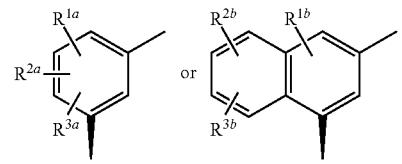

wherein $R^{1a}$, $R^{2a}$, $R^{3a}$, $R^{1b}$, $R^{2b}$, and $R^{3b}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, a phenyl group, a phenylalkoxy group, a cyano group, a nitro group, an amino group, a mono- or di-alkylamino group, an alkanoylamino group, a carboxyl group, an alkoxycarbonyl group, a carbamoyl group, a mono- or di-alkylcarbamoyl group, an alkanoyl group, an alkylsulfonylamino group, a phenylsulfonylamino group, an alkylsulfinyl group, an alkylsulfonyl group, or a phenylsulfonyl group, and Ring B is

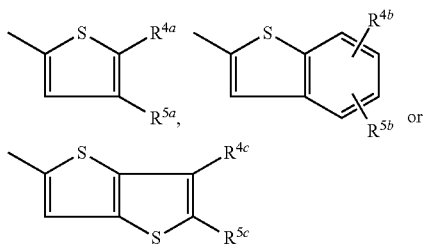

wherein $R^{4a}$ and $R^{5a}$ are each independently a hydrogen atom; a halogen atom; a hydroxy group; an alkoxy group; an alkyl group; a haloalkyl group; a haloalkoxy group; a hydroxyalkyl group; an alkoxyalkyl group; a phenylalkyl group; an alkoxyalkoxy group; a hydroxyalkoxy group; an alkenyl group; an alkynyl group; a cycloalkyl group; a cycloalkylidenemethyl group; a cycloalkenyl group; a cycloalkyloxy group; a phenyloxy group; a phenylalkoxy group; a cyano group; a nitro group; an amino group; a mono- or di-alkylamino group; an alkanoylamino group; a carboxyl group; an alkoxycarbonyl group; a carbamoyl group; a mono- or di-alkylcarbamoyl group; an alkanoyl group; an alkylsulfonylamino group; a phenylsulfonylamino group; an alkylsulfinyl group; an alkylsulfonyl group; a phenylsulfonyl group; a phenyl group optionally substituted by a halogen atom, a cyano group, an alkyl group, a haloalkyl group, an alkoxy group, a haloalkoxy group, an alkylenedioxy group, an alkyleneoxy group, a mono- or di-alkylamino group, a carbamoyl group, or a mono- or di-alkylcarbamoyl group; or a heterocyclyl group optionally substituted by a halogen atom, a cyano group, an alkyl group, a haloalkyl group, an alkoxy group, a haloalkoxy group, a carbamoyl group, or a mono- or di-alkylcarbamoyl group, or $R^{4a}$ and $R^{5a}$ are bonded to each other at the terminals thereof to form an alkylene group; and $R^{4b}$, $R^{5b}$, $R^{4c}$ and $R^{5c}$ are each independently a hydrogen atom; a halogen atom; a hydroxy group; an alkoxy group; an alkyl group; a haloalkyl group; a haloalkoxy group; a hydroxyalkyl group; an alkoxyalkyl group; a phenylalkyl group; an alkoxyalkoxy group; a hydroxyalkoxy group; an alkenyl group; an alkynyl group; a cycloalkyl group; a cycloalkylidenemethyl group; a cycloalkenyl group; a cycloalkyloxy group; a phenyloxy group; a phenylalkoxy group; a cyano group; a nitro group; an amino group; a mono- or di-alkylamino group; an alkanoylamino group; a carboxyl group; an alkoxycarbonyl group; a carbamoyl group; a mono- or di-alkylcarbamoyl group; an alkanoyl group; an alkylsulfonylamino group; a phenylsulfonylamino group; an alkylsulfinyl group; an alkylsulfonyl group; a phenylsulfonyl group; a phenyl group optionally substituted by a halogen atom, a cyano group, an alkyl group, a haloalkyl group, an alkoxy group, a haloalkoxy group, a methylenedioxy group, an ethyleneoxy group, or a mono- or di-alkylamino group; or a heterocyclyl group optionally substituted by a halogen atom, a cyano group, an alkyl group, a haloalkyl group, an alkoxy group or a haloalkoxy group.

More preferred is a compound wherein $R^{1a}$, $R^{2a}$, $R^{3a}$, $R^{1b}$, $R^{2b}$, and $R^{3b}$ are each independently a hydrogen atom, a halogen atom, a lower alkyl group, a halo-lower alkyl group, a lower alkoxy group, or a phenyl group;

$R^{4a}$ and $R^{5a}$ are each independently a hydrogen atom; a halogen atom; a lower alkyl group; a halo-lower alkyl group; a phenyl-lower alkyl group; a phenyl group optionally substituted by a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, or a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, or $R^{4a}$ and $R^{5a}$ are bonded to each other at the terminals thereof to form a lower alkylene group; and $R^{4a}$, $R^{5a}$, $R^{4c}$ and $R^{5c}$ are each independently a hydrogen atom, a halogen atom, a lower alkyl group, a halo-lower alkyl group, a lower alkoxy group, or a halo-lower alkoxy group.

Further preferred is a compound in which Ring B is

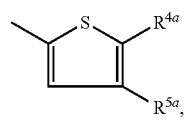

wherein $R^{4a}$ is a phenyl group optionally substituted by a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, or a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, and $R^{5a}$ is a hydrogen atom, or $R^{4a}$ and $R^{5a}$ are bonded to each other at the terminals thereof to form a lower alkylene group.

Further more preferred is a compound in which Ring A is

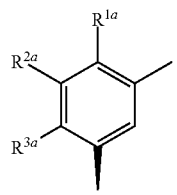

wherein $R^{1a}$ is a halogen atom, a lower alkyl group, or a lower alkoxy group, and $R^{2a}$ and $R^{3a}$ are hydrogen atoms; and Ring B is

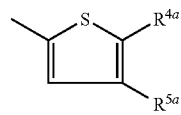

wherein $R^{4a}$ is a phenyl group optionally substituted by a substituent selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, and $R^{5a}$ is a hydrogen atom, and Y is —$CH_2$—.

In more preferable embodiment, $R^{4a}$ is a phenyl group optionally substituted by a halogen atom, a cyano group, a lower alkyl group, a halo-lower alkyl group, a lower alkoxy group, or a halo-lower alkoxy group; or a heterocyclyl group optionally substituted by a halogen atom, a cyano group, a lower alkyl group, or a lower alkoxy group.

In another preferable embodiment of the present invention, a preferable compound can be represented by the following formula IA:

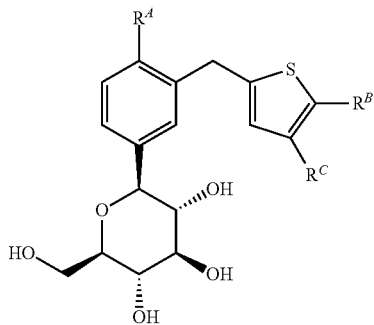

(IA)

wherein $R^A$ is a halogen atom, a lower alkyl group or a lower alkoxy group; $R^B$ is a phenyl group optionally substituted by 1-3 substituents selected from a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group optionally substituted by 1-3 substituents selected from a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group; and $R^C$ is hydrogen atom; or $R^B$ and $R^C$ taken together are a fused benzene ring which may be substituted by a halogen atom, a lower alkyl group, a halo-lower alkyl group, a lower alkoxy group or a halo-lower alkoxy group.

In a preferable embodiment, $R^A$ is a halogen atom or a lower alkyl group, $R^C$ is hydrogen atom, and $R^B$ is phenyl group substituted by 1-3 substituents selected from a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group. The chemical structure of such compounds are represented by the following formula (IA'):

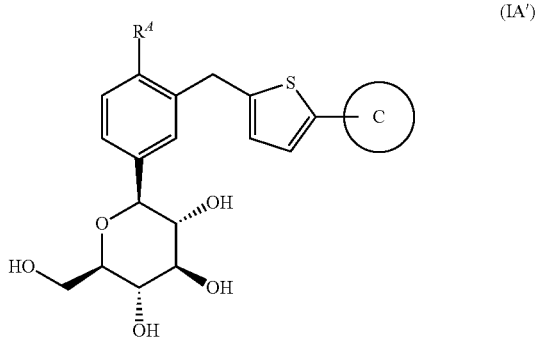

(IA')

wherein $R^A$ is a halogen atom, or a lower alkyl group, Ring C is a phenyl group substituted by 1-3 substituents selected from the group consisting of a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group.

In a more preferable embodiment, Ring C is a phenyl group substituted by 1-3 substituents selected from the group consisting of a halogen atom, a cyano group, a lower alkyl group, a halo-lower alkyl group, a lower alkoxy group, a halo-lower alkoxy group, and a mono- or di-lower alkylamino group; or a heterocyclyl group substituted by a substituent selected from the group consisting of a halogen atom, a cyano group, a lower alkyl group, a halo-lower alkyl group, a lower alkoxy group, and a halo-lower alkoxy group.

Among them, a compound in which Ring C is a phenyl group substituted by a halogen atom, a cyano group, a lower alkyl group, a halo-lower alkyl group, a lower alkoxy group or a halo-lower alkoxy group; or a heterocyclyl group substituted by a halogen atom, a cyano group, a lower alkyl group, or a lower alkoxy group is preferred.

A preferred heterocyclyl group includes a 5- or 6-membered heterocyclyl group containing 1 or 2 hetero atoms independently selected from the group consisting of a nitrogen atom, an oxygen atom, and a sulfur atom, or a 9- or 10-membered heterocyclyl group containing 1 to 4 hetero atoms independently selected from the group consisting of a nitrogen atom, an oxygen atom, and a sulfur atom. Specifically, a thienyl group, a pyridyl group, a pyrimidyl group, a pyrazinyl group, pyrazolyl group, a thiazolyl group, a quinolyl group, a tetrazolyl group and an oxazolyl group are preferred.

In a further preferable embodiment, Ring C is a phenyl group substituted by a halogen atom or a cyano group, or a pyridyl group substituted by a halogen atom.

In another preferable embodiment of the present invention, preferred is a compound in which Ring A is

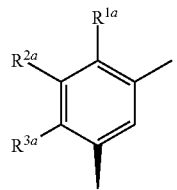

wherein $R^{1a}$ is a halogen atom, a lower alkyl group, or a lower alkoxy group, and $R^{2a}$ and $R^{3a}$ are hydrogen atoms; and Ring B is

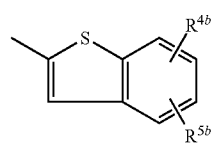

wherein $R^{4b}$ and $R^{5b}$ are each independently a hydrogen atom, a halogen atom, a lower alkyl group, a halo-lower alkyl group, a lower alkoxy group, or a halo-lower alkoxy group.

In another aspect of the present invention, preferable examples of the compound I include a compound represented by the following formula IB:

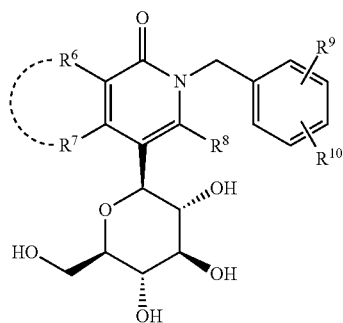

(IB)

wherein $R^8$, $R^9$ and $R^{10}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryloxy group, an arylalkoxy group, a cyano group, a nitro group, an amino group, a mono- or di-alkylamino group, an alkylcarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, or an arylsulfonyl group; and a group represented by:

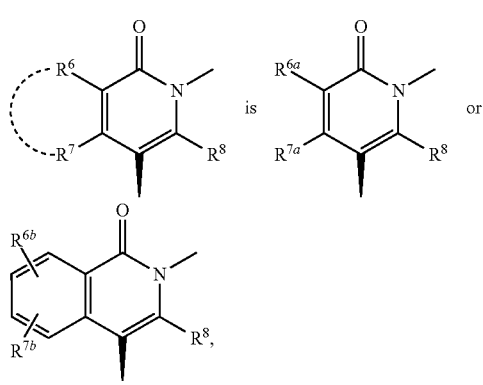

wherein $R^{6a}$ and $R^{7a}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryloxy group, an arylalkoxy group, a cyano group, a nitro group, an amino group, a mono- or di-alkylamino group, an alkylcarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, or an arylsulfonyl group and $R^{6b}$ and $R^{7b}$ are each independently a hydrogen atom, a halogen atom, an alkyl group, a haloalkyl group, or an alkoxy group.

Among the compounds represented by the formula IB, more preferred is a compound in which $R^8$, $R^9$ and $R^{10}$ are each independently a hydrogen atom, a halogen atom, a lower alkyl group, a cycloalkyl group, a hydroxy-lower alkyl group, a halo-lower alkyl group, a lower alkoxy-lower alkyl group, a lower alkoxy group, a cycloalkoxy group, a halo-lower alkoxy group, or a lower alkoxy-lower alkoxy group, and a group represented by:

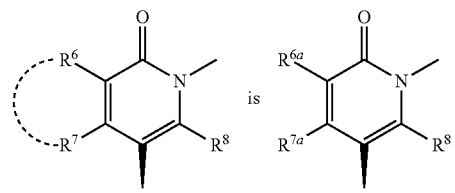

wherein $R^{6a}$, $R^{7a}$ are each independently a hydrogen atom, a halogen atom, a lower alkyl group, a cycloalkyl group, a hydroxy-lower alkyl group, a halo-lower alkyl group, a lower alkoxy-lower alkyl group, a lower alkoxy group, a cycloalkoxy group, a halo-lower alkoxy group, or a lower alkoxy-lower alkoxy group, or a group represented by:

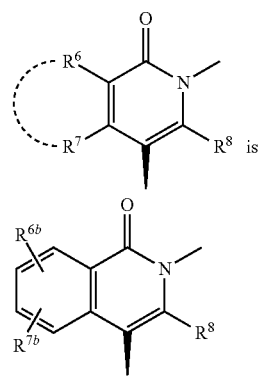

wherein $R^{6b}$ and $R^{7b}$ are each independently a hydrogen atom, a halogen atom, a lower alkyl group, a halo-lower alkyl group, or a lower alkoxy group.

In another aspect of the present invention, preferable examples of the compound I include a compound represented by the following formula IC:

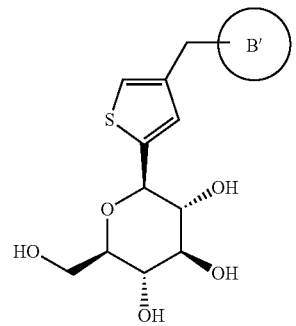

(IC)

wherein Ring B' is an optionally substituted benzene ring, an optionally substituted unsaturated monocyclic heterocyclic ring, or an optionally substituted unsaturated fused heterobicyclic ring.

Preferable examples of Ring B' include a benzene ring and a heterocyclic ring, both of which may have a substituent(s) selected from the group consisting of a halogen atom; a cyano group; a lower alkyl group optionally substituted by a halogen atom; a lower alkoxy group optionally substituted by a halogen atom; a lower alkanoyl group; a mono- or di-lower alkylamino group; a lower alkoxycarbonyl group; a carbamoyl group; a mono- or di-lower alkylcarbamoyl group; a phenyl group optionally substituted by a substituent(s) selected from a halogen atom, a cyano group, a lower alkyl group optionally substituted by a halogen atom, a lower alkoxy group optionally substituted by a halogen atom, a lower alkanoyl group, a mono- or di-lower alkylamino group, a lower alkoxycarbonyl group, a carbamoyl group, or a mono- or di-lower alkylcarbamoyl group; a heterocyclyl group optionally substituted by a substituent(s) selected from a halogen atom, a cyano group, a lower alkyl group optionally substituted by a halogen atom, a lower alkoxy group optionally substituted by a halogen atom, a lower alkanoyl group, a mono- or di-lower alkylamino group, a lower alkoxycarbonyl group, a carbamoyl group, or a mono- or di-lower alkylcarbamoyl group; an alkylene group; and an oxo group.

More preferable examples of Ring B' include a benzene ring which may be substituted by a substituent selected from the group consisting of a halogen atom; a cyano group; a lower alkyl group optionally substituted by a halogen atom; a lower alkoxy group optionally substituted by a halogen atom; a mono- or di-lower alkylamino group; a phenyl group optionally substituted by a halogen atom, a cyano group, a lower alkyl group optionally substituted by a halogen atom, a lower alkoxy group optionally substituted by a halogen atom; a heterocyclyl group optionally substituted by a halogen atom, a cyano group, a lower alkyl group optionally substituted by a halogen atom, a lower alkoxy group optionally substituted by a halogen atom.

Preferred compound of the present invention may be selected from the following group:

1-(β-D-glucopyranosyl)-4-chloro-3-(6-ethylbenzo[b]thiophen-2-ylmethyl)benzene;
1-(β-D-glucopyranosyl)-4-chloro-3-[5-(5-thiazolyl)-2-thienylmethyl]benzene;
1-(β-D-glucopyranosyl)-4-chloro-3-(5-phenyl-2-thienylmethyl)benzene;
1-(β-D-glucopyranosyl)-4-methyl-3-[5-(4-fluorophenyl)-2-thienylmethyl]benzene;
1-(β-D-glucopyranosyl)-4-chloro-3-[5-(2-pyrimidinyl)-2-thienylmethyl]benzene;
1-(β-D-glucopyranosyl)-4-methyl-3-[5-(2-pyrimidinyl)-2-thienylmethyl]benzene;
1-(β-D-glucopyranosyl)-4-chloro-3-[5-(3-cyanophenyl)-2-thienylmethyl]benzene;
1-(β-D-glucopyranosyl)-4-chloro-3-[5-(4-cyanophenyl)-2-thienylmethyl]benzene;
1-(β-D-glucopyranosyl)-4-methyl-3-[5-(6-fluoro-2-pyridyl)-2-thienylmethyl]benzene;
1-(β-D-glucopyranosyl)-4-chloro-3-[5-(6-fluoro-2-pyridyl)-2-thienylmethyl]benzene;
1-(β-D-glucopyranosyl)-4-methyl-3-[5-(3-difluoromethyl-phenyl)-2-thienylmethyl]benzene;
1-(β-D-glucopyranosyl)-4-methyl-3-[5-(3-cyanophenyl)-2-thienylmethyl]benzene;
1-(β-D-glucopyranosyl)-4-methyl-3-[5-(4-cyanophenyl)-2-thienylmethyl]benzene;
1-(β-D-glucopyranosyl)-4-chloro-3-[5-(6-fluoro-3-pyridyl)-2-thienylmethyl]benzene;
1-(β-D-glucopyranosyl)-4-fluoro-3-(5-(3-cyanophenyl)-2-thienylmethyl)benzene;
the pharmaceutically acceptable salt thereof; and the prodrug thereof.

Particularly preferred compounds of the present invention include:

1-(β-D-glucopyranosyl)-4-methyl-3-[5-(3-cyano-phenyl)-2-thienylmethyl]benzene, or a pharmaceutically acceptable salt thereof, or a prodrug thereof;
1-(β-D-glucopyranosyl)-4-methyl-3-[5-(4-cyano-phenyl)-2-thienylmethyl]benzene, or a pharmaceutically acceptable salt thereof, or a prodrug thereof;
1-(β-D-glucopyranosyl)-4-methyl-3-[5-(4-fluoro-phenyl)-2-thienylmethyl]benzene, or a pharmaceutically acceptable salt thereof, or a prodrug thereof;
1-(β-D-glucopyranosyl)-4-chloro-3-[5-(3-cyano-phenyl)-2-thienylmethyl]benzene, or a pharmaceutically acceptable salt thereof, or a prodrug thereof;
1-(β-D-glucopyranosyl)-4-methyl-3-[5-(6-fluoro-2-pyridyl)-2-thienylmethyl]benzene, or a pharmaceutically acceptable salt thereof, or a prodrug thereof;
1-(β-D-glucopyranosyl)-4-chloro-3-[5-(6-fluoro-2-pyridyl)-2-thienylmethyl]benzene, or a pharmaceutically acceptable salt thereof, or a prodrug thereof;
1-(β-D-glucopyranosyl)-4-chloro-3-[5-(6-fluoro-3-pyridyl)-2-thienylmethyl]benzene, or a pharmaceutically acceptable salt thereof, or a prodrug thereof; and
1-(β-D-glucopyranosyl)-4-fluoro-3-(5-(3-cyanophenyl)-2-thienylmethyl)benzene, or a pharmaceutically acceptable salt thereof, or a prodrug thereof.

Abbreviations used in the specification, particularly the Schemes and Examples, are as follows
AcOEt=Ethyl acetate
CPME=Cyclopentyl methyl ether
DI (water)=Deionized (water)
DMAP=4-Dimethylaminopyridine
HPLC=High Pressure Liquid Chromatography
IPA=Isopropyl Alcohol
2-Me-THF=2-Methyl-tetrahydrofuran
MPLC=Medium Pressure Liquid Chromatography
MTBE=Methyl-t-butyl Ether
n-BuLi=n-Butyl lithium
Pd/C=Palladium on carbon
$Pd(OAc)_2/Et_3SiH$=Palladium acetate and triethylsilane
RaNi=RANEY® nickel (aluminum nickel alloy)
RBF=Round Bottom Flask
TEA=Triethylamine
THF=Tetrahydrofuran
TMEDA=Tetramethylethylenediamine
TMS=Trimethylsilyl
TMSBr=Trimethylsilyl bromide
$TMSCH_2$=Trimethylsilyl-$CH_2$—

As used herein, unless otherwise noted, the term "isolated form" shall mean that the compound is present in a form which is separate from any solid mixture with another compound(s), solvent system or biological environment. In an embodiment, the product prepared according to the process described herein (more particularly, a compound of formula (I), preferably a compound of formula (I-S), or a compound of formula (I-K)) is prepared as an isolated form.

As used herein, unless otherwise noted, the term "substantially pure" shall mean that the mole percent of impurities in the isolated compound is less than about 5 mole percent, preferably less than about 2 mole percent, more preferably, less than about 0.5 mole percent, most preferably, less than about 0.1 mole percent.

In an embodiment, the present invention is directed to a process for the preparation of a compound of formula (I), wherein the compound of formula (I) is substantially pure. In another embodiment, the present invention is directed to a process for the preparation of a compound of formula (I-S), wherein the compound of formula (I-S) is substantially pure. In another embodiment, the present invention is directed to a process for the preparation of a compound of formula (I-K), wherein the compound of formula (I-K) is substantially pure.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent.

In an embodiment, the present invention is directed to a process for the preparation of a compound of formula (I), wherein the compound of formula (I) is substantially free of corresponding salt forms. In another embodiment, the present invention is directed to a process for the preparation of a compound of formula (I-S), wherein the compound of formula (I-S) is substantially free of corresponding salt forms. In another embodiment, the present invention is directed to a process for the preparation of a compound of formula (I-K), wherein the compound of formula (I-K) is substantially free of corresponding salt forms.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The compound of formula (I) of the present invention exhibits an excellent inhibitory activity against sodium-dependent glucose transporter, and an excellent blood glucose lowering effect. Therefore, the compound of the present invention is useful for treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension. In particular, the compound of the present invention is useful in the treatment or the prophylaxis of diabetes mellitus (type 1 and type 2 diabetes mellitus, etc.), diabetic complications (such as diabetic retinopathy, diabetic neuropathy, diabetic nephropathy) or obesity, or is useful in the treatment of postprandial hyperglycemia.

The compound of formula (I) of the present invention or a pharmaceutically acceptable salt thereof may be administered either orally or parenterally, and can be used in the form of a suitable pharmaceutical preparation. Suitable pharmaceutical preparation for oral administration includes, for example, solid preparation such as tablets, granules, capsules, powders, etc., or solution preparations, suspension preparations, or emulsion preparations, etc. Suitable pharmaceutical preparation for parenteral administration includes, for example, suppositories; injection preparations and intravenous drip preparations using distilled water for injection, physiological saline solution or aqueous glucose solution; or inhalant preparations.

The dosage of the present compound of formula (I) or a pharmaceutically acceptable salt thereof may vary according to the administration routes, ages, body weight, conditions of a patient, or kinds and severity of a disease to be treated, and it is usually in the range of about 0.01 to 300 mg/kg/day, or any amount or range therein, preferably in the range of about 0.1 to 50 mg/kg/day, or any amount or range therein, preferably in the range of about 0.1 to 30 mg/kg/day, or any amount or range therein. In an embodiment, the compound of formula (I) or pharmaceutically acceptable salt thereof is administered to a subject in need thereof in a dosage in the range of from about 0.01 mg/kg/day to about 15 mg/kg/day, or any amount or range therein.

The compound of the formula I may be used, if necessary, in combination with one or more of other antidiabetic agents, one or more agents for treating diabetic complications, and/or one or more agents for treatment of other diseases. The present compound and these other agents may be administered in the same dosage form, or in a separate oral dosage form or by injection.

The other antidiabetic agents include, for example, antidiabetic or antihyperglycemic agents including insulin, insulin secretagogues, or insulin sensitizers, or other antidiabetic agents having an action mechanism different from SGLT inhibition, and 1, 2, 3 or 4 of these other antidiabetic agents may preferably be used. Concrete examples thereof are biguanide compounds, sulfonylurea compounds, α-glucosidase inhibitors, PPARγ agonists (e.g., thiazolidinedione compounds), PPARα/γ dual agonists, dipeptidyl peptidase IV (DPP4) inhibitors, mitiglinide compounds, and/or nateglinide compounds, and insulin, glucagon-like peptide-1 (GLP-1), PTP1B inhibitors, glycogen phosphorylase inhibitors, RXR modulators, and/or glucose 6-phosphatase inhibitors.

The agents for treatment of other diseases include, for example, an anti-obesity agent, an antihypertensive agent, an antiplatelet agent, an anti-atherosclerotic agent and/or a hypolipidemic agent.

The SGLT inhibitors of the formula I may be used in combination with agents for treatment of diabetic complications, if necessary. These agents include, for example, PKC inhibitors and/or ACE inhibitors.

The dosage of those agents may vary according to ages, body weight, and conditions of patients, and administration routes, dosage forms, etc.

These pharmaceutical compositions may be orally administered to mammalian species including human beings, apes, dogs, etc., for example, in the dosage form of tablet, capsule, granule or powder, or parenterally administered in the form of injection preparation, or intranasally, or in the form of transdermal patch.

One skilled in the art will recognize that, where not otherwise specified, the reaction step(s) is performed under suitable conditions, according to known methods, to provide the desired product.

One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same or different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—containing groups of the formula —C(O)O—R wherein R is for example methyl, ethyl, t-butyl, benzyl, phenylethyl, $CH_2$=CH—$CH_2$—, and the like; amides—containing groups of the formula —C(O)—R' wherein R' is for example methyl, phenyl, trifluoromethyl, and the like; N-sulfonyl derivatives—containing groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, acetyl, benzoyl, pivaloyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One skilled in the art will recognize that in any of the processes described herein, reactive substituents on the compounds of formula (I), such as hydroxy groups, oxo groups, carboxy groups, and the like, are preferably protected and subsequently de-protected, according to known methods, at suitable points along the synthesis route.

The present invention is directed to a process for the preparation of compounds of formula (I) as outlined in Scheme A below.

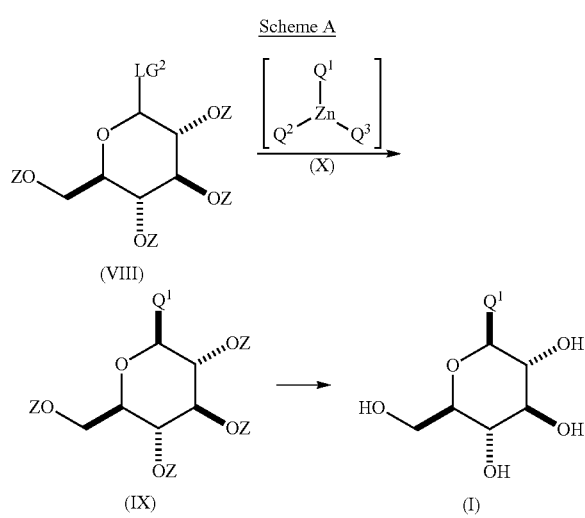

Accordingly, a suitably substituted compound of formula (VIII), wherein LG² is a suitably selected leaving group such as bromo, chloro, iodo, and the like, preferably bromo, and wherein each Z is an independently selected oxygen protecting group, for example Z may selected from the group consisting of benzyl, benzoyl, pivaloyl, isobutyryl, p-methoxybenzyl, and the like; preferably, each Z protecting group is the same, more preferably, each Z is pivaloyl, a known compound or compound prepared by known methods; is reacted with a suitably substituted compound of formula (X), a known compound or compound prepared by known methods; wherein the compound of formula (X) is selected from the group consisting of (a) a suitably substituted organozinc halide wherein Q¹ is

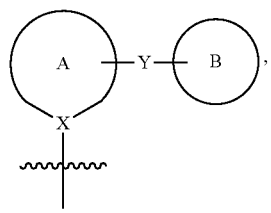

Q² is a suitably selected halogen such as Br, I, and the like, and Q³ is absent;

(b) a suitably substituted di-substituted zinc derivative, wherein Q¹ and Q² are the same and are each

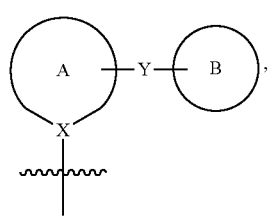

and Q³ is absent;

(c) a suitably substituted organozincate derivative, wherein Q¹ is

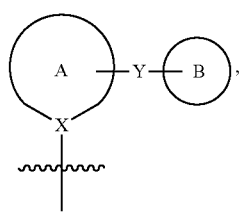

and Q² and Q³ are each an independently selected non-transferrable group such as alkyl, cycloalkyl, TMSCH₂, and the like; and (d) a suitably selected organozincate derivative, wherein Q¹, Q² and Q³

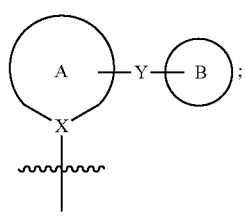

are the same and are each to yield the corresponding compound of formula (IX); which compound of formula (IX) is then de-protected according to known methods, to yield the corresponding compound of formula (I).

One skilled in the art will recognize that when the compound of formula (X) is an organozincate derivative as defined in (c) and (d) above, the Zn of said organozincate derivative carries a negative charge, and therefore the organozincate derivative is present in conjunction with a suitable counterion, such as lithium or magnesium.

Organozinc derivatives of formula (X) wherein Q¹ is

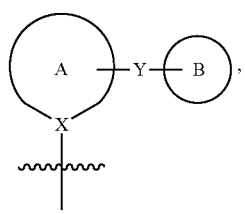

Q² is a suitably selected halogen such as Br, I, and the like, and Q³ is absent; may be prepared, for example, according to Scheme B as outlined below:

Scheme B

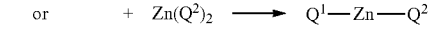
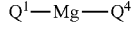

more particularly, by transmetalation, reacting a suitably substituted organolithium or organomagnesium compound (wherein $Q^4$ is a suitably selected halogen such as bromo, chloro, iodo, and the like) with a suitably selected zinc halide. One skilled in the art will recognize that in the alternatively, a suitably selected zinc sulfonate may be substituted for the zinc halide and reacted as outlined in Scheme B above to yield the desired organohalide of formula (X).

Alternatively, organozinc derivatives of formula (X) wherein $Q^1$ is

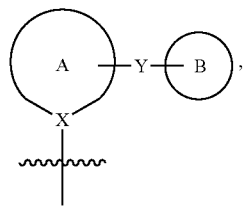

$Q^2$ is a suitably selected halogen such as Br, I, and the like, and $Q^3$ is absent; may be prepared, for example, according to Scheme C as outlined below:

Scheme C

more particularly, by direct insertion of activated zinc into a suitably substituted aryl halide.

Di-substituted zinc derivatives of formula (X), wherein $Q^1$ and $Q^2$ are the same and are each

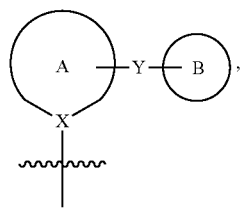

and $Q^3$ is absent may be prepared, for example, according to Scheme D, as outlined below:

Scheme D

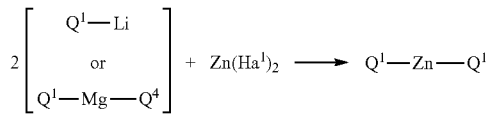

more particularly, by transmetalation, reacting two equivalents of a suitably substituted organolithium or organomagnesium compound (wherein $Q^4$ is a suitably selected halogen such as bromo, chloro, iodo, and the like) with a suitably selected zinc halide, a compound of the formula $Zn(Ha^1)_2$, wherein each $Ha^1$ is a suitably selected halogen such as Br, I, and the like, and wherein preferably both $Ha^1$ halogens are the same; or zinc halide.lithium halide complex of the formula $Zn(Ha^1)_2.Li(Ha^1)$, such as $ZnB_2.LiBr$, and the like. One skilled in the art will recognize that in the alternatively, a suitably selected zinc sulfonate may be substituted for the zinc halide and reacted as outlined in Scheme D above, to yield the desired di-substituted zinc derivative of formula (X).

Organozincate derivatives of formula (X), wherein $Q^1$, $Q^2$ and $Q^3$ are the same and are each

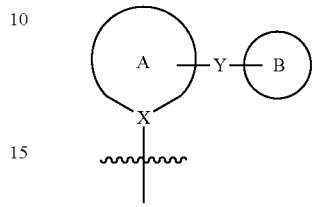

may be similarly prepared, for example, according to Scheme E, as outlined below:

Scheme E

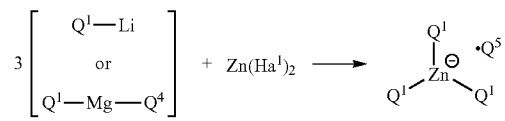

more particularly, by transmetalation, reacting three equivalents of a suitably substituted organolithium or organomagnesium compound (wherein $Q^4$ is a suitably selected halogen such as bromo, chloro, iodo, and the like) with a suitably selected zinc halide, a compound of the formula $Zn(Ha^1)_2$, wherein each $Ha^1$ is a suitably selected halogen such as Br, I, and the like, and wherein preferably both $Ha^1$ halogens are the same or zinc halide.lithium halide complex of the formula $Zn(Ha^1)_2.Li(Ha^1)$, such as $ZnB_2.LiBr$, and the like. One skilled in the art will recognize that in the alternatively, a suitably selected zinc sulfonate may be substituted for the zinc halide and reacted as outlined in Scheme E above, to yield the desired organozincate derivative of formula (X). One skilled in the art will further recognize that for the organozincate derivatives as prepared in Scheme E above, the Zn carries a negative charge and therefore, the organozincate derivative is present with a suitable counterion, such as lithium or magnesium, as denoted by the variable $.Q^5$.

Mixed organozincate derivatives of formula (X), wherein $Q^1$ is

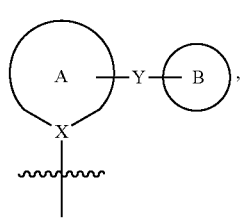

and $Q^2$ and $Q^3$ are each an independently selected non-transferrable group such as alkyl, cycloalkyl, $TMSCH_2$, and the like, may be prepared, for example, according to Scheme F, as outlined below:

Scheme F

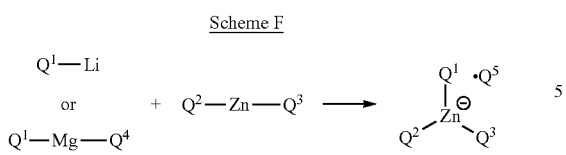

more particularly, by reacting an organolithium or organomagnesium compound (wherein $Q^4$ is a suitably selected halogen such as bromo, chloro, iodo, and the like) and a di-substituted zinc derivative. One skilled in the art will recognize that for the organozincate derivatives as prepared in Scheme F above, the Zn carries a negative charge and therefore, the organozincate derivative is present with a suitable counterion, such as lithium or magnesium, as denoted by the variable $.Q^5$.

The organolithium ($Q^1$-Li) and organomagnesium ($Q^1$-Mg-$Q^4$) compounds reacted in Scheme B through Scheme F above are known compounds or compounds which may be prepared according to known methods. For example, organolithium compounds of the formula $Q^1$-Li may be prepared by lithiation of a $Q^1$ substituted halide (e.g. Br, I), sulfide, selenide, telluride, stannane or other precursors, with an alkyllithium solution such as n-butyllithium, and the like, in a suitably selected organic solvent.

Organomagnesium compounds of the formula $Q^1$-Mg-$Q^4$ may be similarly prepared by reacting a $Q^1$-halide (e.g. Br) with an alkyl magnesium halide such as a primary, secondary, tertiary cyclic or acyclic alkyl magnesium bromide or chloride, in a suitable selected organic solvent. Alternatively, organomagnesium compounds of the formula $Q^1$-Mg-$Q^4$ may be prepared by reacting a $Q^1$-halide (e.g. Br) with activated magnesium.

One skilled in the art will recognize that di-organylmagnesium compounds of the formula Mg($Q^1$)$_2$ may be substituted for the compounds of the formula $Q^1$-Mg-$Q^4$ in the reactions described in Scheme B through Scheme F above to yield the desired compounds of formula (X). Di-organylmagnesium compounds of the formula Mg($Q^1$)$_2$ are present in ethereal solutions of Grignard reagents, according to the Schlenk equilibrium, as shown in Scheme G, below Scheme G

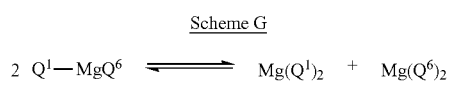

wherein $Q^6$ is a suitably selected halogen such as bromo, chloro, iodo, and the like; as would be readily recognized by those skilled in the art.

One skilled in the art will further recognize that aryl magnesiate derivatives of the formula ($Q^1$)$_3$-MgLi may alternatively be used in the processes as described in Schemes B through F above, and may be prepared from suitably substituted magnesiate derivatives as outlined in Scheme H, below Scheme H

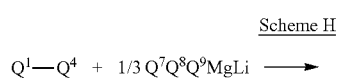

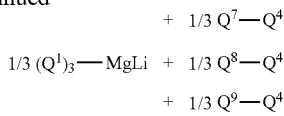

more particularly, by transmetalation of a suitably substituted $Q^1$-$Q^4$ aryl halide (wherein $Q^4$ is a suitably selected halogen such as bromo, chloro, iodo, and the like), reacting said compound with ⅓ equivalent of a suitably substituted magnesiate (wherein $Q^7$, $Q^8$ and $Q^9$ are each an independently selected alkyl or cyloalkyl group).

In yet another example, a di-substituted zinc derivative of formula (X)

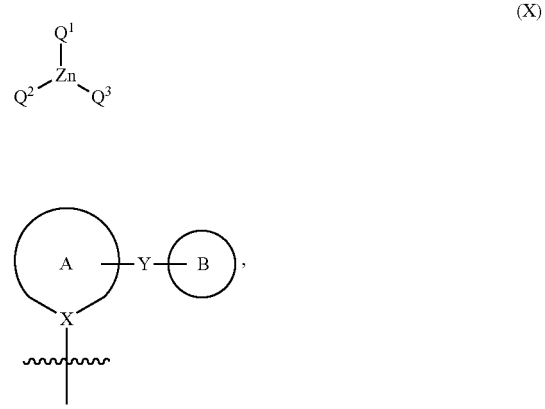

wherein $Q^1$ and $Q^2$ are the same and are each and $Q^3$ is absent, may be prepared according to Scheme J, as outlined below.

Scheme J

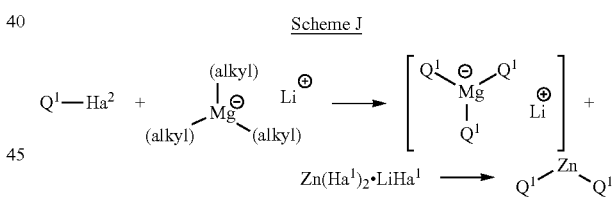

Accordingly, a suitably substituted organo-halide compound of the formula $Q^1$-Ha$^2$, wherein Ha$^2$ is a suitably selected halogen such as Br, I, and the like, preferably I, is reacted with a suitably selected lithium trialkyl magnesate, such as lithium dibutyl hexylmagnesate, lithium tributylmagnesate, lithium trihexylamagensate, lithium hexyl di(sec-butyl)magnesate, and the like, preferably lithium dibutyl hexylmagnesate, a known compound or compound prepared by known methods; in a suitably selected anhydrous organic solvent or mixture of anhydrous organic solvents, such as anhydrous toluene, anhydrous n-dibutylether, fluorobenzene, chlorobenzene, trifluorotoleune, cyclopentylmethylether, and the like; to yield the corresponding lithium tri-substituted magnesate; which compound is preferably not isolated.

The lithium tri-substituted magnesate is then reacted with a suitably selected zinc halide (a compound of the formula Zn(Ha$^1$)$_2$, wherein each Ha$^1$ is a suitably selected halogen such as Br, I, and the like) or zinc halide.lithium halide complex, such as ZnBr$_2$.LiBr, and the like or zinc halide diamine complex such as zinc bromide bis pyridine complex, and the like; preferably a zinc halide.lithium halide complex, more preferably, ZnBr$_2$.LiBr; in a suitably selected anhydrous organic solvent or mixture of anhydrous organic solvents, such as anhydrous toluene, anhydrous n-dibutylether, anhydrous cyclopentyl methylether, and the like; preferably in the same solvent or mixture of solvents as used in the previous reaction step; to yield the corresponding di-substituted zinc derivative.

In an embodiment of the present invention, the di-substituted zinc derivative of formula (X), preferably prepared according to the process outlined in Scheme J above, is a compound of formula (X-P)

(X-P)

In another embodiment of the present invention, the di-substituted zinc derivative of formula (X), preferably prepared according to the process outlined in Scheme J above, is a compound of formula (X-P) selected from the group consisting of a compound of formula (X-S)

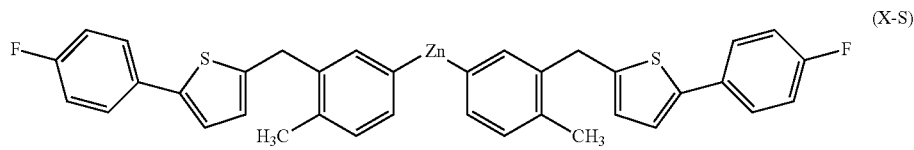

(X-S)

and a compound of formula (X-K)

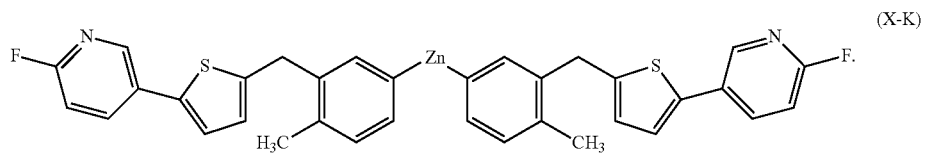

(X-K)

Additional methods for the preparation of organozinc derivatives, such as the compounds of formula (X) are known in the art, for example as described in organic chemistry texts such as "Organic Reactions", Volume 58, Edited by Larry E. Overman, et al., 2001, Published by John Wiley & Sons, Inc. (See Chapter 2: Preparation and Application of Functionalized Organozinc Compounds, Knochel, P., et al. pages 417-490); MONGIN, F., et al., *Tetrahedron Lett.*, 2005, pp 7989-7992, Vol. 46; and KITAGAWA, K., et al., *Angew. Chem. Int. Ed.*, 2000, pp 2481-2493, Vol. 39.

In an embodiment, the present invention is directed to a process for the preparation of compounds of formula (I) as outlined in Scheme 1, below.

Scheme 1

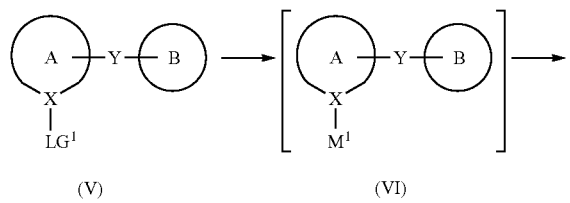

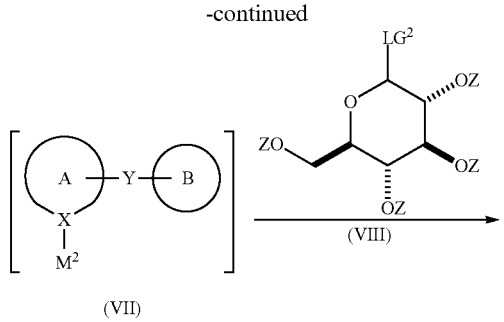

(VII)

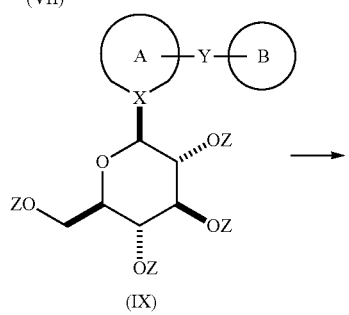

(IX)

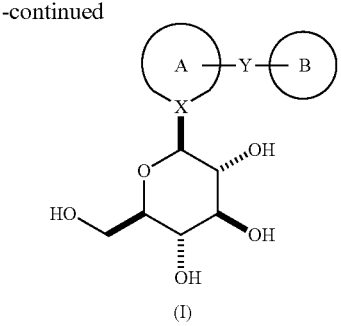

(I)

Accordingly, a suitably substituted compound of formula (V), wherein LG$^1$ is a suitably selected leaving group such as bromo, iodo, and the like, preferably LG$^1$ is bromo or iodo, a known compound or compound prepared by known methods, is reacted with a suitably selected organo-lithium reagent such as trimethylsilylmethyl lithium, n-hexyl lithium, sec-butyl lithium, n-butyllithium, t-butyllithium, methyl lithium, and the like, preferably n-hexyl lithium; wherein the organolithium reagent is preferably present in an amount in the range of from about 0.5 to about 2.0 molar equivalents, preferably in an amount in the range of from about 1.0 to about 1.2 molar equivalents;

in a mixture of a suitably selected ether solvent and a suitably selected hydrocarbon solvent, wherein the ether solvent is for example, diethyl ether, diisopropyl ether, di-n-butyl ether, MTBE, 2-methyl-THF, cyclopentylmethyl ether, and the like, preferably di-n-butyl ether or cyclopentyl methyl ether; and wherein hydrocarbon solvent is for example toluene, fluorobenzene, chlorobenzene, benzotrifluoride, and the like, preferably toluene; preferably at a temperature less than about room temperature, more preferably at a temperature in the range of from about −78° C. to about room temperature; to yield the corresponding compound of formula (VI), wherein $M^1$ is lithium. Preferably, the compound of formula (VI) is not isolated.

The compound of formula (VI) is reacted with a suitably selected zinc salt such as zinc dibromide ($ZnBr_2$), zinc diiodide ($ZnI_2$), zinc ditriflate, and the like, preferably $ZnBr_2$; or with an amine complex of zinc halide such as pyridine zinc bromide complex, N-methylmorpholine zinc bromide complex, and the like; wherein the zinc salt or amine complex of zinc halide is preferably present in an amount in the range of from about 0.33 to about 3.0 molar equivalents, more preferably in an amount in the range of from about 0.33 to about 1.0 molar equivalents, more preferably in an amount of about 0.5 molar equivalents;

in a mixture of a suitably selected ether solvent and a suitably selected hydrocarbon solvent, wherein the ether solvent is for example, diethyl ether, diisopropyl ether, di-n-butyl ether, MTBE, cyclopentylmethyl ether, and the like, preferably di-n-butyl ether or cyclopentyl methyl ether; and wherein hydrocarbon solvent is for example toluene, fluorobenzene, chlorobenzene, and the like, preferably toluene; preferably in the same mixture of solvents as used in the previous reaction step; to yield the corresponding compound of formula (VII), wherein $M^2$ is the corresponding zinc species, for example when the zinc salt is $ZnBr_2$, then in the compound of formula (VII), $M^2$ is ZnBr; wherein the zinc salt is $ZnI_2$, then in the compound of formula (VII), $M^2$ is ZnI; wherein the zinc salt is zinc ditriflate, then in the compound of formula (VII), $M^2$ is zinc triflate. Preferably, the compound of formula (VII) is not isolated.

Preferably, the compound of formula (VI) is reacted with a zinc salt, in the presence of a suitably selected amine or lithium salt such as lithium bromide, lithium iodide, pyridine, N-methyl morpholine, 2,6-lutidine, TMEDA, and the like; wherein the amine or lithium salt is preferably present in an amount in the range of from about 1.0 to about 2.0 molar equivalent.

The compound of formula (VII) is reacted with a suitably substituted compound of formula (VIII), wherein $LG^2$ is a suitably selected leaving group such as bromo, chloro, iodo, and the like, preferably bromo; and wherein each Z is independently a suitably selected oxygen protecting group, for example Z may selected from the group consisting of benzyl, benzoyl, pivaloyl, isobutyryl, p-methoxy-benzyl, and the like, preferably, each Z protecting group is the same, more preferably each Z is pivaloyl, a known compound or compound prepared by known methods; wherein the compound of formula (VIII) is preferably present in an amount in the range of from about 0.5 to about 3.0 molar equivalents, or any amount or range therein, more preferably in an amount in the range of from about 0.8 to about 1.25 molar equivalents, or any amount or range therein, more preferably in an amount of about 1.0 to about 1.1 molar equivalents;

in a mixture of a suitably selected ether solvent and a suitably selected hydrocarbon solvent, wherein the ether solvent is for example, diethyl ether, di-n-butyl ether, MTBE, 2-methyl-THF, diiodopropyl ether, cyclopentylmethyl ether, and the like, preferably di-n-butyl ether or cyclopentyl methyl ether; and wherein hydrocarbon solvent is for example toluene, fluorobenzene, chlorobenzene, benzotrifluoride, and the like, preferably toluene; preferably in the same mixture of solvents as used in the previous reaction step; at a temperature in the range of from about room temperature to about reflux temperature, more preferably at a temperature in the range of from about 60° C. to about 95° C.; to yield the corresponding compound of formula (IX).

Preferably, the compound of formula (VIII), as a solution in a suitably selected hydrocarbon solvent, more preferably a suitably selected aromatic hydrocarbon, such as toluene, xylene, fluorobenzene, chlorobenzene, benzotrifluoride, and the like; is added to a solution of the compound of formula (VII) in a suitably selected ether solvent other than THF, such as diisopropyl ether, 1,4-dioxane, 2-methyl-THF, MTBE, cyclopentyl methyl ether (CPME), di-n-butyl ether, and the like, more preferably CPME or di-n-butyl ether. Preferably, the final solvent mixture is present in a volume ratio of ether solvent:hydrocarbon solvent of from about 1: to about 1:3.

Alternatively, a suitably substituted di-substituted zinc derivative, a compound of formula (X)

wherein $Q^1$ and $Q^2$ are the same and are each

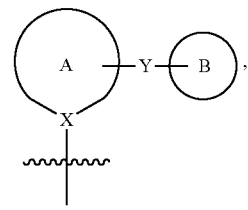

and $Q^3$ is absent (prepared for example according to the process outlined in Scheme J above) is reacted with a suitably substituted compound of formula (VIII), wherein $LG^2$ is a suitably selected leaving group such as bromo, chloro, iodo, and the like, preferably bromo; and wherein each Z is independently a suitably selected oxygen protecting group, for example Z may selected from the group consisting of benzyl, benzoyl, pivaloyl, isobutyryl, p-methoxy-benzyl, and the like, preferably, each Z protecting group is the same, more preferably each Z is pivaloyl, a known compound or compound prepared by known methods; wherein the compound of formula (VIII) is preferably present in an amount in the range of from about 0.5 to about 3.0 molar equivalents, or any amount or range therein, more preferably in an amount in the range of from about 0.8 to about 1.25 molar equivalents, or any amount or range therein;

in a suitably selected solvent such as toluene, or a mixture of a suitably selected ether solvent and a suitably selected hydrocarbon solvent, wherein the ether solvent is for example, diethyl ether, di-n-butyl ether, MTBE, 2-methyl-THF, diiodopropyl ether, cyclopentylmethyl ether, and the like, preferably di-n-butyl ether or cyclopentyl methyl ether; and wherein hydrocarbon solvent is for example toluene, fluorobenzene, chlorobenzene, benzotrifluoride, and the like, preferably toluene; preferably in the same mixture of solvents as used in the previous reaction step; at a temperature in the range of from about room temperature to about reflux temperature, more preferably at a temperature in the range of from about 60° C. to about 100° C.; to yield the corresponding compound of formula (IX).

In an embodiment of the present invention, the di-substituted zinc derivative of formula (X) is a compound of formula (X-P)

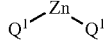
(X-P)

wherein $Q^1$ is as herein defined, and wherein both $Q^1$ groups are the same. In another embodiment of the present invention, the di-substituted zinc derivative of formula (X) is selected from the group consisting of a compound of formula (X-S)

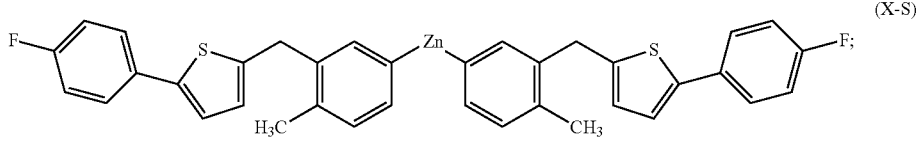
(X-S)

and a compound of formula (X-K)

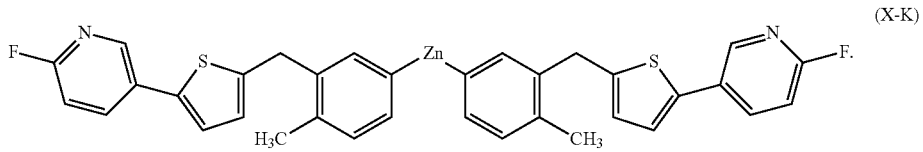
(X-K)

The compound of formula (IX) is de-protected according to known methods, to yield the corresponding compound of formula (I). For example, wherein each Z is pivaloyl, the compound of formula (IX) may be de-protected by reacting with a suitably selected alkoxide or hydroxide base such as sodium methoxide, sodium ethoxide, lithium hydroxide, and the like, in a suitably selected solvent such as methanol, ethanol, and the like, to yield the corresponding compound of formula (I).

One skilled in the art will recognize that, depending on the particular protecting group Z, other reagents may be used in the de-protection step including, but not limited to, Pd/C, Pd(OH)$_2$, PdCl$_2$, Pd(OAc)$_2$/Et$_3$SiH, RaNi, a suitably selected acid, a suitably selected base, fluoride, and the like.

The compound of formula (I) is preferably isolated according to known methods, for example by extraction, filtration or column chromatography. The compound of formula (I) is further, preferably purified according to known methods, for example by recrystallization.

In another embodiment, the present invention is directed to a process for the preparation of a compound of formula (I-S), as outlined in Scheme 2, below.

Scheme 2

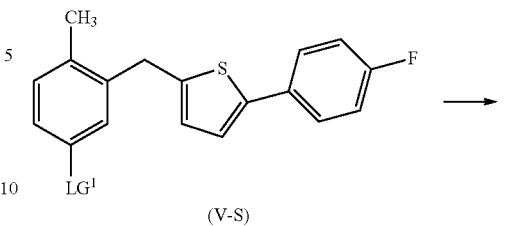
(V-S)

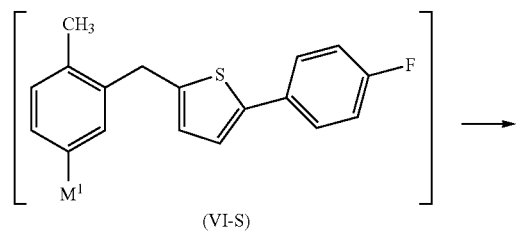
(VI-S)

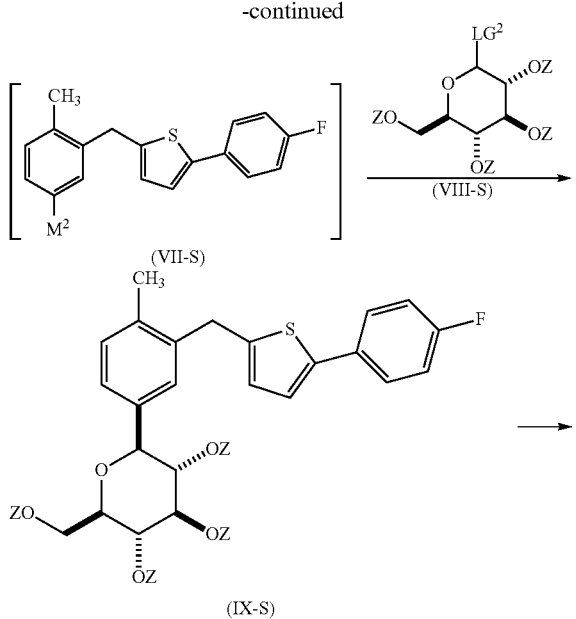
(VII-S)
(VIII-S)
(IX-S)

-continued

-continued

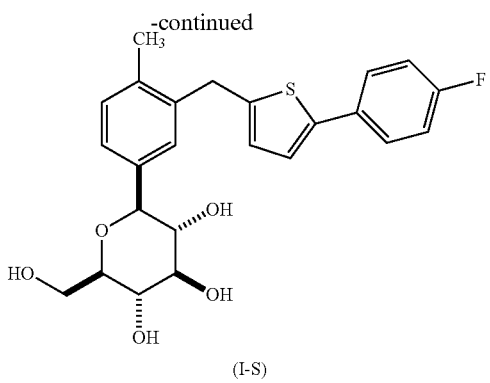
(I-S)

Accordingly, a suitably substituted compound of formula (V-S), wherein $LG^1$ is a suitably selected leaving group such as bromo, iodo, and the like, preferably $LG^1$ is bromo or iodo, a known compound or compound prepared by known methods, is reacted with a suitably selected organo-lithium reagent such as trimethylsilylmethyl lithium, n-hexyl lithium, sec-butyl lithium, n-butyllithium, t-butyllithium, methyl lithium, and the like, preferably n-hexyl lithium; wherein the organo-lithium reagent is preferably present in an amount in the range of from about 0.5 to about 2.0 molar equivalents, preferably in an amount in the range of from about 1.0 to about 1.2 molar equivalents;

in a mixture of a suitably selected ether solvent and a suitably selected hydrocarbon solvent, wherein the ether solvent is for example, diethyl ether, diisopropyl ether, di-n-butyl ether, MTBE, cyclopentylmethyl ether, and the like, preferably di-n-butyl ether or cyclopentyl methyl ether; and wherein hydrocarbon solvent is for example toluene, fluorobenzene, chlorobenzene, benzotrifluoride, and the like, preferably toluene; preferably at a temperature less than about room temperature, more preferably at a temperature in the range of from about −78° C. to about room temperature; to yield the corresponding compound of formula (VI-S), wherein $M^1$ is lithium. Preferably, the compound of formula (VI-S) is not isolated.

The compound of formula (VI-S) is reacted with a suitably selected zinc salt such as zinc dibromide ($ZnBr_2$), zinc diiodide ($ZnI_2$), zinc ditriflate, and the like, preferably $ZnBr_2$; or with an amine complex of zinc halide such as pyridine zinc bromide complex, N-methylmorpholine zinc bromide complex, and the like; wherein the zinc salt or amine complex of zinc halide is preferably present in an amount in the range of from about 0.33 to about 3.0 molar equivalents, more preferably in an amount in the range of from about 0.33 to about 1.0 molar equivalents, more preferably in an amount of about 0.5 molar equivalents;

in a mixture of a suitably selected ether solvent and a suitably selected hydrocarbon solvent, wherein the ether solvent is for example, diethyl ether, diisopropyl ether, di-n-butyl ether, MTBE, cyclopentylmethyl ether, and the like, preferably di-n-butyl ether or cyclopentyl methyl ether; and wherein hydrocarbon solvent is for example toluene, fluorobenzene, chlorobenzene, and the like, preferably toluene; preferably in the same mixture of solvents as used in the previous reaction step; to yield the corresponding compound of formula (VII), wherein $M^2$ is the corresponding zinc species, for example when the zinc salt is $ZnBr_2$, then in the compound of formula (VII-S), $M^2$ is ZnBr; wherein the zinc salt is $ZnI_2$, then in the compound of formula (VII-S), $M^2$ is ZnI; wherein the zinc salt is zinc ditriflate, then in the compound of formula (VII-S), $M^2$ is zinc triflate. Preferably, the compound of formula (VII-S) is not isolated.

Preferably, the compound of formula (VI-S) is reacted with a zinc salt, in the presence of a suitably selected amine or lithium salt such as lithium bromide, lithium iodide, pyridine, N-methyl morpholine, 2,6-lutidine, TMEDA, and the like; wherein the amine or lithium salt is preferably present in an amount in the range of from about 1.0 to about 2.0 molar equivalent.

The compound of formula (VII-S) is reacted with a suitably substituted compound of formula (VIII-S), wherein $LG^2$ is a suitably selected leaving group such as bromo, chloro, iodo, and the like, preferably bromo; and wherein each Z is independently a suitably selected oxygen protecting group, for example Z may selected from the group consisting of benzyl, benzoyl, pivaloyl, isobutyryl, p-methoxy-benzyl, and the like; preferably, each Z protecting group is the same, more preferably each Z is pivaloyl, a known compound or compound prepared by known methods; wherein the compound of formula (VIII-S) is preferably present in an amount in the range of from about 0.5 to about 3.0 molar equivalents, or any amount or range therein, more preferably in an amount in the range of from about 0.8 to about 1.25 molar equivalents, or any amount or range therein, more preferably in an amount of about 1.0 to about 1.1 molar equivalents;

in a mixture of a suitably selected ether solvent and a suitably selected hydrocarbon solvent, wherein the ether solvent is for example, diethyl ether, di-n-butyl ether, MTBE, 2-Me-THF, cyclopentylmethyl ether, diiodopropyl ether, and the like, preferably di-n-butyl ether or cyclopentyl methyl ether; and wherein hydrocarbon solvent is for example toluene, fluorobenzene, chlorobenzene, benzotrifluoride, and the like, preferably toluene; preferably in the same mixture of solvents as used in the previous reaction step; at a temperature in the range of from about room temperature to about reflux temperature, more preferably at a temperature in the range of from about 60° C. to about 95° C.; to yield the corresponding compound of formula (IX-S).

Preferably, the compound of formula (VIII-S), as a solution in a suitably selected hydrocarbon solvent, more preferably a suitably selected aromatic hydrocarbon, such as toluene, xylene, fluorobenzene, chlorobenzene, benzotrifluoride, and the like; is added to a solution of the compound of formula (VII) in a suitably selected ether solvent other than THF, such as diisopropyl ether, 1,4-dioxane, 2-methyl-THF, MTBE, cyclopentyl methyl ether (CPME), di-n-butyl ether, and the like, more preferably CPME or di-n-butyl ether. Preferably, the final solvent mixture is present in a volume ratio of ether solvent:hydrocarbon solvent of from about 1:1 to about 1:3.

The compound of formula (IX-S) is de-protected according to known methods, to yield the corresponding compound of formula (I-S). For example, wherein each Z is pivaloyl, the compound of formula (IX-S) may be de-protected by reacting with a suitably selected alkoxide or hydroxide base such as sodium methoxide, sodium ethoxide, lithium hydroxide, and the like, in a suitably selected solvent such as methanol, ethanol, and the like, to yield the corresponding compound of formula (I-S).

One skilled in the art will recognize that, depending on the particular protecting group Z, other reagents may be used in the de-protection step including, but not limited to, Pd/C, $Pd(OH)_2$, $PdCl_2$, $Pd(OAc)_2/Et_3SiH$, RaNi, a suitably selected acid, a suitably selected base, fluoride, and the like.

The compound of formula (I-S) is preferably isolated according to known methods, for example by extraction, filtration or column chromatography. The compound of formula (I) is further, preferably purified according to known methods, for example by recrystallization.

In another embodiment, the present invention is directed to a process for the preparation of a compound of formula (I-K), as outlined in Scheme 3, below.

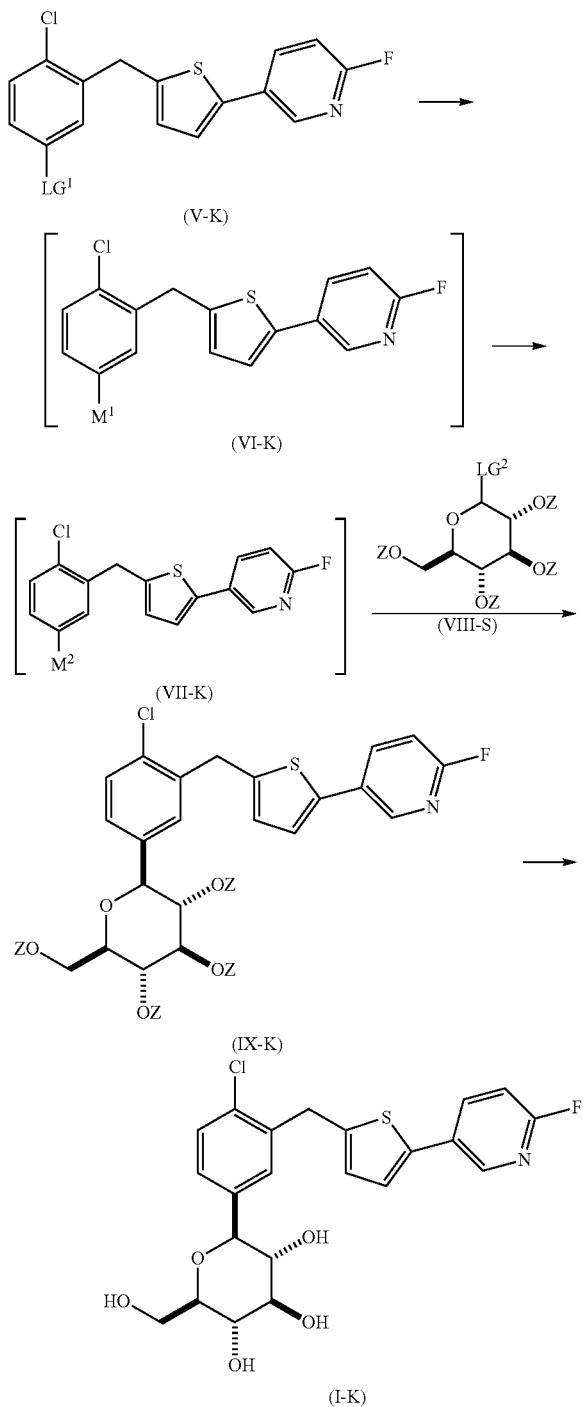

Accordingly, a suitably substituted compound of formula (V-K), wherein LG¹ is a suitably selected leaving group such as bromo, iodo, and the like, preferably LG¹ is bromo or iodo, a known compound or compound prepared by known methods, is reacted with a suitably selected organo-lithium reagent such as trimethylsilylmethyl lithium, n-hexyl lithium, sec-butyl lithium, n-butyllithium, t-butyllithium, methyl lithium, and the like, preferably n-hexyl lithium; wherein the organo-lithium reagent is preferably present in an amount in the range of from about 0.5 to about 2.0 molar equivalents, preferably in an amount in the range of from about 1.0 to about 1.2 molar equivalents;

in a mixture of a suitably selected ether solvent and a suitably selected hydrocarbon solvent, wherein the ether solvent is for example, diethyl ether, diisopropyl ether, di-n-butyl ether, MTBE, cyclopentylmethyl ether, and the like, preferably di-n-butyl ether or cyclopentyl methyl ether; and wherein hydrocarbon solvent is for example toluene, fluorobenzene, chlorobenzene, benzotrifluoride, and the like, preferably toluene; preferably at a temperature less than about room temperature, more preferably at a temperature in the range of from about −78° C. to about room temperature; to yield the corresponding compound of formula (VI-K), wherein M¹ is lithium. Preferably, the compound of formula (VI) is not isolated.

The compound of formula (VI-K) is reacted with a suitably selected zinc salt such as zinc dibromide (ZnBr₂), zinc diiodide (ZnI₂), zinc ditriflate, and the like, preferably ZnBr₂; or with an amine complex of zinc halide such as pyridine zinc bromide complex, N-methylmorpholine zinc bromide complex, and the like; wherein the zinc salt or amine complex of zinc halide is preferably present in an amount in the range of from about 0.33 to about 3.0 molar equivalents, more preferably in an amount in the range of from about 0.33 to about 1.0 molar equivalents, more preferably in an amount of about 0.5 molar equivalents;

in a mixture of a suitably selected ether solvent and a suitably selected hydrocarbon solvent, wherein the ether solvent is for example, diethyl ether, diisopropyl ether, di-n-butyl ether, MTBE, cyclopentylmethyl ether, and the like, preferably di-n-butyl ether or cyclopentyl methyl ether; and wherein hydrocarbon solvent is for example toluene, fluorobenzene, chlorobenzene, and the like, preferably toluene; preferably in the same mixture of solvents as used in the previous reaction step; to yield the corresponding compound of formula (VII-K), wherein M² is the corresponding zinc species, for example when the zinc salt is ZnBr₂, then in the compound of formula (VII-K), M² is ZnBr; wherein the zinc salt is ZnI₂, then in the compound of formula (VII-K), M² is ZnI; wherein the zinc salt is zinc ditriflate, then in the compound of formula (VII-K), M² is zinc triflate. Preferably, the compound of formula (VII-K) is not isolated.

Preferably, the compound of formula (VI-K) is reacted with a zinc salt, in the presence of a suitably selected amine or lithium salt such as lithium bromide, lithium iodide, pyridine, N-methyl morpholine, 2,6-lutidine, TMEDA, and the like; wherein the amine or lithium salt is preferably present in an amount in the range of from about 1.0 to about 2.0 molar equivalent.

The compound of formula (VII-K) is reacted with a suitably substituted compound of formula (VIII-S), wherein LG² is a suitably selected leaving group such as bromo, chloro, iodo, and the like, preferably bromo; and wherein each Z is independently a suitably selected oxygen protecting group, for example Z may selected from the group consisting of benzyl, benzoyl, pivaloyl, isobutyryl, p-methoxy-benzyl, and the like; preferably, each Z protecting group is the same, more preferably each Z is pivaloyl, a known compound or compound prepared by known methods; wherein the compound of formula (VIII) is preferably present in an amount in the range of from about 0.5 to about 3.0 molar equivalents, or any amount or range therein, more preferably in an amount in the range of from about 0.8 to about 1.25 molar equivalents, or any amount or range therein, more preferably in an amount of about 1.0 to about 1.1 molar equivalents;

in a mixture of a suitably selected ether solvent and a suitably selected hydrocarbon solvent, wherein the ether solvent is for example, diethyl ether, di-n-butyl ether, MTBE, 2-Me-THF, cyclopentylmethyl ether, and the like, preferably di-n-butyl ether or cyclopentyl methyl ether; and wherein hydrocarbon solvent is for example toluene, fluorobenzene, chlorobenzene, benzotrifluoride, and the like, preferably toluene; preferably in the same mixture of solvents as used in the previous reaction step; at a temperature in the range of from about room temperature to about reflux temperature, more preferably at a temperature in the range of from about 60° C. to about 95° C.; to yield the corresponding compound of formula (IX-K).

Preferably, the compound of formula (VIII-K), as a solution in a suitably selected hydrocarbon solvent, more preferably a suitably selected aromatic hydrocarbon, such as toluene, xylene, fluorobenzene, chlorobenzene, benzotrifluoride, and the like; is added to a solution of the compound of formula (VII-S) in a suitably selected ether solvent other than THF, such as diisopropyl ether, 1,4-dioxane, 2-methyl-THF, MTBE, cyclopentyl methyl ether (CPME), di-n-butyl ether, and the like, more preferably CPME or di-n-butyl ether. Preferably, the final solvent mixture is present in a volume ratio of ether solvent:hydrocarbon solvent of from about 1:1 to about 1:3.

The compound of formula (IX-K) is de-protected according to known methods, to yield the corresponding compound of formula (I-K). For example, wherein each Z is pivaloyl, the compound of formula (IX-K) may be de-protected by reacting with a suitably selected alkoxide or hydroxide base such as sodium methoxide, sodium ethoxide, lithium hydroxide, and the like, in a suitably selected solvent such as methanol, ethanol, and the like, to yield the corresponding compound of formula (I-K).

One skilled in the art will recognize that, depending on the particular protecting group Z, other reagents may be used in the de-protection step including, but not limited to, Pd/C, Pd(OH)$_2$, PdCl$_2$, Pd(OAc)$_2$/Et$_3$SiH, RaNi, a suitably selected acid, a suitably selected base, fluoride, and the like.

The compound of formula (I-K) is preferably isolated according to known methods, for example by extraction, filtration or column chromatography. The compound of formula (I-K) is further, preferably purified according to known methods, for example by recrystallization.

The present invention further comprises pharmaceutical compositions containing a compound prepared according to any of the processes described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein may contain, per unit dosage unit, e.g., tablet, capsule, powder, injection, suppository, teaspoonful and the like, of from about 0.01 to about 1000 mg or any amount or range therein, and may be given at a dosage of from about 0.01 to about 300 mg/kg/day, or any amount or range therein, preferably from about 0.1 to about 50 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treating described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably about 10 to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound prepared according to any of the processes described herein as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders as described herein is required.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter. In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 12 through 16 which follow herein, describe recipes/procedures for the synthesis of the title compounds. One or more batches of said compounds were prepared according to the recipes/procedures as described in these Examples.

EXAMPLE 1

(2S,3S,4R,5R,6R)-2-(3-((5-(4-fluorophenyl)thiophen-2-yl)methyl)-4-methylphenyl)-6-(pivaloyloxymethyl)tetrahydro-2H-pyran-3,4,5-triyl tris(2,2-dimethylpropanoate)

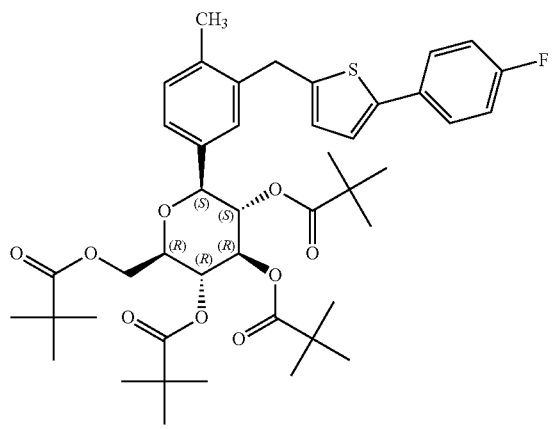

In a 250 mL RBF with mechanical stirrer, dried and under argon atmosphere, 2-(4-fluorophenyl)-5-(5-iodo-2-methylbenzyl)thiophene (22.20 mmoles; 9.06 g) was dissolved in a mixture of dried and degassed toluene (37.00 mL; 32.23 g)/diethyl ether (37.00 mL; 26.24 g) at room temperature. After cooling to −50° C. (isopropanol+dry ice bath) under vigorous stirring, (trimethylsilyl)methyllithium (1M in pentane, 37.00 mL) was added dropwise to the heterogeneous mixture. 30 min after the end of the addition, the conversion was checked by sampling and extra (trimethylsilyl)methyllithium was added if needed. After 15 min., zinc dibromide (22.20 mmoles; 5.00 g) (solid extra dry from Aldrich) was added in one portion and the resulting mixture was allowed to warm up to 25° C. over 1 hour. After 1 hour stirring at room temperature, diethyl ether and pentane were evaporated under reduced pressure (400 mmHg) at 15° C. Finally α-D-glucopyranosyl bromide, 2,3,4,6-tetrakis(2,2-dimethyl propanoate) (10.72 g, 18.50 mmoles) dissolved in degassed toluene (18.50 mL) was added dropwise over 10 min and the resulting mixture was heated at 75° C. for 21 hours. After cooling to room temperature, aqueous solution of ammonium chloride (1M, 100 mL) and ethyl acetate (150 mL) were added. After 10 min. stirring, the 2 phases were separated and the organic layer was washed twice with water (100 mL) and once with brine (100 mL). The organic layer was thereafter dried over sodium sulfate and the solvent was evaporated under reduced pressure to yield a clear brown oil. The oil was purified by MPLC (cartridge: 330 g $SiO_2$, solvent system: 95/5 to 85/15 heptane/AcOEt) to yield the title compound, (2S,3S,4R,5R,6R)-2-(3-((5-(4-fluorophenyl)thiophen-2-yl)methyl)-4-methylphenyl)-6-(pivaloyloxymethyl)tetrahydro-2H-pyran-3,4,5-triyl tris(2,2-dimethylpropanoate) as a single isomer. The $^1$H NMR spectrum was consistent with the previously measured $^1$H NMR spectra for the title compound.

EXAMPLE 2

(2S,3S,4R,5R,6R)-2-(3-((5-(4-fluorophenyl)thiophen-2-yl)methyl)-4-methylphenyl)-6-(pivaloyloxymethyl)tetrahydro-2H-pyran-3,4,5-triyl tris(2,2-dimethylpropanoate)

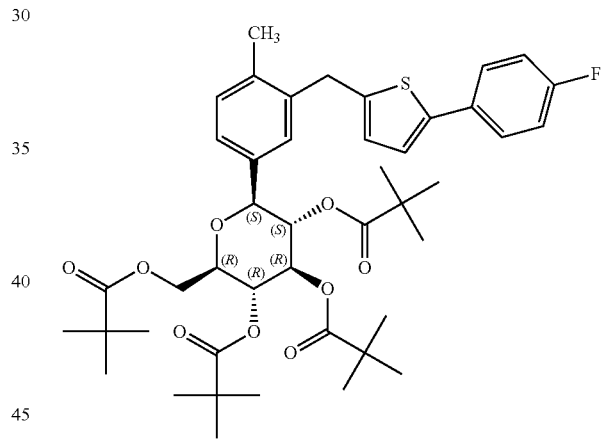

In a 25 mL Schlenk reactor, dried and under argon atmosphere, 2-(4-fluorophenyl)-5-(5-iodo-2-methylbenzyl)thiophene (1.99 mmoles; 813.71 mg) was dissolved in dry cyclopentylmethyl ether (CPME) (7.2 mL) at room temperature. After cooling to −50° C. (acetonitrile+dry ice) under vigorous stirring, n-hexyllithium (2.3M in hexane, 966.31 μL) was added dropwise to the mixture. After 15 min, zinc dibromide (996.50 μL; 2M solution in CPME) was added and the resulting mixture was allowed to warm up to 15° C. over 1.5 hour. Then α-D-glucopyranosyl bromide, 2,3,4,6-tetrakis(2,2-dimethyl propanoate) (1.05 g, 1.81 mmoles) dissolved in degassed CPME (1.81 mL) was added dropwise over 10 min and the resulting mixture was heated at 85° C. overnight. After cooling to room temperature, an aqueous solution of ammonium chloride (1M, 10 mL) and ethyl acetate (15 mL) were added. After 10 min. stirring, the 2 phases were separated, and the organic layer was washed twice with water (10 mL) and once with brine (10 mL). The organic layer was dried over sodium sulfate and the solvent was evaporated under reduced pressure to yield a clear brown oil, which was determined by quantitative HPLC to contain the title compound, (2S,3S,4R,5R,6R)-2-(3-((5-(4-fluorophenyl)thiophen-2-yl)methyl)-4-methylphenyl)-6-(pivaloyloxymethyl)tetrahydro-2H-pyran-3,4,5-triyl tris(2,2-dimethylpropanoate) as a single isomer. The $^1$H NMR spectrum was consistent with the previously measured $^1$H NMR spectra for the title compound.

fluorophenyl)thiophen-2-yl)methyl)-4-methylphenyl)-6-(pivaloyloxymethyl)tetrahydro-2H-pyran 3,4,5-triyl tris(2,2-dimethylpropanoate) as a single isomer. The $^1$H NMR spectrum was consistent with the previously measured $^1$H NMR spectra for the title compound.

EXAMPLE 3

(2S,3S,4R,5R,6R)-2-(3-((5-(4-fluorophenyl)thiophen-2-yl)methyl)-4-methylphenyl)-6-(pivaloyloxymethyl)tetrahydro-2H-pyran-3,4,5-triyl tris(2,2-dimethylpropanoate)

EXAMPLE 4

(2S,3S,4R,5R,6R)-2-(3-((5-(4-fluorophenyl)thiophen-2-yl)methyl)-4-methylphenyl)-6-(pivaloyloxymethyl)tetrahydro-2H-pyran-3,4,5-triyl tris(2,2-dimethylpropanoate)

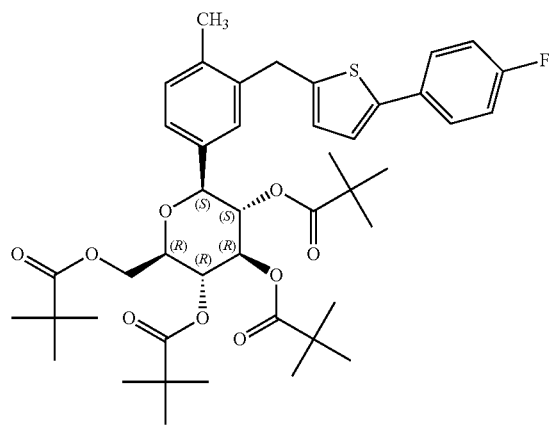

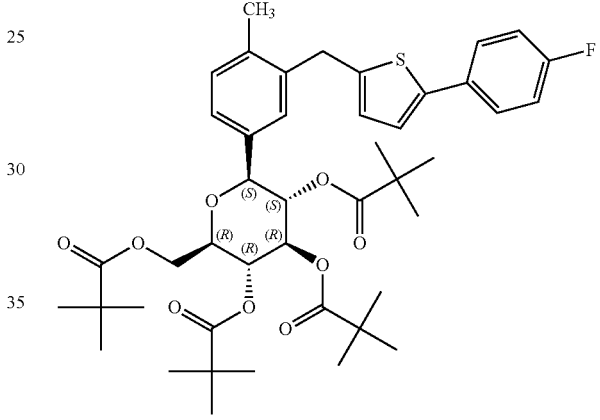

In a 25 mL Schlenk reactor, dried and under argon atmosphere, 2-(4-fluorophenyl)-5-(5-iodo-2-methylbenzyl)thiophene (1.90 mmoles; 775 mg) was dissolved in toluene (3.45 mL)/diethyl ether (3.45 mL) at room temperature. After cooling to −50° C. (acetonitrile+dry ice) under vigorous stirring, n-hexyllithium (2.3M in hexane, 920.29 μL) was added dropwise to the mixture. After 15 min., zinc dibromide (2.07 mmoles; 466 mg) was added in one portion and the resulting mixture was allowed to warm up to 15° C. over 1.5 hours. The resulting mixture was then cooled to 0° C. and (trimethylsilyl)methyllithium (1M in pentane, 1.9 mL) was added dropwise. After 1 hour, diethyl ether and hexane were evaporated under reduced pressure (400 mmHg) at 15° C. Then α-D-glucopyranosyl bromide, 2,3,4,6-tetrakis(2,2-dimethyl propanoate) (1.73 mmoles; 1.00 g) dissolved in degassed toluene (1.73 mL) was added dropwise over 10 min and the resulting mixture was heated at 85° C. overnight. After cooling to room temperature, aqueous solution of ammonium chloride (1M, 10 mL) and ethyl acetate (15 mL) were added. After 10 min. stirring, the 2 phases were separated and the organic layer was washed twice with water (10 mL) and once with brine (10 mL). The organic layer was dried over sodium sulfate and the solvent was evaporated under reduced pressure to yield a clear brown oil, which was determined by quantitative HPLC to contain the title compound, (2S,3S,4R,5R,6R)-2-(3-((5-(4-

In a 25 mL Schlenk reactor, dried and under argon atmosphere, 2-(4-fluorophenyl)-5-(5-iodo-2-methylbenzyl)thiophene (1.58 mmoles; 643 mg) was dissolved in toluene (2.86 mL)/2-methyltetrahydrofuran (2.86 mL) at room temperature. After cooling to −50° C. (acetonitrile+dry ice) under vigorous stirring, n-hexyllithium (2.3M in hexane; 764 μL) was added dropwise to the mixture. After 15 min., zinc dibromide (1.72 mmoles; 387 mg) dissolved in 2-methyltetrahydrofuran (859 μL) was added in one portion and the resulting mixture was allowed to warm up to 15° C. over 1.5 hours. Then α-D-glucopyranosyl bromide, 2,3,4,6-tetrakis(2,2-dimethyl propanoate) (1.43 mmoles; 830 mg) dissolved in degassed toluene (1.43 mL) was added dropwise over 10 min and the resulting mixture was heated at 85° C. overnight. After cooling to room temperature, an aqueous solution of ammonium chloride (1M, 10 mL) and ethyl acetate (15 mL) were added. After 10 min stirring, the phases were separated and the organic layer was washed twice with water (10 mL) and once with brine (10 mL). The organic layer was dried over sodium sulfate and the solvent was evaporated under reduced pressure to yield a clear brown oil, which was determined by quantitative HPLC to contain the title compound (2S,3S,4R,5R,6R)-2-(3-((5-(4-fluorophenyl)thiophen-2-yl)methyl)-4-methylphenyl)-6-(pivaloyloxymethyl)tetrahydro-2H-pyran-3,4,5-triyl tris(2,2-dimethylpropanoate) as a single isomer.

The $^1$H NMR spectrum was consistent with the previously measured $^1$H NMR spectra for the title compound.

EXAMPLE 5

(2S,3S,4R,5R,6R)-2-(3-((5-(4-fluorophenyl)thiophen-2-yl)methyl)-4-methylphenyl)-6-(pivaloyloxymethyl)tetrahydro-2H-pyran-3,4,5-triyl tris(2,2-dimethylpropanoate)

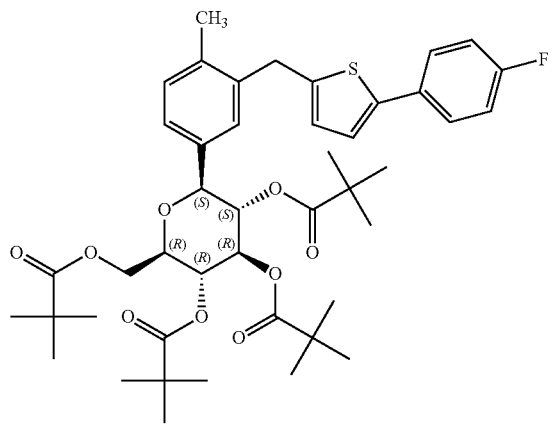

In a 25 mL Schlenk reactor, dried and under argon atmosphere, 2-(4-fluorophenyl)-5-(5-iodo-2-methylbenzyl)thiophene (1.90 mmoles; 775 mg) was dissolved in toluene (3.45 mL)/diethyl ether (3.45 mL) at room temperature. After cooling to −50° C. (acetonitrile+dry ice) under vigorous stirring, n-hexyllithium (2.3M in hexane, 920 μL) was added dropwise to the mixture. After 15 min, zinc dibromide (2.07 mmoles; 466 mg) was added in one portion and the resulting mixture was allowed to warm up to 15° C. over 1.5 hours. After 1 hour, diethyl ether and hexane were evaporated under reduced pressure (400 mmHg) at 15° C. Then α-D-glucopyranosyl bromide, 2,3,4,6-tetrakis(2,2-dimethyl propanoate) (1.73 mmoles; 1.00 g) dissolved in degassed toluene (1.73 mL) was added dropwise over 10 min and the resulting mixture was heated at 50° C. for 2 days. After cooling to room temperature, aqueous solution of ammonium chloride (1M, 10 mL) and ethyl acetate (15 mL) were added. After 10 min stirring, the phases were separated and the organic layer was washed twice with water (10 mL) and once with brine (10 mL). The organic layer was dried over sodium sulfate and the solvent was evaporated under reduced pressure to yield a clear brown oil, which was determined by quantitative HPLC to contain the title compound, (2S,3S,4R,5R,6R)-2-(3-((5-(4-fluorophenyl)thiophen-2-yl)methyl)-4-methylphenyl)-6-(pivaloyloxymethyl) tetrahydro-2H-pyran-3,4,5-triyl tris(2,2-dimethylpropanoate) as a single isomer. The $^1$H NMR spectrum was consistent with the previously measured $^1$H NMR spectra for the title compound.

EXAMPLE 6

(2S,3S,4R,5R,6R)-2-(3-((5-(4-fluorophenyl)thiophen-2-yl)methyl)-4-methylphenyl)-6-(pivaloyloxymethyl)tetrahydro-2H-pyran-3,4,5-triyl tris(2,2-dimethylpropanoate)

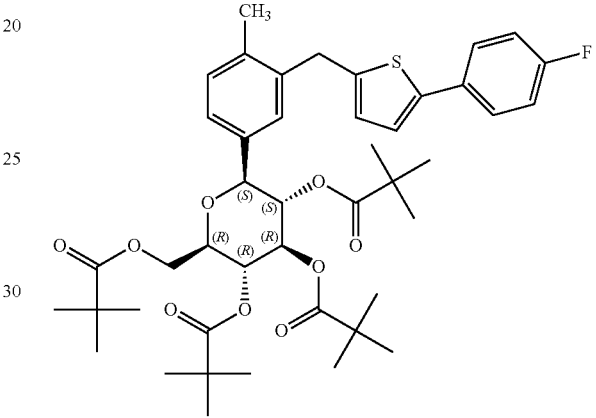

In a 25 mL Schlenk reactor, dried and under argon atmosphere, 2-(4-fluorophenyl)-5-(5-iodo-2-methylbenzyl)thiophene (2.60 mmoles; 1.06 g) was dissolved in toluene (4.73 mL)/Methoxy-cyclopentane (4.73 mL) at room temperature. After cooling to −50° C. (acetonitrile+dry ice) under vigorous stirring, n-hexyllithium (2.3M in hexane, 1.26 mL) was added dropwise to the mixture. After 15 min., zinc dibromide (2.84 mmoles; 639 mg) dissolved in dry methoxy-cyclopentane (1.40 mL) was added dropwise and the resulting mixture was allowed to warm up to 15° C. over 1 hour. Then α-D-glucopyranosyl bromide, 2,3,4,6-tetrakis(2,2-dimethyl propanoate) (2.36 mmoles; 1.37 g) dissolved in degassed toluene (2.36 mL) was added dropwise over 10 min and the resulting mixture was heated at 75° C. for 2 days. After cooling to room temperature, aqueous solution of ammonium chloride (1M, 10 mL) and ethyl acetate (15 mL) were added. After 10 ml. stirring, the phases were separated and the organic layer was washed twice with water (10 mL) and once with brine (10 mL). The organic layer was dried over sodium sulfate and the solvent was evaporated under reduced pressure to yield a clear brown oil, which was determined by quantitative HPLC to contain the title compound, (2S,3S,4R,5R,6R)-2-(3-((5-(4-fluorophenyl)thiophen-2-yl)methyl)-4-methylphenyl)-6-(pivaloyloxymethyl)tetrahydro-2H-pyran-3,4,5-triyltris(2,2-dimethylpropanoate) as a single isomer.

The ¹H NMR spectrum was consistent with the previously measured ¹H NMR spectra for the title compound.

EXAMPLE 7

(2S,3S,4R,5R,6R)-2-(3-((5-(4-fluorophenyl)thiophen-2-yl)methyl)-4-methylphenyl)-6-(pivaloyloxymethyl)tetrahydro-2H-pyran-3,4,5-triyltris(2,2-dimethylpropanoate)

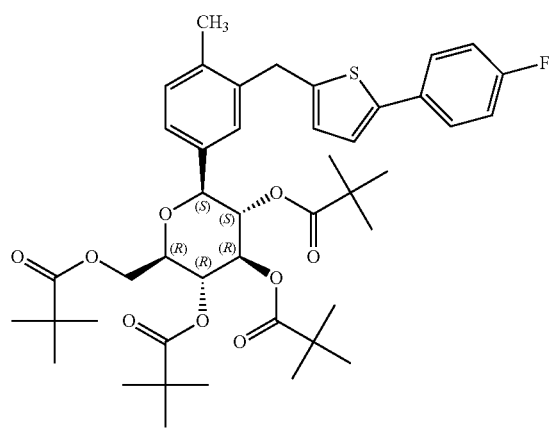

In a 50 mL Schlenk reactor under argon atmosphere at room temperature, 2-(4-fluorophenyl)-5-(5-iodo-2-methylbenzyl)thiophene (2.45 mmoles; 1.00 g) was dissolved in n-butyl ether (980 μL)/toluene (8.8 mL). The temperature was then decreased to −60° C. N-hexyllithium (2.3M in hexane, 1.20 mL) was added dropwise. After 2 hours, zinc dibromide (607 mg) was added in one portion at −60° C. The resulting mixture was allowed to warm up slowly to 10° C. over 2 hours. At 10° C., α-D-glucopyranosyl bromide, 2,3,4,6-tetrakis(2,2-dimethyl propanoate) (2.69 mmoles; 1.56 g) dissolved in toluene (2.69 mL) was added over 1 min. and the temperature was increased to 50° C. overnight. The temperature of the mixture was increased to 60° C. for 1 hour and finally for 2 days at 70° C. After cooling to room temperature, aqueous solution of ammonium chloride (1M, 10 mL) and ethyl acetate (15 mL) were added. After 10 min stirring, the phases were separated and the organic layer was washed twice with water (10 mL) and once with brine (10 mL). The organic layer was dried over sodium sulfate and the solvent was evaporated under reduced pressure to yield a clear brown oil, which was determined by quantitative HPLC to contain the title compound, (2S,3S,4R,5R,6R)-2-(3-((5-(4-fluorophenyl)thiophen-2-yl)methyl)-4-methylphenyl)-6-(pivaloyloxymethyl) tetrahydro-2H-pyran-3,4,5-triyl tris(2,2-dimethylpropanoate) as a single isomer. The ¹H NMR spectrum was consistent with the previously measured ¹H NMR spectra for the title compound.

EXAMPLE 8

(2R,3R,4S,5R,6R)-6-(pivaloyloxymethyl)tetrahydro-2H-pyran-2,3,4,5-tetrayl tetrakis(2,2-dimethylpropanoate)

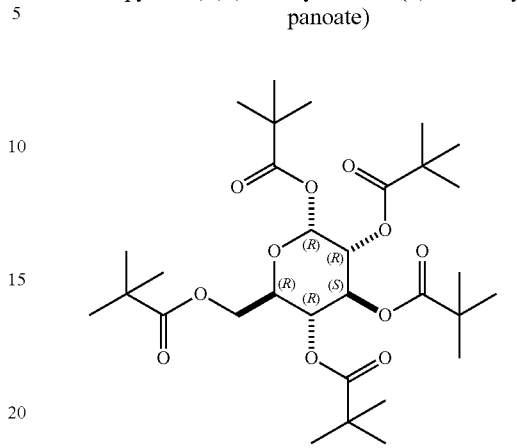

D-glucose (25.0 g, 0.139 mol) was suspended in anhydrous dichloromethane (416 mL) under nitrogen and the resulting mixture was stirred for 5 minutes at room temperature, then cooled to 0° C. and stirred for 10 minutes. To the resulting mixture was then added TEA (154.7 mL), dropwise over about 10-15 min, with stirring; then DMAP (1.25 g, 0.0102 mol) in one portion. To the resulting mixture was added pivaloyl chloride (136 mL) diluted with dichloromethane (83 mL) at 0° C., over 30 min. The ice bath was removed and the resulting mixture stirred at room temperature for 20 hours. The resulting mixture was then poured into dichloromethane (500 mL) and hydrochloric acid (1.5M, 375 mL) and the resulting phases separated. The organic layer was washed with sodium bicarbonate solution (550 g in 500 mL DI water, 1N) and then evaporated to a small volume. To the resulting residue was added ethanol (95%, 240 mL) and the mixture heated to reflux temperature to yield a homogeneous mixture. The resulting mixture was cooled to 0° C., resulting in the formation of white crystals, which were filtered and dried in vacuo at room temperature, overnight, to yield the title compound.

EXAMPLE 9

(2R,3R,4S,5R,6R)-2-bromo-6-(pivaloyloxymethyl)tetrahydro-2H-pyran-3,4,5-triyl tris(2,2-dimethylpropanoate)

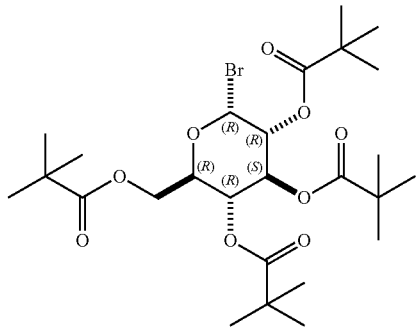

(2R,3R,4S,5R,6R)-6-(pivaloyloxymethyl)tetrahydro-2H-pyran-2,3,4,5-tetrayl tetrakis(2,2-dimethylpropanoate) (10.0 g, 16.65 mmol) was dissolved in anhydrous dichloromethane (100 mL) under nitrogen and stirred for 5 min at room temperature. To the mixture was then added zinc bromide (0.76 g, 3.33 mmol) and the resulting yellow solution stirred for 5 min at room temperature. To the mixture was then added TMS bromide (10.2 g, 66.58 mmol) diluted with dichloromethane (10 mL) over about 15-20 min and the resulting mixture stirred at room temperature for 24 hours. The resulting mixture was filtered to remove the solids and the filtrate cooled to 0° C. To the cooled filtrate was then added sodium bicarbonate solution (132 g in 120 mL water) to a final pH in the range of 7-8. The resulting phases were separated, the organic layer washed with water (120 mL) and the combined aqueous layers evaporated to a small volume. To the resulting residue was added IPA (39.3 g) and the mixture heated to dissolve. The resulting mixture was cooled to 0° C., resulting in the formation of white crystals, which were filtered and dried in vacuo at room temperature, overnight, to yield the title compound.

EXAMPLE 10

(2S,3S,4R,5R,6R)-2-(3-((5-(4-fluorophenyl)thiophen-2-yl)methyl)-4-methylphenyl)-6-(pivaloyloxymethyl)tetrahydro-2H-pyran-3,4,5-triyl tris(2,2-dimethylpropanoate)

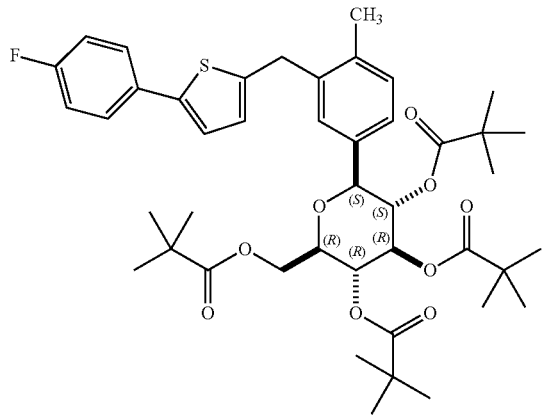

Step A: Preparation of Aryllithium Mixture 2-(4-Fluorophenyl)-5-(5-iodo-2-methylbenzyl)thiophene (12.81 g, 31.37 mmol) was placed in a dry Schlenk tube under an argon atmosphere. Anhydrous toluene (15.7 mL) and anhydrous CPME (9.4 mL) were added by syringe, without stirring and the resulting mixture cooled to −45° C. and then stirred. To the resulting cooled mixture was then added n-hexyllithium (14.3 g, 32.94 mmol), as a 2.5M solution in hexane (14.3 mL) over about 5-10 min; and the mixture warmed to −25° C. over 1 hour.

Step B: Preparation of Title Compound

Zinc bromide (3.88 g, 17.25 mmol) and lithium bromide (2.72 g, 34.50 mmol) were dried at 200° C. in vacuo, in anhydrous CPME (18.6 mL) in a Schlenk tube. The mixture was then added by cannula, at −25° C. to the aryllithium mixture (prepared as described in STEP A above) and the resulting mixture was warmed to 0° C. over 1 hour. To the resulting mixture was then added (2R,3R,4S,5R,6R)-2-bromo-6-(pivaloyloxymethyl)tetrahydro-2H-pyran-3,4,5-thiyl tris(2,2-dimethylpropanoate) (20.0 g, 34.50 mmol) in anhydrous toluene (31.4 mL). The ice bath was removed and the resulting mixture stirred at room temperature for 30 min; then heated to 65° C. for 48 hours. The resulting suspension was filtered through a glass frit, rinsed with toluene (20 mL) and the filtrate washed with 1N ammonium chloride solution (100 mL) and water (100 mL). The toluene was distilled off to a small volume. Methanol (157 mL) was added to the resulting residue and the mixture cooled to 0° C., resulting in the formation of crystals, which were filtered and dried in vacuo at 40° C., overnight, to yield the title compound

EXAMPLE 11

(2S,3R,4R,5S,6R)-2-(3-((5-(4-fluorophenyl)thiophen-2-yl)methyl)-4-methylphenyl)-6-(hydroxymethyl)tetrahydro-2H-pyran-3,4,5-triol

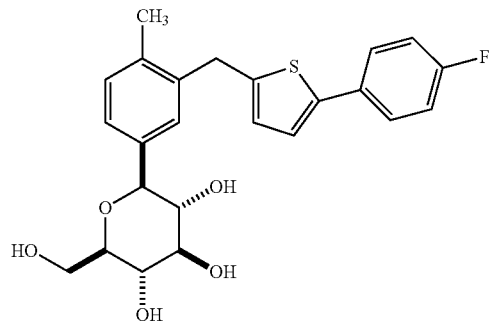

(2S,3S,4R,5R,6R)-2-(3-((5-(4-fluorophenyl)thiophen-2-yl)methyl)-4-methylphenyl)-6-(pivaloyloxymethyl)tetrahydro-2H-pyran-3,4,5-triyltris(2,2-dimethylpropanoate) (39.0 g, 50.0 mmol) was suspended in methanol (150 mL) at room temperature. Sodium methoxide solution (9.3 mL) was added and the resulting suspension was stirred at room temperature, heated to 60° C. for 16 hours and then cooled. To the resulting yellow solution was then added water (50 mL) and seeds to the title compound. An additional portion of water (50 mL) was added, and the mixture stirred at 0° C. for 1 hour, resulting in the formation of a precipitate, which was collected by filtration to yield the title compound.

EXAMPLE 12

(2R,3R,4R,5S,6S)-2-(pivaloyloxymethyl)-6-p-tolyltetrahydro-2H-pyran-3,4,5-triyltris(2,2-dimethylpropanoate)

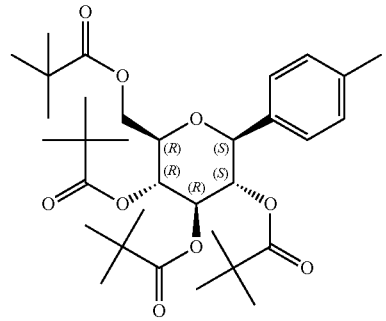

In a 10 mL Schlenk tube under argon atmosphere, a solution of lithium dibutyl hexylmagnesate (0.4 eq, 0.35 mmol) was added dropwise to a mixture of 4-iodotoulene (230 mg, 1.04 mmol) dissolved in anhydrous toluene (0.43 mL) and anhydrous n-dibutylether (0.26 mL) at 0° C. After complete halogen-metal exchange (as determined by GC or HPLC), a solution of ZnBr$_2$.LiBr in dibutylether (34 w/w %, 0.6 eq, 0.52 mmol) was added dropwise. After 1 hour, (2R,3R,4S,5R,6R)-2-bromo-6-(pivaloyloxymethyl)tetrahydro-2H-pyran-3,4,5-triyltris(2,2-dimethylpropanoate) (1 eq, 500 mg, 0.86 mmol) dissolved in anhydrous toluene (0.86 mL) was added to the organozinc mixture. The resulting mixture was heated to 100° C. until complete conversion (as determined by GC). After cooling to room temperature, the resulting mixture was quenched with aqueous HCl 1M (10 mL). The two layers were then separated. The aqueous layer was extracted with ethyl acetate (10 mL). The combined organic layer was washed with water (10 mL), and then washed with a brine solution (10 mL). The organic layer was dried through a pre-packed column and concentrated in a rotavaporator under reduced pressure. The resulting mixture was purified by chromatography on silicagel to yield the title compound as a residue.

EXAMPLE 13

(2S,3S,4R,5R,6R)-2-(4-methoxyphenyl)-6-(pivaloyloxymethyl)tetrahydro-2H-pyran-3,4,5-triyltris(2,2-dimethylpropanoate)

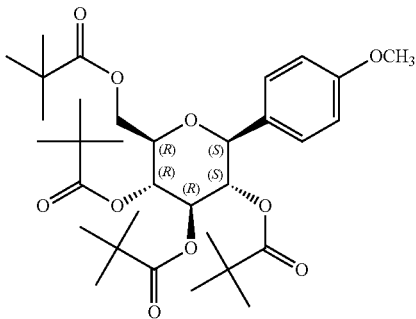

In a 10 mL Schlenk tube under argon atmosphere, a solution of lithium dibutyl hexylmagnesate (0.4 eq, 0.35 mmol) was added dropwise to a mixture of 4-iodoanisole (250 mg, 1.04 mmol) dissolved in anhydrous toluene (0.43 mL) and anhydrous n-dibutylether (0.26 mL) at 0° C. After complete halogen-metal exchange, a solution of ZnBr$_2$.LiBr in dibutylether (34 w/w %, 0.6 eq, 0.52 mmol) was added drop wise. After 1 hour, (2R,3R,4S,5R,6R)-2-bromo-6-(pivaloyloxymethyl)tetrahydro-2H-pyran-3,4,5-triyltris(2,2-dimethylpropanoate) (1 eq, 500 mg, 0.86 mmol) dissolved in anhydrous toluene (0.86 mL) was added to the organozinc mixture. The resulting mixture was heated to 100° C. until complete conversion (as determined by GC). After cooling to room temperature, the resulting mixture was quenched with aqueous HCl 1M (10 mL). The two layers were then separated. The aqueous layer was extracted with ethyl acetate (10 mL). The combined organic layer was washed with water (10 mL), and then washed with a brine solution (10 mL). The organic layer was dried through a pre-packed column and concentrated in rotavaporator under reduced pressure. The resulting mixture was purified by crystallization to yield the title compound as a residue.

EXAMPLE 14

(2S,3S,4R,5R,6R)-2-(2,6-dimethoxyphenyl)-6-(pivaloyloxymethyl)tetrahydro-2H-pyran-3,4,5-triyltris(2,2-dimethylpropanoate

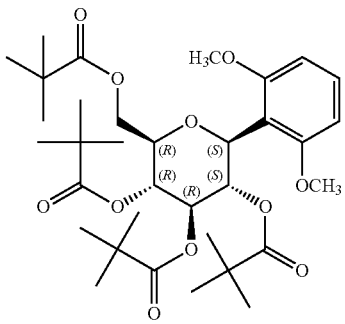

In a 10 mL Schlenk tube under argon atmosphere, a solution of sec-butyl lithium (1.2 eq, 4.14 mmol) was added dropwise to a mixture of 1,3-dimethoxybenzene (0.54 mL, 4.14 mmol) dissolved in anhydrous toluene (1.72 mL) and anhydrous n-dibutylether (1.04 mL) at 0° C. After complete halogen-metal exchange, a solution of ZnBr$_2$.LiBr in dibutylether (34 w/w %, 0.6 eq, 2.07 mmol) was added drop wise. After 1 hour, (2R,3R,4S,5R,6R)-2-bromo-6-(pivaloyloxymethyl)tetrahydro-2H-pyran-3,4,5-triyltris(2,2-dimethylpropanoate) (1 eq, 2000 mg, 3.45 mmol) dissolved in anhydrous toluene (3.44 mL) was added to the organozinc mixture. The resulting mixture was heated to 100° C. until complete conversion (as determined by GC). After cooling to room temperature, the resulting mixture was quenched with aqueous HCl 1M (40 mL). The two layers were then separated. The aqueous layer was extracted with ethyl acetate (40 mL). The combined organic layer was washed with water (40 mL), and then washed with a brine solution (40 mL). The organic layer was dried through a pre-packed column and concentrated in rotavaporator under reduced pressure. The resulting mixture was purified by chromatography on silicagel to yield the title compound as a residue.

EXAMPLE 15

(2R,3R,4R,5S,6S)-2-(pivaloyloxymethyl)-6-(4-(trifluoromethyl)phenyl)tetrahydro-2H-pyran-3,4,5-triyltris(2,2-dimethylpropanoate)

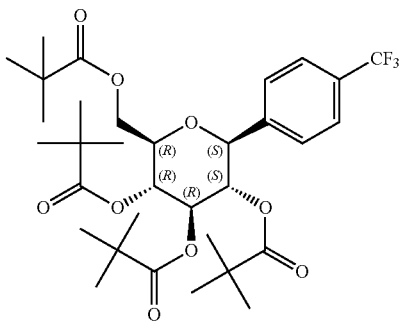

In a 10 mL Schlenk tube under argon atmosphere, a solution of lithium dibutyl hexylmagnesate (0.4 eq, 0.35 mmol) was added drop wise to a mixture of 4-iodobenzotrifluoride (0.15 mL, 1.04 mmol) dissolved in anhydrous toluene (0.43 mL) and anhydrous n-dibutylether (0.26 mL) at −50° C. After complete halogen-metal exchange, a solution of ZnBr$_2$.LiBr in dibutylether (34 w/w %, 0.6 eq, 0.52 mmol) was added dropwise. After 1 hour, (2R,3R,4S,5R,6R)-2-bromo-6-(pivaloyloxymethyl)tetrahydro-2H-pyran-3,4,5-triyltris(2,2-dimethylpropanoate) (1 eq, 500 mg, 0.86 mmol) dissolved in anhydrous toluene (0.86 mL) was added to the organozinc mixture. The resulting mixture was heated to 100° C. until complete conversion (as determined by GC). After cooling to room temperature, the resulting mixture was quenched with aqueous HCl 1M (10 mL). The two layers were then separated. The aqueous layer was extracted with ethyl acetate (10 mL). The combined organic layer was washed with water (10 mL), and then washed with a brine solution (10 mL). The organic layer as dried through a pre-packed column and concentrated in rotavaporator under reduced pressure. The resulting mixture was purified by purification on reverse phase (Kromasil C18) to yield the title compound as a residue.

EXAMPLE 16

(2R,3R,4S,5R,6R)-2-(pivaloyloxymethyl)-6-(thiophene-2-yl)tetrahydro-2H-pyran-3,4,5-triyltris(2,2-di-methylpropanoate)

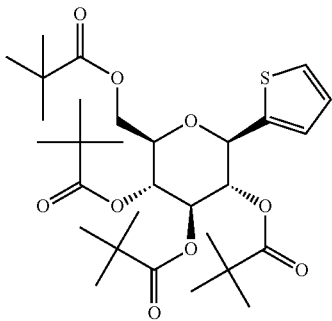 [SMILES: CC(C)(C)C(=O)OC[C@H]1O[C@@H](c2cccs2)[C@H](OC(=O)C(C)(C)C)[C@@H](OC(=O)C(C)(C)C)[C@@H]1OC(=O)C(C)(C)C]

In a 10 mL Schlenk tube under argon atmosphere, a solution of lithium dibutyl hexylmagnesate (0.4 eq, 0.35 mmol) was added dropwise to a mixture of 2-iodothiphene (0.115 mL, 1.04 mmol) dissolved in anhydrous toluene (0.43 mL) and anhydrous n-dibutylether (0.26 mL) at 0° C. After complete halogen-metal exchange, a solution of ZnBr$_2$.LiBr in dibutylether (34 w/w %, 0.6 eq, 0.52 mmol) as added dropwise. After 1 hour, (2R,3R,4S,5R,6R)-2-bromo-6-(pivaloyloxymethyl)tetrahydro-2H-pyran-3,4,5-triyltris(2,2-dimethylpropanoate) (1 eq, 500 mg, 0.86 mmol) dissolved in anhydrous toluene (0.86 mL) was added to the organozinc mixture. The resulting mixture was heated to 100° C. until complete conversion (control by GC). After cooling to room temperature, the resulting mixture was quenched with aqueous HCl 1M (10 mL). The two layers were then separated. The aqueous layer as extracted with ethyl acetate (10 mL). The combined organic layer was washed with water (10 mL), and then washed with a brine solution (10 mL). The organic layer as dried through a pre-packed column and concentrated in rotavaporator under reduced pressure. The resulting mixture was purified by purification on reverse phase (Kromasil C18) to yield the title compound as a residue.

EXAMPLE 17

Solid, Oral Formulation

Prophetic Example

As a specific embodiment of an oral composition, 100 mg of the compound prepared as in Example 11 above, is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for the preparation of compounds of formula (I)

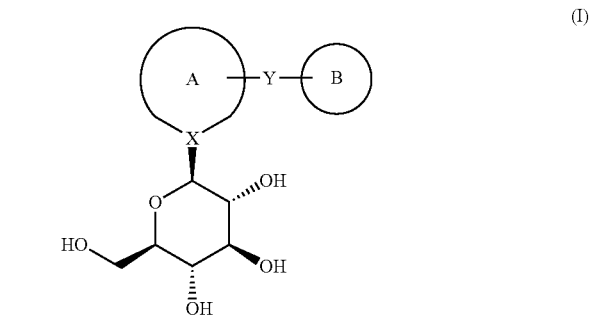

wherein Ring A and Ring B are one of the following:
(1) Ring A is an optionally substituted unsaturated monocyclic heterocyclic ring, and Ring B is an optionally substituted unsaturated monocyclic heterocyclic ring, an optionally substituted unsaturated fused heterobicyclic ring, or an optionally substituted benzene ring; or
(2) Ring A is an optionally substituted benzene ring, and Ring B is an optionally substituted unsaturated monocyclic heterocyclic ring, or an optionally substituted unsaturated fused heterobicyclic ring wherein Y is linked to the heterocyclic ring of the fused heterobicyclic ring; or
(3) Ring A is an optionally substituted unsaturated fused heterobicyclic ring, wherein the sugar moiety X-(sugar) and the moiety —Y-(Ring B) are both on the same heterocyclic ring of the fused heterobicyclic ring, and Ring B is an optionally substituted unsaturated monocyclic heterocyclic ring, an optionally substituted unsaturated fused heterobicyclic ring, or an optionally substituted benzene ring;
X is a carbon atom;
Y is —(CH$_2$)$_n$—; wherein n is 1 or 2;
provided that in Ring A, X is part of an unsaturated bond; or a pharmaceutically acceptable salt or solvate thereof; comprising

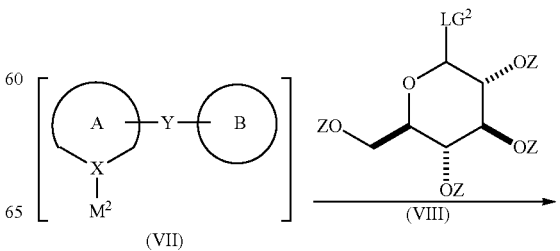

-continued

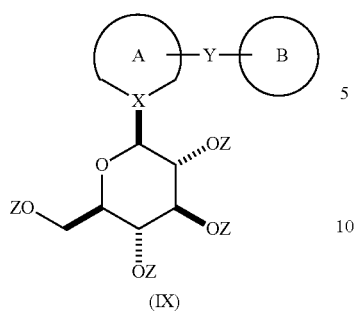

(IX)

reacting a compound of formula (VII), wherein $M^2$ is a zinc species, with a compound of formula (VIII), wherein each Z is pivaloyl and wherein $LG^2$ is bromo; in a mixture of an ether solvent and a hydrocarbon solvent; wherein the ether solvent is selected from the group consisting of di-n-butyl ether and cyclopentylmethyl ether; at a temperature in the range of from about 60° C. to about 95° C.; to yield the corresponding compound of formula (IX);

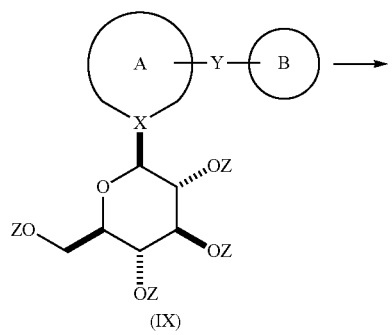

(IX)

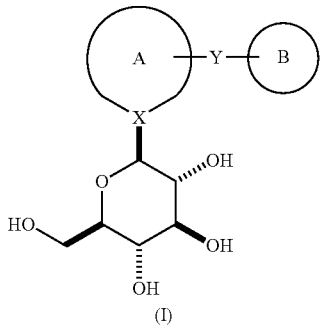

(I)

de-protecting the compound of formula (IX); to yield the corresponding compound of formula (I).

2. A process as in claim 1, further comprising

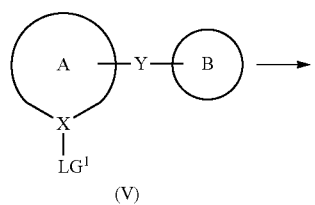

(V)

-continued

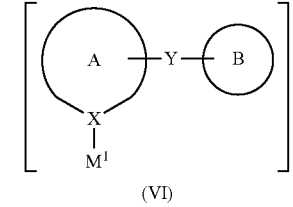

(VI)

reacting a compound of formula (V), wherein $LG^1$ is a leaving group, with an organo-lithium reagent; in a mixture of an ether solvent and a hydrocarbon solvent; wherein the ether solvent is selected from the group consisting of di-n-butyl ether and cyclopentylmethyl ether; to yield the corresponding compound of formula (VI), wherein $M^1$ is lithium;

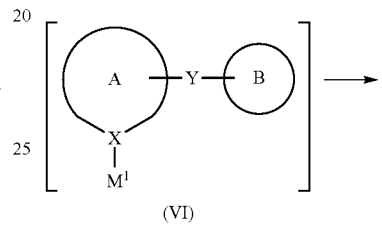

(VI)

(VII)

reacting the compound of formula (VI) with a zinc salt or an amine complex of zinc halide; wherein the ether solvent is selected from the group consisting of di-n-butyl ether and cyclopentylmethyl ether; in a mixture of an ether solvent and a hydrocarbon solvent; to yield the corresponding compound of formula (VII).

3. A process as in claim 1, wherein $M^2$ is ZnBr.

4. A process as in claim 1, wherein the compound of formula (VIII) is present in an amount in the range of from about 1.0 to about 1.1 molar equivalents.

5. A process as in claim 1, wherein the hydrocarbon solvent is toluene.

6. A process as in claim 2, wherein the organo-lithium reagent is n-hexyl lithium; and wherein the n-hexyl lithium is present in an amount in the range of from about 1.0 to about 1.2 molar equivalents.

7. A process as in claim 2, wherein the hydrocarbon solvent is toluene.

8. A process as in claim 2, wherein the zinc salt is selected from the group consisting of zinc dibromide ($ZnBr_2$), zinc diiodide ($ZnI_2$) and zinc ditriflate; and wherein the amine complex of zinc halide is selected from the group consisting of pyridine zinc bromide complex and N-methylmorpholine zinc bromide complex.

9. A process as in claim 2, wherein the compound of formula (VI) is reacted with a zinc salt; wherein the zinc salt is zinc dibromide and wherein the zinc dibromide is present in an amount in the range of from about 0.33 to about 1.0 molar equivalents.

10. A process as in claim 1, wherein
X is a carbon atom;
Ring A is selected from the group consisting of 4-methylphenyl and 4-chlorophenyl;
Y is —CH$_2$— and is bound at the 3-position of Ring A; and
Ring B is selected from the group consisting of 2-(5-(4-fluorophenyl)-thienyl) and 2-(5-(6-fluoro-pyrid-3-yl)thienyl).

11. A process as in claim 1, wherein X is a carbon atom; Ring A is 4-methyl-phenyl; Y is —CH$_2$— and is bound at the 3-position of Ring A; and
Ring B is 5-(4-fluorophenyl)-thien-5-yl.

12. A process for the preparation of a compound of formula (I-S)

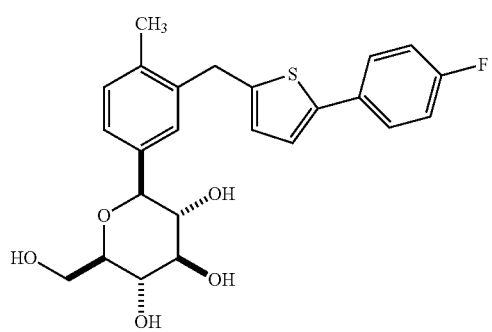

(I-S)

or solvate thereof; comprising

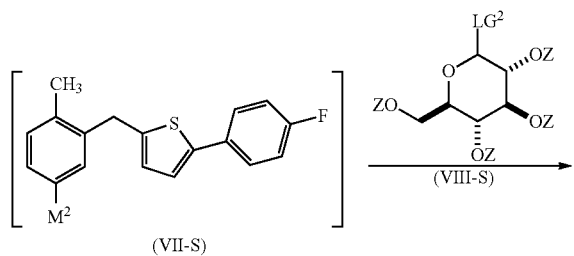

reacting a compound of formula (VII-S), wherein M$^2$ is a zinc species, with a compound of formula (VIII-S), wherein each Z is pivaloyl and wherein LG$^2$ is bromo; in a mixture of an ether solvent and a hydrocarbon solvent; wherein the ether solvent is selected from the group consisting of di-n-butyl ether and cyclopentylmethyl ether; at a temperature in the range of from about 60° C. to about 95° C.; to yield the corresponding compound of formula (IX-S);

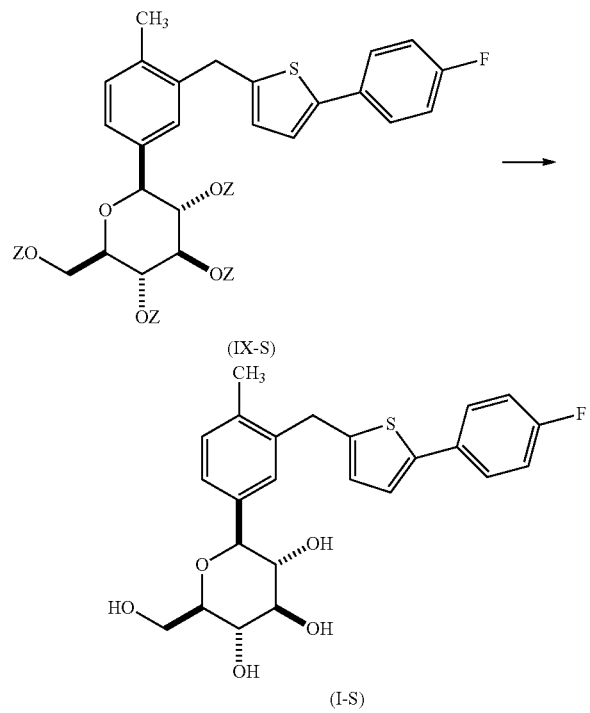

de-protecting the compound of formula (IX-S); to yield the corresponding compound of formula (I-S).

13. A process as in claim 12, wherein M$^2$ is ZnBr.

14. A process as in claim 12, wherein the compound of formula (VIII-S) is present in an amount in the range of from about 0.8 to about 1.25 molar equivalents.

15. A process as in claim 14, wherein the compound of formula (VIII-S) is present in an amount in the range of from about 1.0 to about 1.1 molar equivalents.

16. A process as in claim 12, wherein the hydrocarbon solvent is toluene.

17. A process as in claim 12, wherein the compound of formula (VIII-S) in a solution of the hydrocarbon solvent is added to the compound of formula (VII-S) in a solution of the ether solvent.

18. A process as in claim 12, further comprising

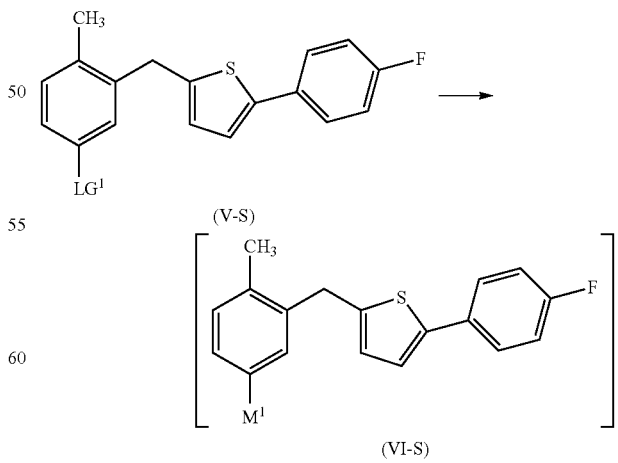

reacting a compound of formula (V-S), wherein LG$^1$ is a leaving group; with an organo-lithium reagent; in a mixture of an ether solvent and a hydrocarbon solvent; wherein the ether solvent is selected from the group consisting of di-n-butyl ether and cyclopentylmethyl ether; to yield the corresponding compound of formula (VI-S), wherein $M^1$ is lithium;

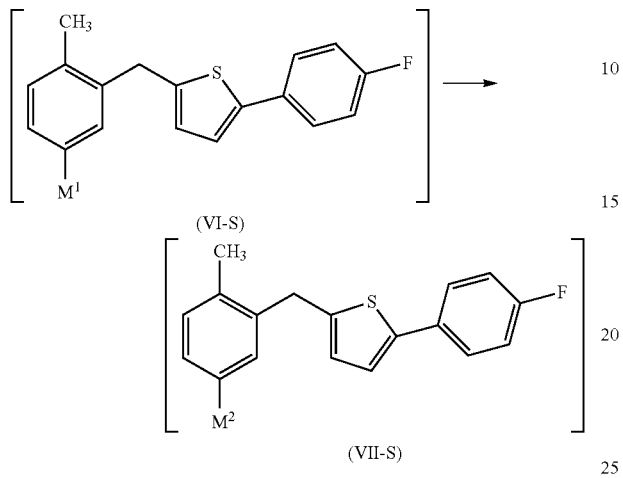

reacting the compound of formula (VI-S) with a zinc salt or an amine complex of zinc halide; in a mixture of an ether solvent and a hydrocarbon solvent; wherein the ether solvent is selected from the group consisting of di-n-butyl ether and cyclopentylmethyl ether; to yield the corresponding compound of formula (VII-S).

19. A process as in claim 18, wherein the organo-lithium reagent is n-hexyl lithium.

20. A process as in claim 18, wherein the organo-lithium reagent is present in an amount in the range of from about 0.5 to about 2.0 molar equivalents.

21. A process as in claim 20, wherein the organo-lithium reagent is present in an amount in the range of from about 1.0 to about 1.2 molar equivalents.

22. A process as in claim 18, wherein the hydrocarbon solvent is toluene.

23. A process as in claim 18, wherein the compound of formula (V-S) is reacted with the organo-lithium reagent at a temperature in the range of from about −78° C. to about room temperature.

24. A process as in claim 18, wherein the zinc salt is selected from the group consisting of zinc dibromide ($ZnBr_2$), zinc diiodide ($ZnI_2$) and zinc ditriflate; and wherein the amine complex of zinc halide is selected from the group consisting of pyridine zinc bromide complex and N-methylmorpholine zinc bromide complex.

25. A process as in claim 18, wherein the compound of formula (VI-S) is reacted with a zinc salt; and wherein the zinc salt is zinc dibromide.

26. A process as in claim 25, wherein the zinc dibromide is present in an amount in the range of from about 0.33 to about 1.0 molar equivalents.

27. A process as in claim 26, wherein the zinc dibromide is present in an amount of about 0.5 molar equivalents.

28. A process as in claim 18, wherein the compound of formula (VI-S) is reacted with a zinc salt in the presence of an amine or lithium salt.

29. A process as in claim 28, wherein the amine or lithium salt is selected from the group consisting of lithium bromide, lithium iodide, pyridine, N-methyl morpholine, 2,6-lutidine and TMEDA.

30. A process for the preparation of a compound of formula (X-P)

wherein both $Q^1$ groups are the same and are

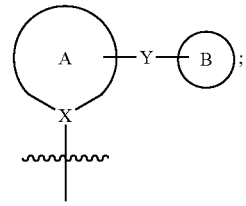

and wherein Ring A and Ring B are one of the following:
(1) Ring A is an optionally substituted unsaturated monocyclic heterocyclic ring, and Ring B is an optionally substituted unsaturated monocyclic heterocyclic ring, an optionally substituted unsaturated fused heterobicyclic ring, or an optionally substituted benzene ring; or
(2) Ring A is an optionally substituted benzene ring, and Ring B is an optionally substituted unsaturated monocyclic heterocyclic ring, or an optionally substituted unsaturated fused heterobicyclic ring wherein Y is linked to the heterocyclic ring of the fused heterobicyclic ring; or
(3) Ring A is an optionally substituted unsaturated fused heterobicyclic ring, wherein the sugar moiety X-(sugar) and the moiety —Y-(Ring B) are both on the same heterocyclic ring of the fused heterobicyclic ring, and Ring B is an optionally substituted unsaturated monocyclic heterocyclic ring, an optionally substituted unsaturated fused heterobicyclic ring, or an optionally substituted benzene ring;

X is a carbon atom;
Y is —$(CH_2)_n$—; wherein n is 1 or 2;
provided that in Ring A, X is part of an unsaturated bond;

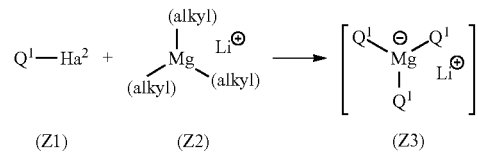

reacting a compound of the formula (Z1), wherein $Ha^2$ is a halogen, with a lithium trialkyl magnesate, a compound of formula (Z2); in a suitably selected anhydrous organic solvent or mixture or anhydrous organic solvents; to yield the corresponding compound of formula (Z3);

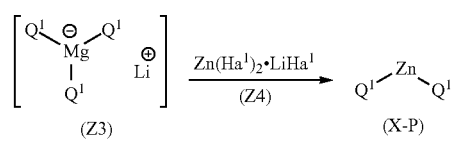

reacting the compound of formula (Z3) with a zinc halide.lithium halide complex, a compound of formula (Z4), wherein Ha$^1$ is a halogen; in a suitably selected anhydrous organic solvent or mixture or anhydrous organic solvents; to yield the corresponding compound of formula (X-P).

31. A process as in claim 30, wherein the compound of formula (Z2) is lithium dibutyl hexylmagnesate; and wherein the compound of formula (Z4) is zinc bromide.lithium bromide complex.

32. A process as in claim 30, wherein the compound of formula (X-P) is a compound of formula (X-S)

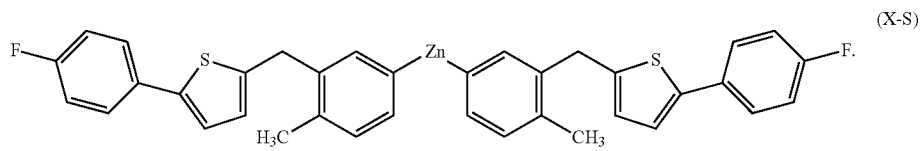

33. A process as in claim 1, wherein the hydrocarbon solvent is selected from the group consisting of toluene, fluorobenzene, cholorbenzene and benzotrifluoride.

34. A process as in claim 12, wherein the hydrocarbon solvent is selected from the group consisting of toluene, fluorobenzene, chlorobenzene and benzotrifluoride.

35. A process as in claim 29, wherein the amine or lithium salt is present in an amount in the range of from about 1.0 to about 2.0 molar equivalent.

* * * * *

UNITED STATES PATENT AND TRADEMARK OFFICE
CERTIFICATE OF CORRECTION

PATENT NO. : 9,174,971 B2
APPLICATION NO. : 12/904233
DATED : November 3, 2015
INVENTOR(S) : Farina et al.

It is certified that error appears in the above-identified patent and that said Letters Patent is hereby corrected as shown below:

IN THE CLAIMS

Column 78
Lines 46-53, delete

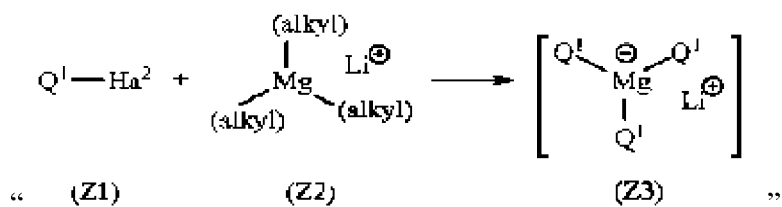

and insert

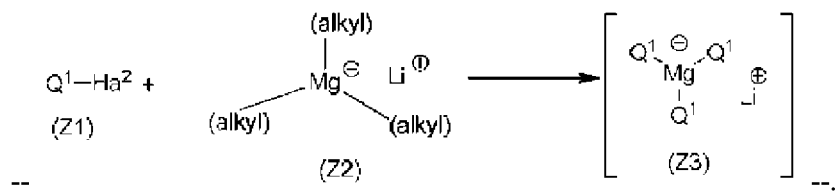

Column 79
Line 2, delete "halide.lithium" and insert --halide•lithium--.

Column 79
Line 9, delete "bromide.lithium" and insert --bromide•lithium--.

Signed and Sealed this
Twenty-ninth Day of March, 2016

Michelle K. Lee
*Director of the United States Patent and Trademark Office*